(12) United States Patent
Armani et al.

(10) Patent No.: US 7,781,217 B2
(45) Date of Patent: Aug. 24, 2010

(54) BIOLOGICAL AND CHEMICAL MICROCAVITY RESONANT SENSORS AND METHODS OF DETECTING MOLECULES

(75) Inventors: Andrea M. Armani, Pasadena, CA (US); Rajan P. Kulkarni, Loma Linda, CA (US); Scott E. Fraser, Pasadena, CA (US); Kerry J. Vahala, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/733,480

(22) Filed: Apr. 10, 2007

(65) Prior Publication Data
US 2007/0269901 A1 Nov. 22, 2007

Related U.S. Application Data

(63) Continuation-in-part of application No. 10/678,354, filed on Oct. 2, 2003.

(60) Provisional application No. 60/790,667, filed on Apr. 10, 2006, provisional application No. 60/415,412, filed on Oct. 2, 2002.

(51) Int. Cl.
*G01N 23/00* (2006.01)
(52) U.S. Cl. ...................................................... 436/57
(58) Field of Classification Search .................... 436/57
See application file for complete search history.

(56) References Cited

U.S. PATENT DOCUMENTS

| | | |
|---|---|---|
| 3,589,794 A | 6/1971 | Marcatti |
| 3,760,297 A | 9/1973 | Thompson |
| 3,913,126 A | 10/1975 | Hooker |
| 4,071,753 A | 1/1978 | Fulenwider et al. |
| 4,282,499 A | 8/1981 | DeFonzo |

(Continued)

FOREIGN PATENT DOCUMENTS

FR 2 703 473 10/1994

(Continued)

OTHER PUBLICATIONS

Boyd, R. W.; Heebner, J.E. "Sensitive disk resonator photonic biosensor." Applied Optics. 2001, 40 (31), 5742-5747.*

(Continued)

*Primary Examiner*—Walter D Griffin
*Assistant Examiner*—Bobby Ramdhanie
(74) *Attorney, Agent, or Firm*—Vista IP Law Group LLP

(57) ABSTRACT

Resonant sensors and methods of detecting specific molecules with enhanced sensitivity. Optical energy is introduced into a microcavity, such as a silica toroid-shaped microcavity. The microcavity sensor has a functionalized outer surface and a sufficiently high Q value to generate an evanescent optical field with increased intensity. A molecule bound to the functionalized outer surface interacts with the external optical field, thereby heating the microcavity and generating a detectable resonant wavelength shift, which indicates a small number of molecules, even a single molecule, without the use of fluorescent or metal labels. Resonant sensors and methods can also be used to detect specific molecules, even a single molecule, within an environment. One application is detecting very small quantities or a single molecule of heavy water in ordinary water.

38 Claims, 34 Drawing Sheets

U.S. PATENT DOCUMENTS

| | | | |
|---|---|---|---|
| 4,419,895 | A | 12/1983 | Fuller |
| 4,695,121 | A | 9/1987 | Mahapatra et al. |
| 5,114,738 | A | 5/1992 | Savage et al. |
| 5,343,490 | A | 8/1994 | McCall |
| 5,651,022 | A | 7/1997 | Anthon |
| 5,825,799 | A | 10/1998 | Ho et al. |
| 5,878,070 | A | 3/1999 | Ho et al. |
| 6,052,495 | A | 4/2000 | Little et al. |
| 6,078,605 | A | 6/2000 | Little et al. |
| 6,101,300 | A | 8/2000 | Fan et al. |
| 6,222,964 | B1 | 4/2001 | Sadot et al. |
| 6,259,717 | B1 | 7/2001 | Stone |
| 6,490,039 | B2 * | 12/2002 | Maleki et al. ............... 356/436 |
| 6,583,399 | B1 | 6/2003 | Hunziker et al. |
| 6,657,731 | B2 * | 12/2003 | Tapalian et al. ............. 356/480 |
| 6,901,101 | B2 | 5/2005 | Frick |
| 2001/0033587 | A1 | 10/2001 | Vahala et al. |
| 2002/0018611 | A1 | 2/2002 | Maleki et al. |
| 2003/0021518 | A1 | 1/2003 | Simirnov et al. |
| 2003/0179981 | A1 | 9/2003 | Lee et al. |
| 2004/0179573 | A1 | 9/2004 | Armani et al. |
| 2005/0163185 | A1 | 7/2005 | Vahala et al. |
| 2006/0062523 | A1 | 3/2006 | Guo et al. |

FOREIGN PATENT DOCUMENTS

| | | |
|---|---|---|
| JP | 05203826 A | 8/1993 |
| WO | WO 98/05995 | 2/1998 |
| WO | WO01/40757 A2 * | 6/2001 |

OTHER PUBLICATIONS

Vollmer, F.; Braun, D.; Libchaber, A.; Khoshima, M.; Teraoka, I.; Arnold, S. "Protein detection by optical shift of a resonant microcavity." Applied Physics Letters, 80 (21), pp. 4057-4059. Publication Date: May 27, 2002.*

Email Correspondence with Mr. Gary Leuck. Date: Apr. 10, 2010.*

Gayral, B., et al., High-Q wet-etched GaAs microdisks containing InAs quantum boxes, Applied Physics Letters, 1999, vol. 75, No. 13, pp. 1908-1910.

Armani, D., et al., Ultra-High Q toroid microcavity on a chip, Nature, 2003, vol. 421, pp. 925-927.

Chin, M., et al., Design and Modeling of Waveguide-Coupled Single-Mode Microring Resonators, Journal of Lightwave Technology, 1998, vol. 1, No. 8, pp. 1433-1446.

Chu D., et al., Observation of Enhanced Photoluminescence in Erubium-Doped Semiconductor Microdisk Resonator, Applied Physics Letters, 1995, 66 (21), pp. 2843-2845.

Kawachi, M., Silica Waveguides on Silicon and Their Application to Integrated-Optic Components, Optical and Quantum Electronics, 1990, 22, pp. 391-416.

Von Klitzing, W. et al., Tunable Whispering Gallery Modes for Spectroscopy and CQED Experiments, New Journal of Physics, 2001, vol. 3, Issue 1, pp. 14.

Chan, Issaac W.T., Gas Phase Pulse Etching of Silicon for MEMS with Xenon Difluoride, 1999, IEEE, 0-7803-5579, p. 1637.

Gerard, J.M. et al., Quantum boxes as active probes for photonic microstructures: The pillar microcavity case, 1996, Applied Physics Letters, 69, pp. 449-451.

Gorodetsky, M.K., et al., Ultimate Q of optical microsphere resonators, Optics Letters, 2996, 21, pp. 453-455.

Vemooy, D.W., et al., High-Q measurements of fused-silica microspheres in the near infrared, 1998, Optics Letters, 23, pp. 247-249.

Cai, M., et al., Observation of critical coupling in a fiber taper to a silica micro-sphere whispering-gallery mode system, 2000, Physical Review Letters, 85, pp. 74-77.

Spillane, S.M., et al., Ultralow-threshold Raman laser using a spherical dielectric microcavity, 2002, Nature, 415, pp. 621-623.

Gayral, B., et al., High-Q wet-etched GaAs microdisks containing InAs quantum boxes, 1999, Applied Physics Letters, 75, pp. 1908-1910.

Michler P. et al., Quantum dot lasers using high-Q microdisk cavities, 2001, Phsica Status Solidi B-Basic Research, 224, pp. 797-801.

Cai, M. et al., Fiber-coupled microsphere laser, Optics Letters, 2000, 25, pp. 1430-1432.

McCall, S.L., et al., Whispering-Gallery Mode Microdisk Lasers, Applied Physics Letters, 1992, 60, pp. 289-291.

Sandoghdar, V. et al., Very low threshold whispering-gallery-mode microsphere laser, 1996, Physical Review A, 54, R1777-R11780.

Djordejev, K., et al., Microdisk tunable resonant filters and switches, 2002, IEEE Photonics Technologies Letters, 14, pp. 828-830.

Rabiei Payam, W.H.S., et al., Polymer Micro-Ring Filters and Modulators, Journal of Lightwave Technology, 2002, 20, pp. 1968-1975.

Djordjev, K. et al., Vertically coupled InP microdisk switching devices with electroabsorptive active regions, 2002, IEEE Photonics Technology Letters, 14, pp. 1115-1117.

Yariv, A., Critical coupling and its control in optical waveguide-ring resonator systems, 2002, IEEE Photonics Technology Letters, 14, pp. 483-485.

Soref, R.A., et al., Proposed N-wavelength M-fiber WDM crossconnect switch using active microring resonators, 1998, IEEE Photonics Technology Letters, 10, pp. 1121-1123.

Chu S.T., et al., An eight-channel add-drop filter using vertically coupled microring resonators over a cross grid, 1999, IEEE Photonics Technology Letters, 11, pp. 691-693.

Little B.E., et al., Vertically coupled glass microing resonator channel dropping filters, 1999, IEEE Photonics Technology Letters, 11, pp. 215-217.

Offrein, B. J., et al., Resonant coupler-based tunable add-after-drop filter in silcon-oxynitride technology for WDM networks, 1999, IEEE Journal of Selected Topics in Quantum.

Little, B.E., et al., Microring resonator channel dropping filters, 1997, Journal of Lightwave Technology, 15, pp. 998-1005.

Grover R. et al., Parallel-cascaded semiconductor microring resonators for high-order and wide-FSR filters, 2002, Journal of Lightwave Technology, 20, pp. 872-877.

Yanagase, Y., et al., Box-like filter response and expansion of FSR by a vertically triple coupled microring resonator filter, 2002, Journal of Lightwave Technology, 20, pp. 1.

Krioukov, E., et al., Sensor based on an integrated optical microcavity, 2002, Optics Letters, 27, pp. 512-514.

Vollmer F., et al., Protein detection by optical shift of a resonant microcavity, 2002, Applied Physics Letters, vol. 80, No. 21, pp. 4057-4059.

Bumki, M. et al., Compact, fiber-compatible, cascaded Raman laser, 2003, Optics Letters, vol. 28, No. 17, pp. 1507-1509.

Kleppner, D., Inhibited Spontaneous Emission, 1981, Physical Review Letters, 47, pp. 233-236.

Yang L., et al., Fiber-coupled Erbium Microlasers on a chip, 2003, Applied Physics Letters, vol. 83, No. 5, pp. 825-826.

Kippenberg, S. M., et al., Fabrication and coupling to planar high-Q silica disk microcavities, 2003, Applied Physics Letters, vol. 83, No. 4, pp. 797-799.

Yang, L. et al., Gain functionalization of silica microresonators, 2003, Optics Letters, 28, pp. 592-594.

Schiller S., et al., Fused-silica monolithic total-internal-reflection resonator, 1992, Optics Letters, vol. 17, No. 5, pp. 378-380.

Knight, J.C., Phase-matched excitation of whispering-gallery-mode resonances by a fiber taper, 1997, Optics Letters, vol. 22, No. 15, pp. 1129-1131.

Yariv, A., Universal Relations for coupling of optical power between microresonators and dielectric waveguides, 2000, Electronics Letters, vol. 36, No. 4, pp. 321-322.

Little B. E., et al., Wavelength switching and routing using absorption and resonance, 1998, IEEE Photonics Technology Letters, vol. 10, No. 6, pp. 816-818.

International Search Report, PCT App. No. US03/31727, Mar. 26, 2005.

Armani, A. M., et al., Ultra-high-q microcavity operation in H2O and D20, 2005, Applied Physics Letters, 87, 151118-1-151118-3.

Armani, A.M., et al., Heavy water detection using ultra-high-Q microcavities, 2006, Optics Letters, vol. 31, No. 12, pp. 1896-1898.

Vahala K. et al., Photonic clocks, Raman lasers, and Biosensors on Silicon, Lasers & Electro-Optics Society, IEEE, 2006, pp. 40-41.

Vahala K. et al., Biological detectors using ultra-high-Q microresonators, 2006 Digest of the LEOS Summer Topical Meetings, 2006, pp. 50-51.

Armani A.M., Biological and chemical detection using ultra-high-Q toroidal microresonators, Biophysical Society 2007.

Armani A.M., et al., Heavy water detection using ultra-high-Q microcavities, 2006, OSA Frontiers in Optics 2006.

Vahala K., et al., Chemical and biological detectors using ultra-high-Q microresonators, SPIE Optics and Photonics 2006.

Armani A.M., et al., Abstract of Detection of D2O using ultra-high-Q microcavities, American Physical Society (APS) Mar. Meeting 2006.

USPTO Office Action for U.S. Appl. No. 10/678,354, Oct. 13, 2005, 16 pages.

Attorney for Applicant, U.S. Amendment in response to USPTO Office Action for U.S. Appl. No. 10/678,354, Apr. 10, 2006, 22 pages.

USPTO Office Action for U.S. Appl. No. 10/678,354, Final rejection, Feb. 12, 2007, 12 pages.

Attorney for Applicant, Response to USPTO Office Action for U.S. Appl. No. 10/678,354, and Declaration of Adam Cochran, Apr. 17, 2007, 6 pages.

USPTO Office Action for U.S. Appl. No. 10/678,354, Non-final rejection Apr. 30, 2007, 10 pages.

European Patent App. No. 03 816 213.7-2216, Office Action (Jul. 29, 2005) (8 pages).

Jacqueline C. Freeman, European Patent App. No. 03 816 217.7-2216, Response to Jul. 29, 2005 Office Action (8 pages).

European Patent App. No. 03 816 213.7-2216, Office Action (Jul. 13, 2006) (5 pages).

Jacqueline C. Freeman, European Patent App. No. 03 816 217.7-2216, Response to Jul. 13, 2006 Office Action (8 pages).

European Patent App. No. 03 816 213.7-2216, Communication Under Rule 51(4) EPC, Mar. 19, 2007 (4 pages).

Final Office Action dated Oct. 19, 2007 in U.S. Appl. No. 10/678,354, filed Oct. 2, 2003 (13 pages).

Response to Non-Final Office Action dated Jul. 30, 2007 in U.S. Appl. No. 10/678,354, filed Oct. 2, 2003 (14 pages).

Prosecution History—U.S. Appl. No. 10/678,354, filed Oct. 2, 2003: Aug. 19, 2008 Appeal Brief; Oct. 19, 2007 Final Office Action; Jul. 30, 2007 Amendment / Response (129 pages).

Prosecution History—U.S. Appl. No. 11/016,067, filed Dec. 17, 2004: Aug. 15, 2008 Non-Final Office Action (30 pages).

* cited by examiner

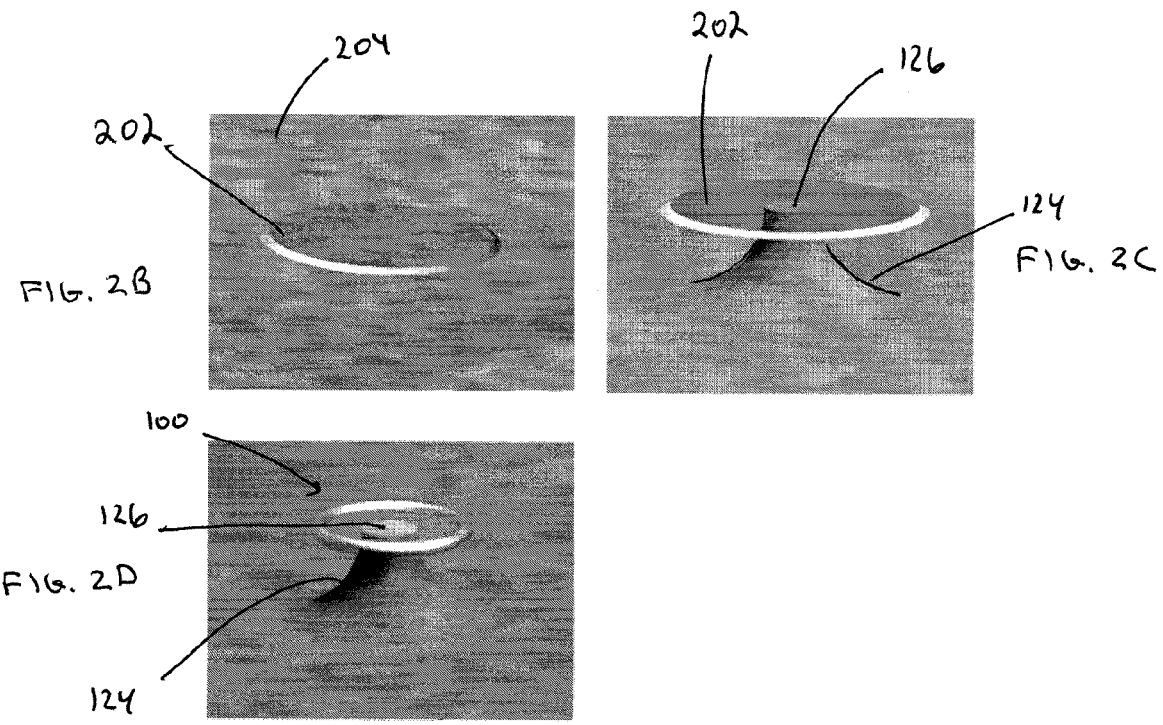

| 2801 | 2802 | 2803 |
| --- | --- | --- |
| % $D_2O$ in $H_2O$ | Experimental Q (x$10^6$) | Theoretical Q (x$10^6$) |
| 100 | 15.574 | 15.9879 |
| 90 | 4.6936 | 4.8015 |
| 80 | 2.7718 | 2.82494 |
| 70 | 1.9750 | 2.00116 |
| 60 | 1.5150 | 1.54935 |
| 50 | 1.2387 | 1.26398 |
| 40 | 1.0466 | 1.06738 |
| 30 | .915177 | .923707 |
| 20 | .803907 | .814123 |
| 10 | .712847 | .727783 |
| .01 | .653315 | .664370274 |
| 1E-3 | .647645 | .65863098 |
| 1E-4 | .646268 | .65806309 |
| 1E-5 | .645152 | .65800631 |
| 1E-6 | .644906 | .65800063 |
| 1E-7 | .644837 | .658000063 |
| 1E-8 | .645483 | .658000006 |
| 1E-9 | .644127 | .6580000063 |
| 0 | .643987 | .658000 |

Figure 28

BIOLOGICAL AND CHEMICAL MICROCAVITY RESONANT SENSORS AND METHODS OF DETECTING MOLECULES

CROSS REFERENCE TO RELATED APPLICATIONS

This application claims the benefit under 35 U.S.C. §119 to U.S. Provisional Application Ser. No. 60/790,667, filed on Apr. 10, 2006, the contents of which are incorporated herein by reference. This application is a continuation-in-part of co-pending U.S. application Ser. No. 10/678,354, filed on Oct. 2, 2003, priority of which is claimed under 35 U.S.C. §120, which claims priority under 35 U.S.C. §119 to U.S. Provisional Application No. 60/415,412, filed on Oct. 2, 2002, the contents of which are also incorporated herein by reference.

STATEMENT REGARDING FEDERALLY SPONSORED RESEARCH

The U.S. Government has certain rights in this invention pursuant to one or both of Grant No. HR0011-04-1-0032 awarded by the Defense Advanced Research Projects Agency (DARPA) and Grant No. N00014-00-1-0650 awarded by the Office of Naval Research.

FIELD OF THE INVENTION

The present invention relates to biological and chemical microcavity sensors.

BACKGROUND

Known single molecule sensors typically require a fluorescent or metallic label that is attached to the target molecule so that the target molecule can be identified. Such labels, however, require prior knowledge of the presence of the target molecule. Thus, known sensor systems that require labels are not suitable for blind detection of target molecules, which do not have labels. Further, such labels may require additional data processing. For example, sensors using labels may require ensemble averaging of large numbers of cells, thereby resulting in confusion or dulling of recorded responses in those cases in which there is any heterogeneity in the cells or their responses. As a result, detection using labels cannot be performed in real-time.

Several devices have been used for label-free detection including fiber optic waveguides, nanowires, nanoparticle probes, biochips, mechanical cantilevers and micro-sphere resonators. For example, U.S. Pat. No. 4,071,753 to Fulenwider et al. and U.S. Pat. No. 4,419,895 to Fuller describe optical fiber sensors. In such systems, the optical coupling coefficient between two fibers varies with the physical parameter to be measured, so that by measuring such coefficient, the parameter can be detected and measured. In another type of optical sensor, the physical parameter to be measured modulates the vibrational motion of a transducer. Such modulation changes the intensity of light coupled between the ends of two optical fibers so that by measuring such changes the physical parameter can be detected and measured. U.S. Pat. No. 6,583,399 to Painter et al. describes a micro-sphere resonant sensor that includes a modifier that is bound to an outer surface of the spherical resonator. The modifier provides a binding site such that a binding event occurs at the outer surface of the microsphere in the presence of a target molecule. While certain known devices may provide label-free detection, they have a number of limitations and can be improved.

Initially, various known sensors lack the sensitivity to allow detection of a very small number of molecules or a single molecule and, therefore, may not be suitable for biological and chemical analyses requiring more specific detection such as cell signaling and cellular dynamics. For example, single molecule detection capabilities are increasingly important for biologists and chemists who are working to unravel the complex nature of cell signaling and cellular dynamics, e.g., monitoring biochemical pathways at the single cell level. Single molecule detection can be used in various environmental applications. In contrast, previous experiments with silica micro-spheres, for example, demonstrated gross detection of approximately 1 billion molecules. Accordingly, such devices are not suitable for detection of a very small number of molecules or a single molecule.

The reasons for inadequate sensitivities are specific to each type of sensor. For example, sensitivities of sensors having mechanical components may be limited by the sensitivities that can be achieved given the particular mechanical construct. Mechanical resonators have demonstrated single molecule sensitivity at liquid nitrogen/liquid helium temperatures. However, such capabilities are not suitable for biological detection because molecules of interest do not exist in their nature conformations at these temperatures. Further, such devices are often subject to electromagnetic interference. In the case of certain optical sensors and traps, sensitivity limitations are due, in part, to the limited interaction of light with the target molecule. For example, in a simple optical waveguide sensor, the input light has only one opportunity to interact with the target molecule.

Various sensors also present manufacturing and integration challenges, which limit the extent to which such devices can be used on a large-scale basis. For example, known microsphere resonators are typically limited to laboratory applications and experiments as a result of their spherical shape and the fabrication controls that are needed to produce such shapes. Additionally, certain devices have been characterized in an air environment, but nearly all molecular detections are performed in a solution or liquid.

Further, in the case of optical sensors, it is necessary to increase the evanescent field intensity to increase the detection limit into the single molecule regime, which many optical sensors cannot do. Increases in evanescent field and detection sensitivity were demonstrated previously using a levitated micro-droplet resonator formed from various liquids. However, such micro-droplet resonators are not practical since they cannot be immersed in liquid and require fluorescent labels and magneto-optical traps to maintain their spherical shape.

In addition to challenges of detection a small number of molecules or single molecule, known devices also have limitations when detecting a single species in a mixture of chemically similar molecules. Several different systems and techniques have been used for this purpose including spectroscopic (emission and absorption) techniques proton conductors and nuclear magnetic resonance, but known systems and techniques also have limited sensitivities. For example, known sensors are only capable of detecting 30 parts per million per volume (ppmv) of heavy water ($D_2O$) in water ($H_2O$). Such capabilities may not be sufficient in applications requiring more sensitive heavy water detection capabilities in order to detect removal of naturally occurring heavy water from public water sources or to identify potential nuclear activities.

Accordingly, blind, label-free molecule detection methods and sensor devices having enhanced specificity and sensitivity to detect a very small number of molecules or a single molecule would be desirable. It would also be desirable to detect a single species in a mixture of chemically similar molecules. It would also be desirable to have sensors that interact with molecules more than only one time as in known various known optical waveguides. Further, it would be desirable to have label-free sensor devices that can be manufactured and implemented more easily than other devices that present manufacturing and integration challenges. It would also be desirable to have label-free detection methods and sensors in order to enable new biological, chemical, biochemical and environmental research and applications. It would also be desirable to have detection methods and sensor devices that can operate in different environments. Moreover, it would be desirable to have label-free sensors that can be functionalized to detect a small number of molecules or a single molecule of various types for use in different applications.

SUMMARY

According to on embodiment, a method of detecting at least one molecule in an environment includes introducing optical energy into a microcavity having a functionalized outer surface and detecting at least one molecule bound to the functionalized outer surface. Molecule detection is based on a thermo-optic interaction between the at least one molecule and an evanescent field extending beyond an outer edge of the microcavity and into the environment.

According to another embodiment, a method of detecting at least one molecule in an environment includes introducing optical energy into an ultra-high Q planar microcavity having a functionalized outer surface detecting at least one molecule bound to the functionalized outer surface. Detection is based on a wavelength shift of the optical energy resonating in the ultra-high Q planar microcavity.

In a further alternative embodiment, a method of detecting at least one molecule in an environment includes introducing optical energy into an ultra-high Q planar microcavity having a functionalized outer surface and detecting at least one molecule bound to the functionalized outer surface. Detection is based on a wavelength shift of the optical energy resonating in the ultra-high Q planar microcavity.

Another embodiment is directed to a resonant sensor for detecting at least one molecule in an environment. The resonant sensor includes a planar silica microcavity and a waveguide. The planar silica microcavity has a functionalized outer surface. The waveguide is positioned to couple optical energy into the planar silica microcavity, which has a sufficiently high Q value to allow detection of individual molecules bound to the functionalized outer surface based on a wavelength shift of the optical energy resonating in the planar silica microcavity.

According to another alternative embodiment, a resonant sensor for detecting at least one molecule in an environment includes an ultra-high Q planar microcavity and a waveguide. The ultra-high Q planar microcavity has a functionalized outer surface. The waveguide is positioned to couple optical energy into the ultra-high Q planar microcavity, which has a sufficiently high Q value to allow detection of individual molecules bound to the functionalized outer surface based on a wavelength shift of the optical energy resonating in the ultra-high Q planar microcavity.

A further alternative embodiment is directed to a resonant sensor for detecting at least one molecule in an environment that includes an ultra-high Q planar microcavity made of silica, a substrate and a waveguide. The ultra-high Q planar microcavity has a functionalized outer surface and a Q value of at least $10^6$. The substrate supports the ultra-high Q planar microcavity. The substrate is made a material other than silica. The waveguide is positioned to couple optical energy into the ultra-high Q planar microcavity. The Q value of the ultra-high Q planar microcavity allowing detection of individual molecules bound to the functionalized outer surface based on a wavelength shift of the optical energy resonating in the ultra-high Q planar microcavity.

In one or more embodiments, microcavity is optical energy is toroid-shaped. The Q value of the microcavity is greater than $10^6$, e.g., greater than $10^7$, or greater than $10^8$. Embodiments can detect a small number of molecules and even a single molecule using a thermo-optic interaction that results from a molecule binding to a functionalized outer surface of the microcavity, interacting with the evanescent field generated by optical energy circulating inside microcavity and heating the microcavity, thereby changing an optical property (e.g., a wavelength), of the optical energy resonating in the microcavity. Embodiments are also capable of detecting small numbers of molecules and a single molecule without the need for a fluorescent or metal label.

A further embodiment is directed to a method of detecting at least one molecule in a fluid containing a plurality of different molecules. The method includes introducing optical energy into a planar silica microcavity, exposing the planar silica microcavity to the fluid containing the plurality of different molecules and detecting the at least one molecule in the fluid based on a change of Q value of the planar silica micro cavity.

According to yet another embodiment, a resonant sensor for detecting at least one molecule in a liquid containing a plurality of molecules includes a planar silica microcavity, a waveguide a detector. The waveguide is positioned to couple optical energy into the planar silica microcavity. The detector is adapted to detect the at least one molecule in the liquid based on a change of a Q value of the planar silica microcavity when the planar silica microcavity is exposed to the target molecule in the liquid.

Another alternative embodiment is directed to a resonant sensor for detecting heavy water in a liquid and having a microcavity, a waveguide and a detector. The waveguide is positioned to couple optical energy into the microcavity, and the detector is adapted to detect heavy water in the liquid based on a change of microcavity when the microcavity is exposed to the heavy water in the liquid.

In a further embodiment, a resonant sensor for detecting heavy water in a liquid includes a planar, toroid-shaped silica microcavity having a Q value of at least $10^6$, a waveguide and a detector. The waveguide is positioned to deliver optical energy to the planar, toroid-shaped silica microcavity, and the detector is adapted to detect heavy water in the liquid based on a change of the Q value of the planar, toroid-shaped silica microcavity when the planar, toroid-shaped silica microcavity is exposed to the heavy water in the liquid.

Another embodiment is directed to a method of detecting a single molecule in an environment. The method includes introducing optical energy into a resonant microcavity, and detecting a single molecule based on a change of an optical property of the microcavity when the microcavity is exposed to a solution or liquid in the environment containing the molecule.

In one or more embodiments, the fluid is a liquid, and detection of a molecule, such as heavy water, is based on a change of Q value while a resonance wavelength of the planar silica microcavity remains substantially constant. In one embodiment, the Q value of a microcavity increases as the concentration of the at least one molecule in the fluid increases. Embodiments have enhanced sensitivities to allow detection of molecule concentrations less than 0.003%, e.g., less than 0.001%, e.g., about 0.0001%.

In one or more embodiments, the microcavity can be planar and be made of silica. Further, the microcavity can have a toroid shape and have ultra-high Q values.

BRIEF DESCRIPTION OF THE DRAWINGS

Referring now to the drawings in which like reference numbers represent corresponding parts throughout and in which:

FIG. 2B illustrates formation of a silicon dioxide disk or pad on a silicon wafer using a first etchant such as HF solution;

FIG. 2C illustrates forming silica microdisk using a second etchant such as $XeF_2$ isotropic etchant;

FIG. 2D illustrates formation of microcavity by reflowing an outer surface of the silica microdisk;

FIG. 28 is a table including experimental and theoretical values of Q value for different heave water concentrations in water;

DETAILED DESCRIPTION OF ILLUSTRATED EMBODIMENTS

Embodiments of a microcavity resonator. According to one embodiment, microcavity resonators are capable of ultra-high Q values. Another embodiment is directed to a method for fabricating an ultra-high Q microcavity resonator. The described microcavity and method provide ultra-high Q values that can be fabricated using known semiconductor and wafer processing techniques and equipment. Micro-cavities of embodiments of the invention can be fabricated in a time and cost effective manner and can also be integrated with other planar components and systems that are produced with planar fabrication techniques and equipment.

Embodiments of a microcavity resonant sensor. Micro-cavities, including toroid-shaped ultra-high Q microcavity embodiments, can be used as biological, chemical, and biochemical sensors. According to one embodiment, embodiments are capable of identifying specific molecules with enhanced sensitivity so that a small number of molecules and even a single molecule can be detected. Embodiments provide these advantages without requiring a label or a lens as used in various known single molecule sensors and optical traps.

In the following description, reference is made to the accompanying drawings, which show by way of illustration specific embodiments in which the invention may be practiced. It is to be understood that other embodiments may be utilized as various changes may be made without departing from the scope of the invention.

Figure 1A:
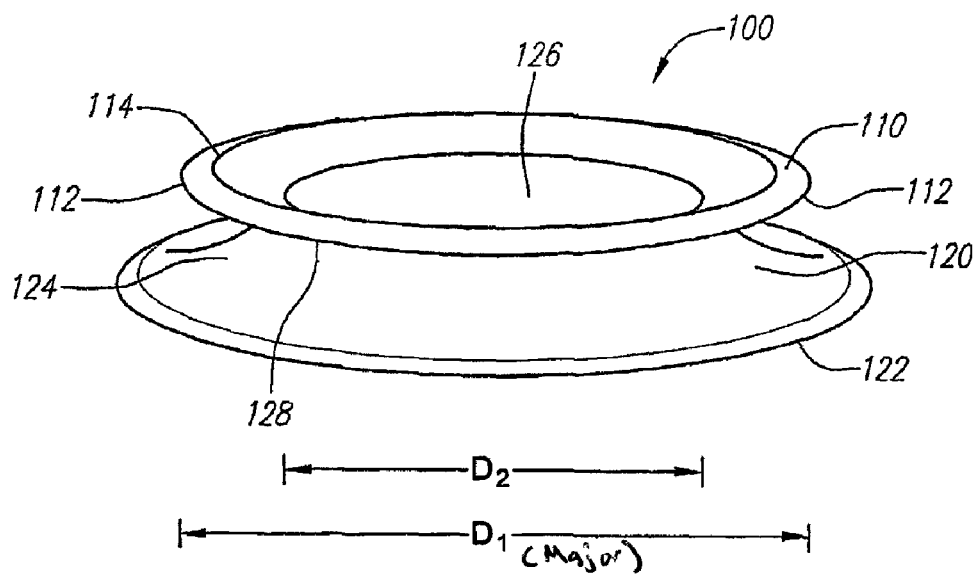
FIG. 1A is a perspective view of a microcavity according to one embodiment.
Figure 1B:
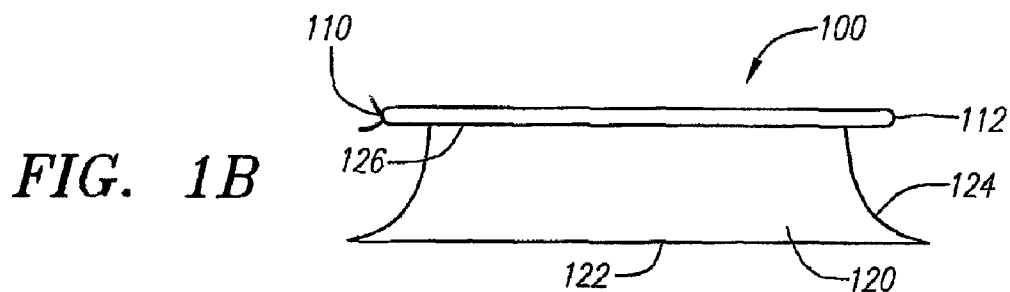
FIG. 1B is a side view of a microcavity according to one embodiment.
Figure 1C:
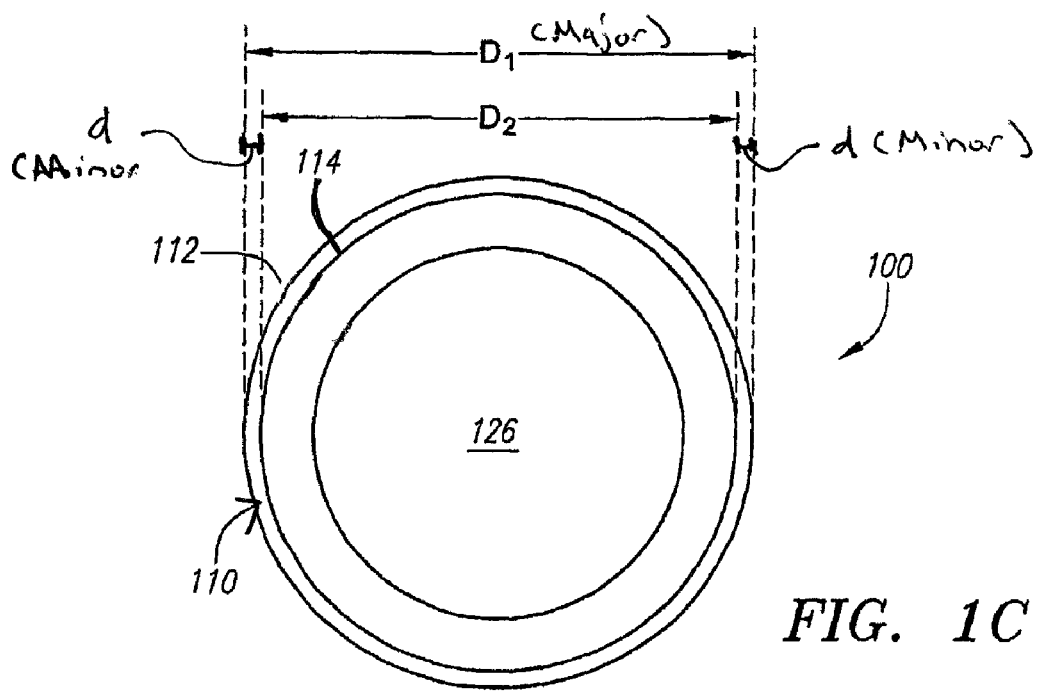
FIG. 1C is a top view of a microcavity according to one embodiment.
Figure 1D:
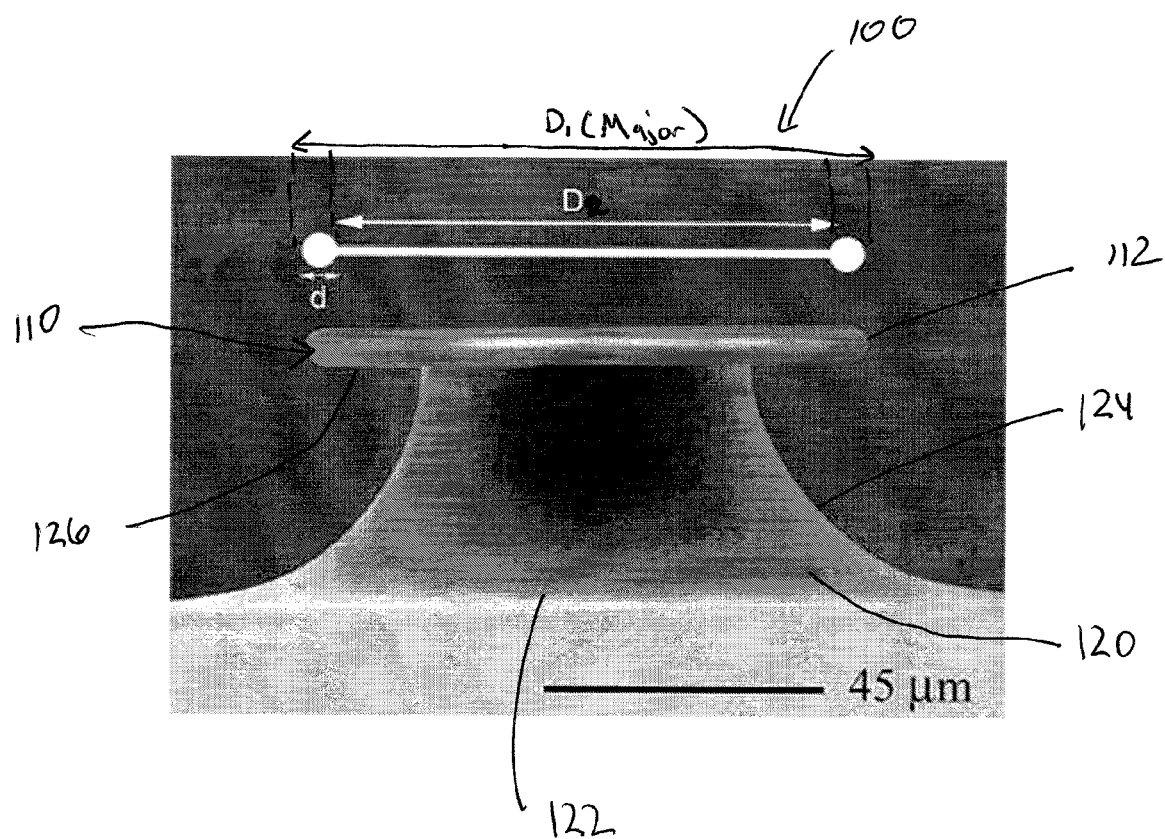
FIG. 1D is a side view of a microcavity for use in various embodiments.

Referring to FIGS. 1A-D, in accordance with one aspect of the present invention, embodiments of an ultra-high Q microcavity resonator or assembly 100 include an optical material or microcavity 110 and a substrate 120. In the illustrated embodiment, the microcavity 110 is in the form of a ring, disk or toroid has a periphery or outer edge 112 and an inner edge 114. An outer or major diameter $D_1$ is defined by the outer edges 114 of the microcavity 110, and an inner diameter $D_2$ is defined between the inner edges 112 of the microcavity. A thickness or diameter of the microcavity 110 is represented as a minor diameter d. FIG. 1D further illustrates a microcavity 110 having a major diameter $D_M$ of about 90 microns and that can be used with various microcavity sensor embodiments. The microcavity 110 can be, for example, a silica microcavity, and the substrate 120 can be, for example, a silicon substrate. With embodiments having these materials, microcavity resonator and sensor embodiments can be implemented on a silicon chip.

In the illustrated embodiment, the substrate 120 includes a bottom surface 122, a middle tapered or angled surface 124, and a top surface 126. Portions of the silicon substrate 120 that are located below the microcavity 110, e.g., below a periphery 112 of the microcavity 110, are removed so that the substrate 120 is in a form of a support pillar. In the illustrated embodiment, the inner edge 114 of the microcavity 110 extends around the outer edge of the top surface 126 of the substrate 120. Thus, the substrate 120 effectively supports and elevates the microcavity 110 above the bottom surface 122 of the substrate 120. In the illustrated embodiment, the microcavity 110 is substantially parallel to a top surface 126 of the pillar. Other non-parallel orientations may also be utilized. Optical energy travels along an inner surface of the outer edge 112 of the microcavity 110, for example, within a whispering gallery mode (WGM) or other resonant modes as needed. A WGM is a resonant mode in which optical energy electromagnetic waves are totally internally reflected, and focused by the inner surface of the microcavity 110. Thus, the optical energy can circulate within the microcavity 110 and be confined therein to provide high and ultra-high Q values.

Various factors can influence the Q value of the microcavity 110 resonation. For example, different optical materials and surface finishes can support different Q values. Q values can also change based upon the diameter of the microcavity 110. For example, in one embodiment, the diameter of a silica microcavity 110 can be from about 10 μm to about 500 μm, preferably between 15 μm to about 200 μm, and the corresponding Q values can range from about $10^4$ to about $10^9$. In one embodiment, an ultra-high Q microcavity 110 has a diameter of at least about 10 m, e.g., between about 10 and about 30 μm, and a Q value of about 500 million.

Accordingly, persons of ordinary skill in the art will recognize that the size of the microcavity 110 is one factor in providing an ultra-high Q value, and that embodiments of the invention are capable of supporting optical energy at various Q values including "high" Q values and even higher Q values, such as "ultra-high" Q values. The present invention is capable of achieving various ultra-high Q values, e.g., at least $10^6$ or one million. For example, in one embodiment, the Q value may be about $10^8$ or 100 million to about $5 \times 10^8$ or 500 million. Further, micro-cavities 110 having different shapes and sizes can have various ultra-high Q values.

A microcavity 110 according to one embodiment is capable of providing both high and ultra-high Q values as previously defined. This specification, however, refers to an ultra-high Q microcavity 110 since micro-cavities having ultra-high Q values are generally preferred and may be utilized a broader range of applications. The invention, however, is not so limited and can be utilized with both high and ultra-high Q experiments, applications and components.

Figure 2A:
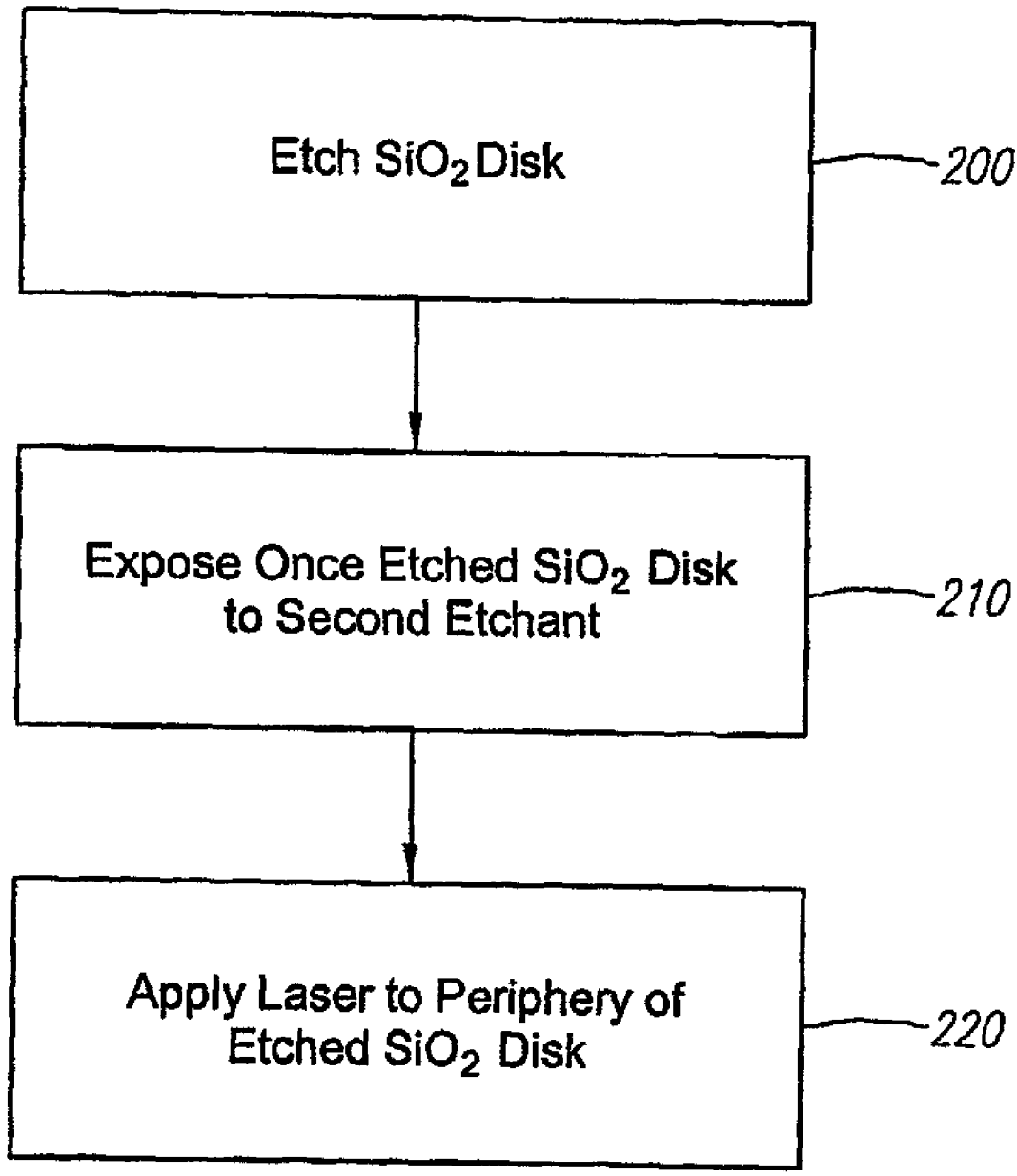
FIG. 2A is a flow diagram illustrating a method of fabricating a microcavity according to one embodiment.

FIG. 2A illustrates a method of fabricating an ultra-high Q microcavity according to the present invention, and FIGS. 2B-D illustrate formation of the microcavity. Initially, in step 200, a silica or silicon dioxide ($SiO_2$) disk or a circular pad 202 is etched, e.g. on a silicon substrate 204 (FIG. 2A), for example, with a hydrogen fluoride (HF) solution. In step 210, the silica disk 202 is exposed to a second etchant, such as xenon difluoride ($XeF_2$) gas, which removes portions of the silicon base beneath the periphery of the silica disk 202 (FIG. 2B). Xenon difluoride is an etchant with high selectivity that is currently utilized to produce, for example, Micro Electrical Mechanical Systems (MEMS) devices. In step 220, a laser, such as an Excimer or $CO_2$ laser, is applied to the undercut periphery of the silica disk 202 (FIG. 2C). As a result of the laser illumination, the periphery portions of the silica disk 202 are melted or partially or completely liquefied, and a toroid-shaped microcavity 100 is formed, as shown in FIGS. 1A-D. It is believed that the molten silica collapses and adheres to itself due to the surface tension of silica.

Figure 3:
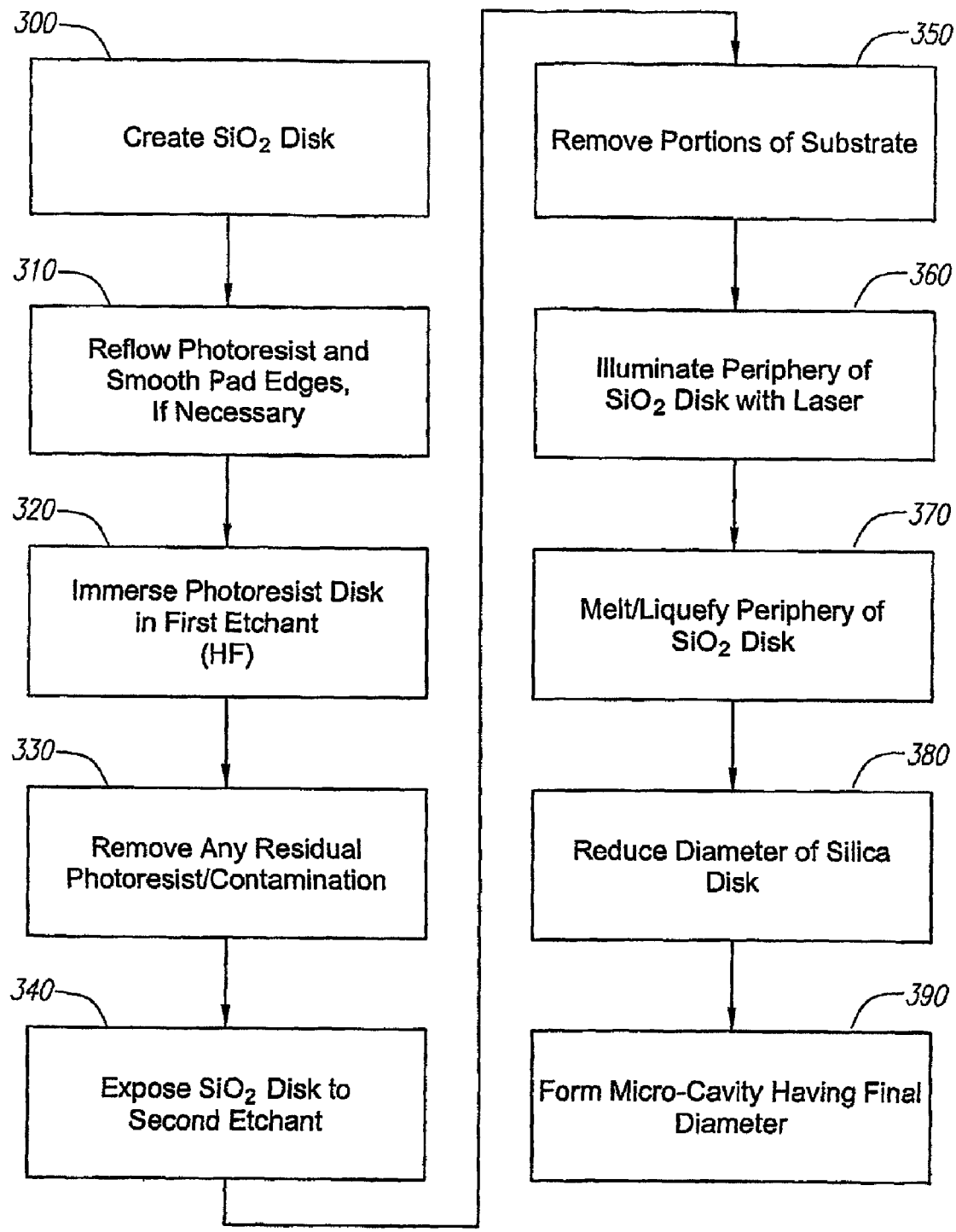
FIG. 3 is a flow chart illustrating more detailed processing steps to produce a microcavity according to one embodiment.

FIG. 3 illustrates further details of the method of fabricating a microcavity. In one embodiment, an ultra-high Q silica microcavity 110 is fabricated on a silicon substrate or wafer, preferably (100) prime grade silicon. The silicon substrate includes a thermal oxide layer having a thickness of, for example, about 2 μm or other suitable thicknesses as needed. Persons of ordinary skill in the art will recognize that other substrates can also be used depending on the etchants utilized and the particular application.

In step 300, known photolithography processing is used to create a disk-shaped photo-resist pad on the silicon substrate within an oxide layer (silica or $SiO_2$ disk). The silica disk can have a diameter of from about 10 μm to about 500 μm, preferably about 20 μm to about 200 μm, even more preferably about 160 μm. The photoresist can be heated again in step 310, if necessary, to reflow the photoresist and smooth the edges of the silica disk. In step 320, the silica disk is immersed in a first etchant. One example of a first etchant is a hydrogen fluoride (HF) etch solution, at room temperature. Buffered HF solution is another example of a first etchant. Reference is made to a HF etch solution for purposes of explanation. The silica disk acts as an etch mask when immersed in the HF solution. In step 330, residual photoresist and any organic contamination can be removed with acetone or another suitable removal agent.

Continuing with step 340, the silica disk is exposed to a second etchant. One example of a second etchant is xenon difluoride ($XeF_2$) gas at a pressure of about 3 Torr. The silica disk acts as an etch mask during exposure to the $XeF_2$ gas. As a result, in step 350, portions of the silicon substrate are removed by the $XeF_2$ gas, and the remaining portions of the silicon substrate form a pillar, which supports the larger silica disk above. The etchant used in step 340 is preferably a $XeF_2$ gas since it can selectively remove silicon. Specifically, the $XeF_2$ gas isotropically removes silicon so that the periphery of the silica disk is equally undercut, leaving a tapered silicon pillar or substrate that supports the larger silica disk. Thus, the outer edges of the silica disk extend around the outer portion of the top surface of the silicon pillar. Removing the higher index silicon from the silicon substrate also serves to inhibit power leakage from the micro-resonator into the silicon substrate.

At this stage, when the structure is a silica microdisk, whispering gallery modes (WGMs) can exist along the rim of the silica microdisk. At this stage the disk can have Q values exceeding 260,000 and can reach levels of about 3.4 million or even higher values, e.g., about 50 million. Q values of this magnitude within a resonant planar structure prepared on a silicon substrate may already surpass Q values of conventional planar resonators that are fabricated on a silicon substrate. The surface finish of the disk, however, can be processed further to provide a smoother surface finish that can support substantially higher Q values, e.g., ultra-high Q values. Specifically, the periphery of the silica disk can be melted and formed into a low loss, smooth surface, as described in the following steps 360-390.

In step 360, the periphery of the undercut silica disk is illuminated with a laser, such as a $CO_2$ laser, that emits radiation at about 10.6 micrometers. Other suitable sources of optical energy can also be utilized. The intensity profile of the $CO_2$ beam preferably follows an approximate Gaussian distribution and is focused to a diameter of approximately 200 μm. These $CO_2$ lasers are similar to lasers that are currently utilized in known before processing integrated circuit (IC) planarization.

When the outer portions of the silica disk are sufficiently heated, in step 370, they melt or are partially or completely liquefied. The silica disk periphery melts due to the temperature dependence of the silica near the 10.6 μm laser wavelength and the thermal isolation of the undercut silica disk. As a result of the high surface tension of the silica, the molten silica overcomes the forces of gravity and adheres to itself so that the laser selectively reflows the undercut periphery of the silica disk. During the silica reflow, the laser beam intensity can be varied as needed, but is typically about 100 $MW/m^2$.

In step 380, as the molten silica disk is heated with the laser, the diameter of the disk structure becomes smaller which, in turn, reduces the effective cross-section of the disk that is available to absorb power from the laser. As a result of the preceding steps, the molten silica shrinks and stabilizes into a toroid-like silica microcavity. The time required for the molten silica to assume the toroid-like shape can vary depending on, for example, the size of the disk and the amount and duration of laser radiation. For example, in one embodiment, the disk shrinks into the terminal toroid shape having a final diameter after laser radiation. Different durations of laser heating may be utilized depending on the particular materials and microcavity applications, e.g., about 1 microsecond to about 10 seconds of laser heating may be utilized. Heating can also be performed multiple times. During laser heating, the silicon pillar remains significantly cooler and physically unaffected throughout the silica reflow process, serving as a heat sink to selectively absorb and dissipate the heat generated by the reflow process. This is due to silicon having a weaker optical absorption than silica. Silicon is also about 100 times more thermally conductive than silica.

The initial diameter of the silica disk can, for example, be about 20-1000 μm. The final or terminal outer diameter of the microcavity can, for example, be about 10-700 μm. Persons skilled in the art that the diameter of the silica disk can depend on the application of the device. The minor diameter of the microcavity can have a thickness of about 1-12 μm, preferably about 4 μm. The final diameter of size of the microcavity can be limited by the size of the top surface of the silicon substrate. In other words, the molten silica disk shrinks and collapses upon itself until the inner surface of the disk shrinks around the outer portion of the top surface of the silicon pillar. Thus, the microcavity is "self-quenching" when heated and assumes the shape of a toroid as a stable state. The final diameter of the microcavity can also be further controlled by additional lithography and chemical etch steps, as needed.

The resulting toroid-shaped microcavity has smoother surfaces with an improved surface finish compared to the silica disk before the laser reflow processing. In one example, after the reflow processing, the toroid-shaped microcavity had Q values exceeding one million (ultra-high Q values), whereas the Q value of the silica disk before the laser reflow processing was about 260,000.

In one embodiment, the surface finish of the toroid-shaped microcavity has a root mean square (rms) roughness of about several nanometers. These surface finishes are similar to surface finishes of micro-sphere resonators. However, the present invention, unlike known micro-sphere resonators, provides these surface finishes and ultra-high Q values in a planar micro-resonator that can be prepared on a silicon substrate using known wafer processing and component integrating techniques. Other characteristics and technical aspects of an ultra-high Q microcavity resonator according to the present invention are described in "Ultra-High-Q Toroid Microcavity on a Chip," Nature, vol. 421, no. 6926, pp. 925-928 (Feb. 27, 2003), the disclosure of which is incorporated herein by reference.

Having described embodiments of an ultra-high Q microcavity 110 and a one manner of manufacturing a microcavity 110 utilizing laser radiation to reflow of periphery of a silica disk 202, it should be understood that various modifications to the previously described micro-resonator 100 and fabrication method can be implemented to fabricate other micro-resonators 100 capable of ultra-high Q values. For example, instead of utilizing a silica disk 202, other optical materials can be utilized to produce an ultra-high Q micro-resonator. In an alternative embodiment, the optical material may be a low melting point glass that has a melting point that is lower than silica, which has a melting point of about 1983° F.±100° F. Laser radiation can be applied to the low melting point glass to reflow the glass to form the microcavity 110. Further, both the low melting point glass and the substrate 120 (e.g. silicon substrate) can be heated together without the use of a laser. In this embodiment, the temperature is controlled so that the glass melts before the silicon substrate 120. As a result, the silicon substrate 120 maintains its integrity, and the glass is melted into the ultra-high Q microcavity 110 and can assume a toroid shape, as previously discussed. Further, other suitable materials besides silica and low melting point glass can be utilized if they possess a relatively high surface adhesion that can overcome forces of gravity. In addition, other substrates besides a silicon substrate 120 can be utilized, such as III-V substrates.

Referring again to FIGS. 1A-D, in the illustrated embodiment, the microcavity 110 has a generally circular or disk shape, e.g., a toroid or doughnut-like shape. Toroid dimensions may vary with the size of the microcavity 110. In one embodiment, the toroid has a minor diameter "d" or a thickness of about 5-10 μm. Upon reading this specification, it should be understood that micro-cavities 110 can have other shapes besides a disk or toroid-like shapes including, but not limited to, an elliptical shape, an oval or "race track" shape, partially toroid, elliptical, oval and circular shapes, and various other irregular shapes by utilizing different materials, etchants, heating/reflow temperatures, durations. This specification refers to and illustrates a toroid-shaped microcavity 110 for purposes of explanation and illustration.

Further, different radiation sources and lasers that emit radiation at different emission wavelengths may be suitable for other optical materials including, but not limited to, Excimer lasers. The laser can also be applied to different portions of the periphery of the silica disk 202 for different periods of time and patterns for various degrees of reflow or to produce micro-cavities 110 of different shapes. For example, as previously discussed, the laser can be applied to the silica disk 202 so that it reflows and adheres to itself and consistently shrinks to its terminal diameter. The laser, however, can also be applied to the silica disk 202 for smaller amounts of time. In these instances, the diameter of the silica microcavity 110 would be smaller than the initial diameter, but larger than the terminal diameter. In yet a further alternative embodiment, once heating of the silica disk 202 has begun, the reflow process can be interrupted prior to quenching of the silica disk 202 and forming a toroid shape. In this instance, the microcavity 110 would also have a smaller diameter than the terminal toroid diameter.

The laser or other heat source can also be applied to selected sections of the silica disk 202 for different amounts of time to produce micro-cavities 110 of different shapes and sizes. As a result, only the heated sections may become smaller, thereby resulting in an elliptical or irregularly shaped microcavity. Accordingly, a microcavity 110 having toroid shape having a terminal diameter (FIGS. 1A-D) is illustrative of an example of an ultra-high Q microcavity 110. The invention, however, is not so limited.

Figure 4A:
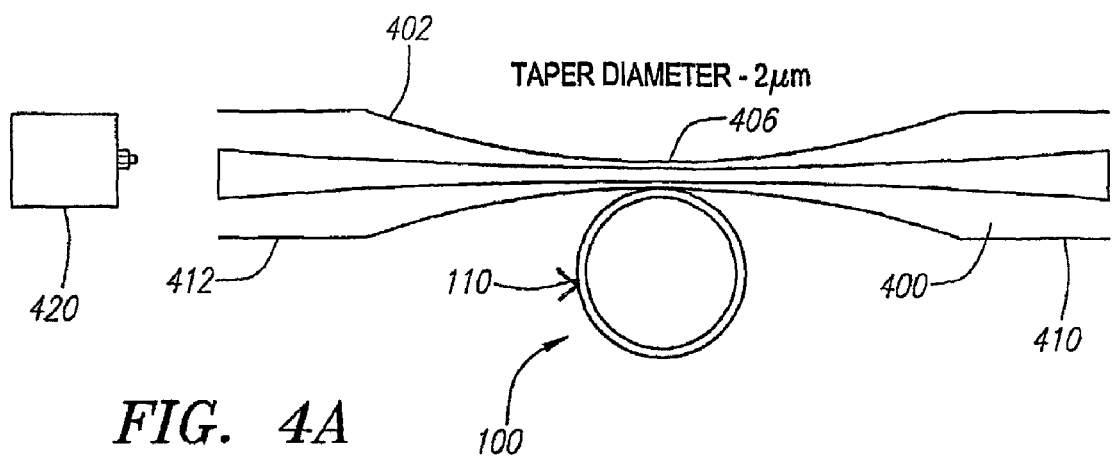
FIG. 4A is a schematic view of a fiber taper coupler or waveguide in contact with a microcavity.

One manner in which light stored in an ultra-high Q microcavity resonator 100 is coupled to a transmission media, waveguide or coupler is illustrated in FIGS. 4A-D. Transmission media 400 is utilized to carry optical energy stored in the microcavity 110. Active media, which are excited by optical pumps can also be associated with the micro-cavities 110 to facilitate the lasing of a signal within a frequency band of interest. In one embodiment, the transmission media 400 is a fiber waveguide, preferably a tapered waveguide as shown in FIG. 4A, although other waveguide configurations can also be utilized. One suitable tapered fiber waveguide is described in U.S. Pat. No. 6,741,628 to Painter et al., the contents of which are incorporated herein by reference. Tapered sections 402 and 404 and the intermediate waist region 406 of the waveguide 400 may be provided, as is known, by stretching a fiber (e.g., a single mode fiber) under controllable tension as it is softened by one or more fixed or movable heat sources (e.g., torches). The ultra-high Q microcavity 110 is coupled to the externally guided power about the waist region 406 of the fiber 400. Commercially available machines can be used for this purpose in production environments. Taper waist 406 diameters are typically several microns, preferably about two microns. The diameter of the waist region can be adjusted to properly phase-match to the ultra-high Q microcavity resonator. Other discussions and details of such taper couplings can be found in U.S. application Ser. No. 09/454,719, entitled "Resonant Optical Wave Power Controlled Devices and Methods," filed Dec. 7, 1999, the disclosure of which is incorporated by reference herein.

The consequent reduction in diameter of about one or more orders of magnitude reduces the central core in the core/cladding structure of the optical fiber 400 to vestigial size and function. As a result, the core no longer propagates a majority of the wave energy. Instead, without significant loss, the wave power in the full diameter fiber 400 transitions into the waist region 406, where power is confined both within the attenuated cladding material and within a field emanating into the surrounding environment. After propagating through the waist region 406, exterior wave power is recaptured in the diverging tapered region and is again propagated with low loss within the outgoing fiber section 410.

An optical pump 420 is optically connected to a first end 412 of the fiber 400. The optical pump 420 transmits a signal along the waveguide and to the ultra-high Q microcavity resonator 100 through the fiber taper. One or more excited laser signals in the ultra-high Q microcavity resonator 100 are then communicated to the fiber waveguide 400. The microcavity 110 recirculates the energy with low loss in, for example, a whispering gallery mode (WGM), or other resonant mode, returning a part of the power to the waveguide 400 at the waist 406.

Figure 4B:
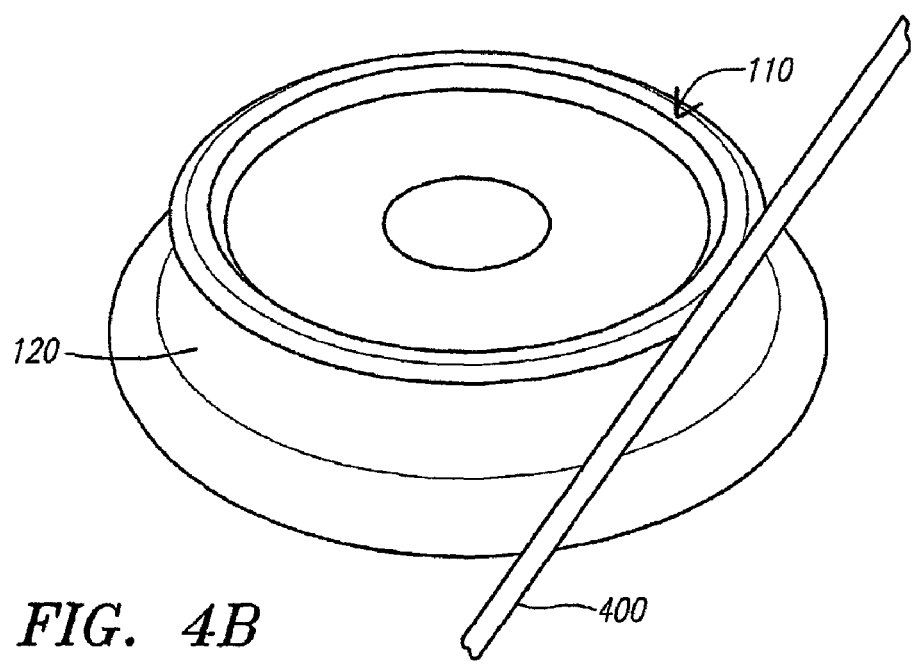
FIG. 4B is a perspective view of a fiber-taper waveguide coupled to a microcavity.
Figure 4C:
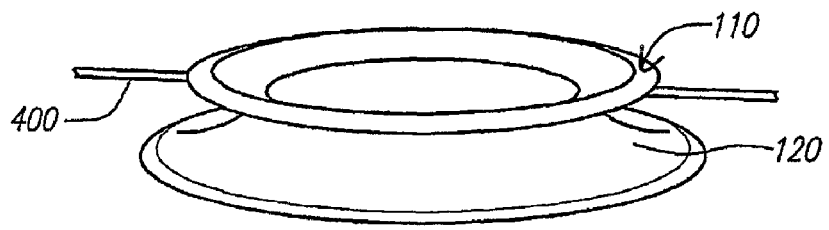
FIG. 4C is a side view of a fiber-taper waveguide coupled to a microcavity.
Figure 4D:
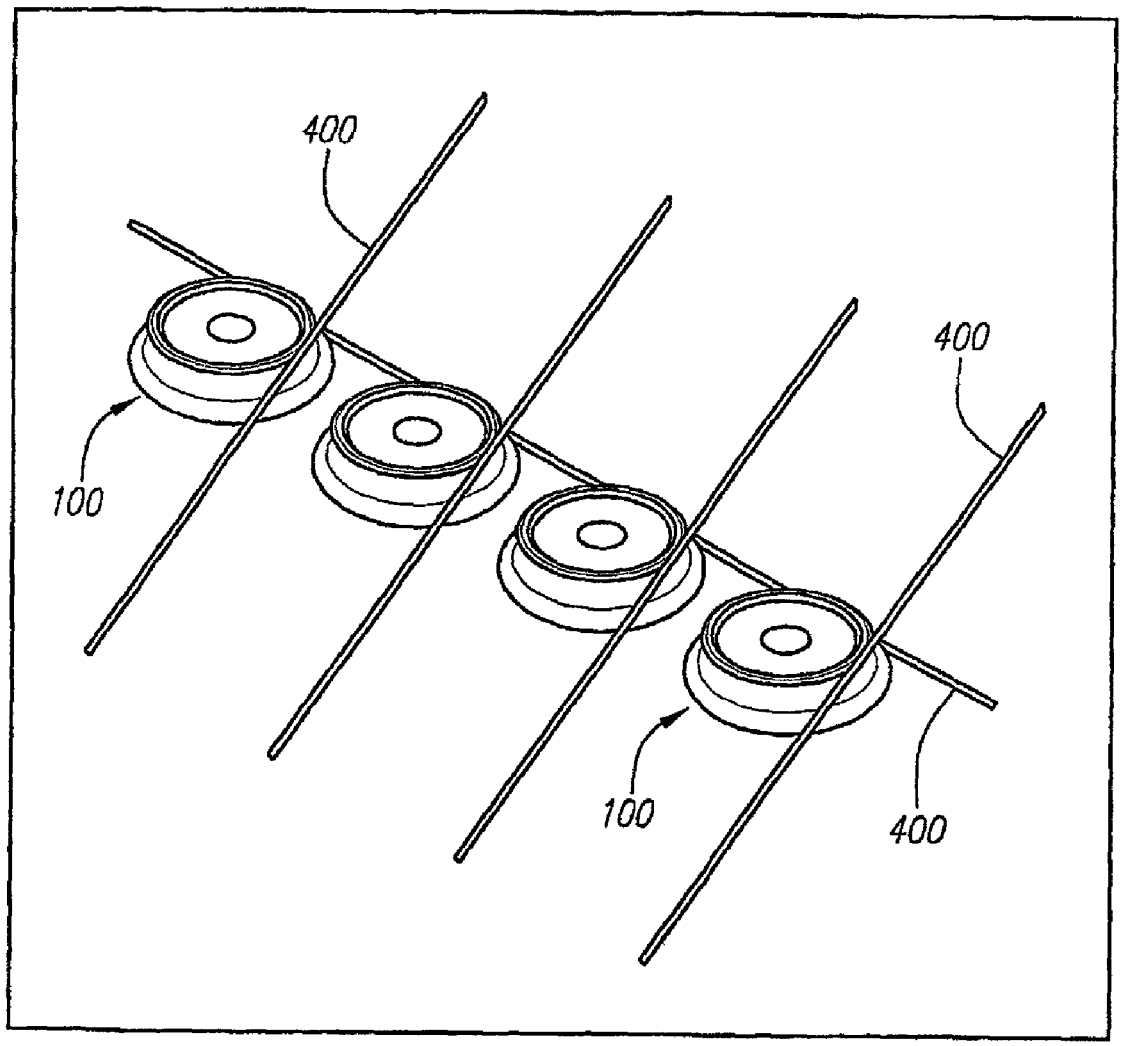
FIG. 4D is a perspective view of plurality of micro-cavities coupled to tapered fiber-taper waveguides.

When a resonance exists at the chosen wavelength, the ultra-high Q microcavity 110 functions with effectively total internal reflection and with minimal internal attenuation and radiative losses. However, the emanating portion of the wave power is still confined and guided, so it is presented for coupling back into the waveguide waist 406. These fiber coupling techniques can be used to couple a single tapered fiber to a single ultra-high Q micro-resonator 100, as shown in FIGS. 4B and 4C. Alternatively, a plurality of tapered fibers can be coupled to a plurality of micro-resonators 100, for example, as part of a circuit or to integrate with other components, as shown in FIG. 4D.

In one study, the mode structure and Q value of toroid-shaped micro-cavities 110 were characterized in an optical telecommunication band (1500 nm band). Tapered optical fibers 400 (as previously discussed) were coupled to a single-mode, tunable, external-cavity laser to efficiently excite whispering gallery modes of the ultra-high Q micro-cavities 110. Tapered waveguides were positioned on a 20 nm resolution stage and could be moved freely over the sample to individually couple to each of the toroid-shaped micro-cavities 110. Dual microscopes were used to simultaneously image the micro-cavities 100 and fiber 400 tapers from the side and the top. In order to achieve proper alignment, the taper axis was adjusted to reside in the equatorial plane of the toroidal microcavity 110 with minimal tilt angle. Critical coupling or the resonant transfer of all optical waveguide power into the microcavity 110, was achieved by adjusting the gap between the taper and the microcavity 110. Low non-resonant losses were observed (e.g., <5%).

Figure 5A:
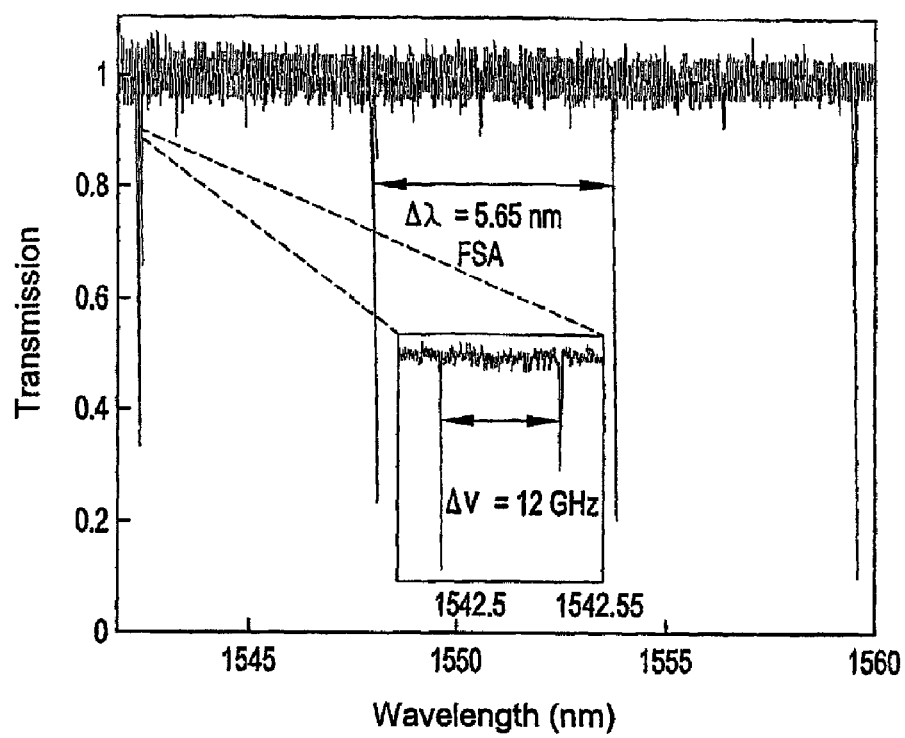
FIG. 5A is a graph illustrating transmission spectra and free spectral range of a microcavity.
Figure 5B:
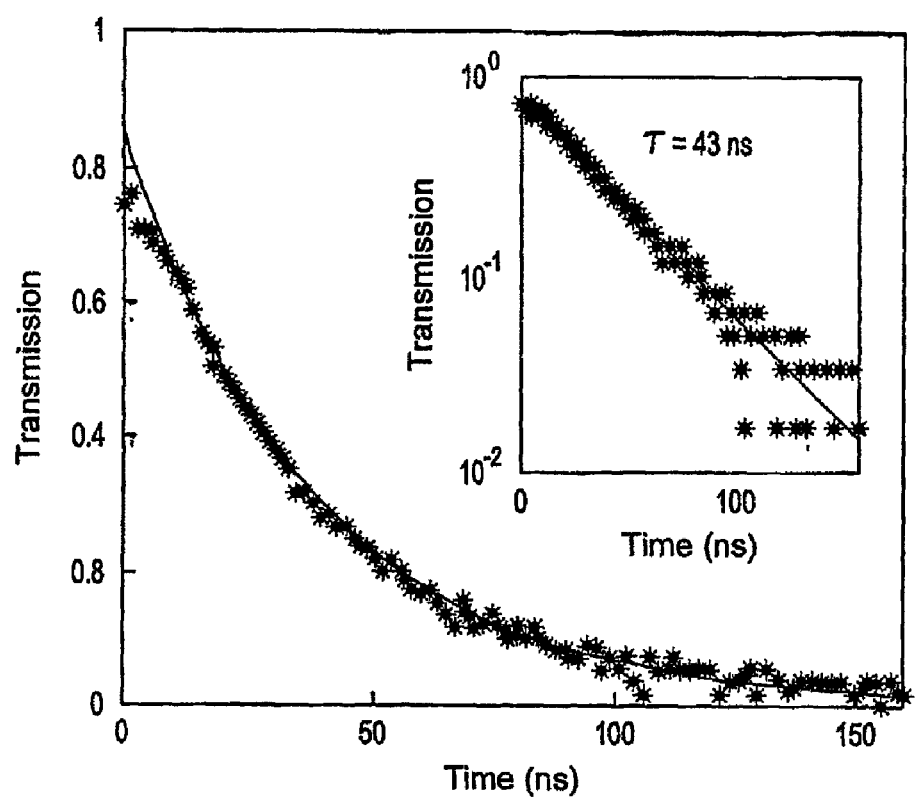
FIG. 5B is a graph illustrating a ringdown measurement of a microcavity.

FIGS. 5A and 5B illustrate graphs showing optical characteristics of two ultra-high Q micro-cavities 110 according to embodiments of the present invention. FIG. 5A shows the transmission spectra through a taper in close proximity (on the order of hundreds of nanometers) to a 94 μm diameter toroidal microcavity 100 according to an embodiment of the present invention. The observed free spectral range (FSR) corresponds to the equatorial mode number (1-index, which in this case is >270). The microcavity 110 having a FSR of about 1 nm to about 100 nm. As shown in the inset of FIG. 5A, the microcavity 110 also supports at least two azimuthal (m-index or transverse) modes. The microcavity 110 can also be configured to have differential azimuthal modes of about 12 GHz. Alternatively, the microcavity 110 can be configured to have a single radially and transversely supported mode.

The Q value of the micro-cavities 110 was measured in two ways. First, the full-width half-maximum of the Lorentzian-shaped resonance in the undercoupled regime was directly measured by scanning a single-mode laser (short-term linewidth about 300 kHz) through a resonance. Low input power levels (typically less than 5 microwatts) were used to avoid thermally-induced distortion of the line shape due to resonant-field buildup within the cavity. Repeated measurements on samples fabricated with various radii (80-120 micron) and tori thickness (5-10 micron) yielded Q values in excess of 100 million (108), whereas previous known planar micro-resonators fabricated by wafer-scale processing typically have Q values as much as four orders of magnitude lower.

Referring to FIG. 5B, data from a typical ringdown measurement is provided for a microcavity 110 according to the present invention having a diameter of about 90 μm. As an independent and more precise measurement of the Q value, the photon lifetime was directly measured by cavity ringdown. In particular, ringdown measurements are immune to the thermal effects described above. This was done by repeatedly scanning the laser into resonance with a mode that was critically coupled to the taper. As the laser scanned into resonance, power transfer increased until maximal "charging" of the resonant mode was attained. At this moment, the laser input was gated "off" by use of a high-speed, external modulator and cavity ringdown is observed as the resonant power discharges. Because the microcavity 110 is by necessity loaded during this measurement, the observed ringdown time yields the loaded Q-factor at the critical point (not the intrinsic Q).

At time t=0 in FIG. 5B, a signal is applied to "gate" the laser off. When the laser input is fully off, the detected power is due entirely to the cavity discharge field. The solid line represents an exponential fit as expected for decay of a single cavity mode. The inset shows a logarithmic plot to infer the cavity lifetime. The loaded lifetime in this structure was 43 ns. As a further check on this time constant, after gating of the pump laser the waveguide power has dropped to 80% of its predicted maximal value based on extrapolation of data to t=0. This value is consistent with the gating delay of the ringdown setup (approximately 8 ns). In particular, using the observed mode-lifetime of $\tau$=43 ns yields $e^{31 \Delta/\tau}$~83.

Loading by the taper waveguide and the excitation of the counter-propagating mode due to scattering centers intrinsic to the resonator (described by a dimensionless intermode coupling parameter F) are accounted for when inferring the intrinsic cavity Q value. The techniques used to measure this parameter in ultra-high-Q taper-coupled resonators 100 are described in various references.

For the mode shown in FIG. 5B, the intermode coupling was measured to be approximately 1, giving rise to a weak counter-propagating wave excitation (17% of the cavity buildup field is stored in the counter-propagating mode at critical coupling). In the presence of intermode coupling the relationship between the critically-coupled and the intrinsic (unloaded) cavity Q becomes, $Q_0=\omega\tau_0=.\omega\tau_{crit}(1+\{$square root$\}\{(1+\Gamma_2)\})$. This yields an intrinsic cavity Q of $1.25 \times 10^8$ inferred from cavity ringdown. This value is consistent with the measurements of the frequency line shape described above.

In yet a further alternative embodiment, the silica ring 202 can have a treated surface (such as a biotinlynated surface), a dopant or an embedded active optical component that may alter or functionalize the operation of an ultra-high Q microcavity resonator 100. For example, in one embodiment, the silica ring 202 is doped with erbium. In a further alternative embodiment, the silica ring 202 includes an embedded active component, such as erbium. Persons of ordinary skill in the art will recognize that other dopants and components can be utilized depending on the desired microcavity 110 characteristics and functions. The ultra-high Q microcavity 110 can also include a coating, such as a chemical or biologically active substance, to functionalize the microcavity 110 surface.

Figure 6:
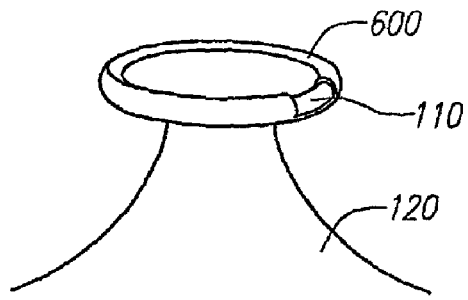
FIG. 6 is a perspective view of a microcavity that is coated with a sol-gel film and coupled to a fiber.

In one embodiment, as shown in FIG. 6, the ultra-high Q microcavity 110 is coated with an doped sol-gel film 600, such as an erbium-doped sol-gel film. Sol-gel is a colloidal suspension of silica particles that is gelled to form a solid. Various commercially available sol-gel films can be doped with erbium. The Er+3 concentration in the sol-gel layer or film 600 can be from about $0.1 \times 10^{16}$ to about $10^{20}$, preferably about $10^{19}$ $cm^3$. Other characteristics and technical aspects of a suitable sol-gel film 600 are described in "Gain Functionalization of Silica Microresonators," Optics Letters, vol. 28, no. 8, pp. 592-594 (Apr. 15, 2003), the disclosure of which is incorporated herein by reference.

Figure 7A:
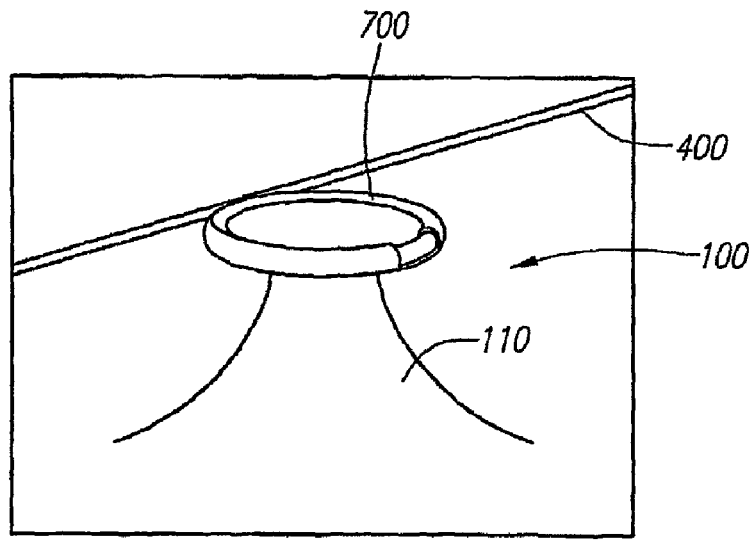
FIG. 7A is a perspective view of a fiber-taper waveguide coupled to the coated microcavity.
Figure 7B:
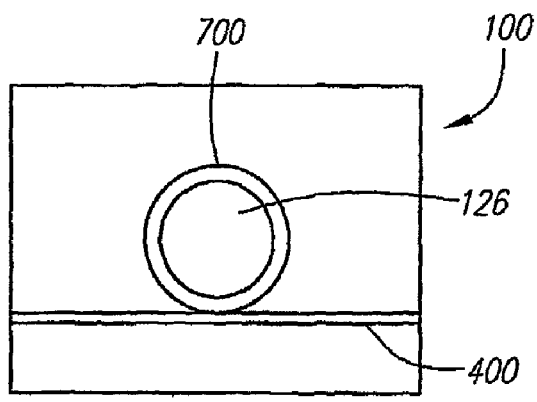
FIG. 7B is a top view of a fiber-taper waveguide coupled to the coated microcavity.

In one implementation, the silica micro-cavities 110 are immersed in the sol-gel solution for about three to five hours, and then heated at about 160° C. for about 10 hours. The micro-cavities 110 are then irradiated with a $CO_2$ laser, again at about 10.6 μm, in order to reflow and densify the sol-gel film 600. As a result of the laser radiation, the sol-gel is selectively reflowed and densified at the periphery of the microcavity 110. Referring to FIGS. 7A-B, a fiber-taper waveguide 700 can be coupled to the coated ultra-high Q micro-resonator, as previously described.

Figure 8A:
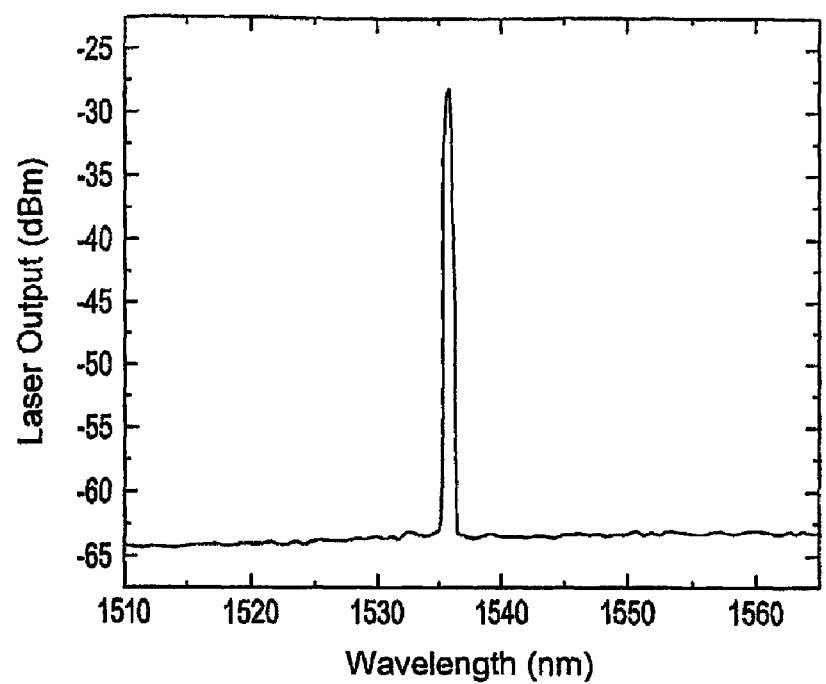
FIG. 8A is a graph illustrating laser emission spectrum and output power from an erbium-doped sol-gel coated microcavity.
Figure 8B:
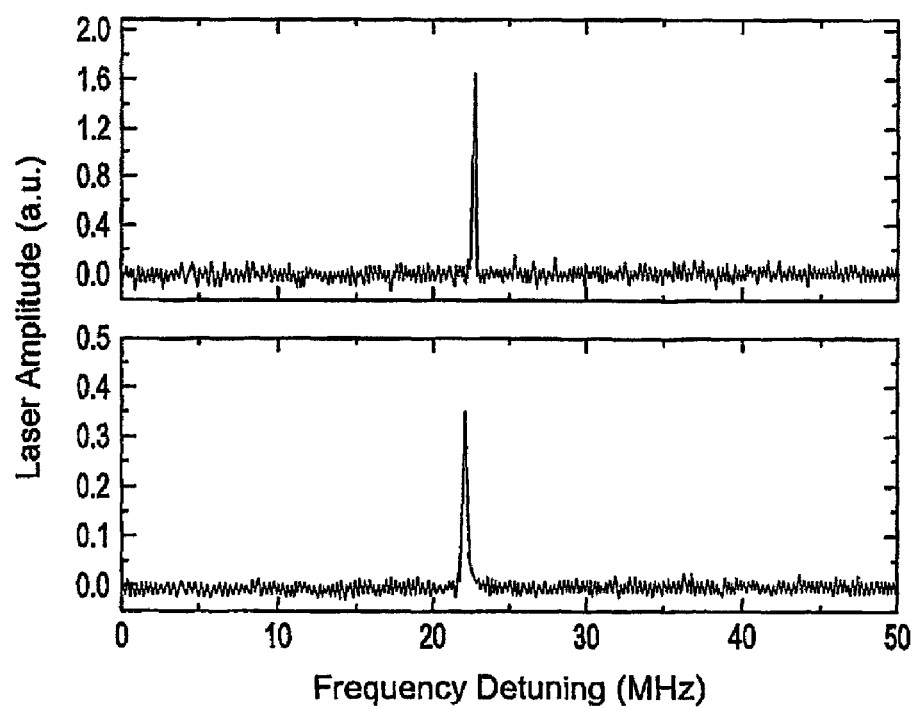
FIG. 8B is a graph comparing a reference laser with the output of an erbium-doped sol-gel coated microcavity.
Figure 8C:
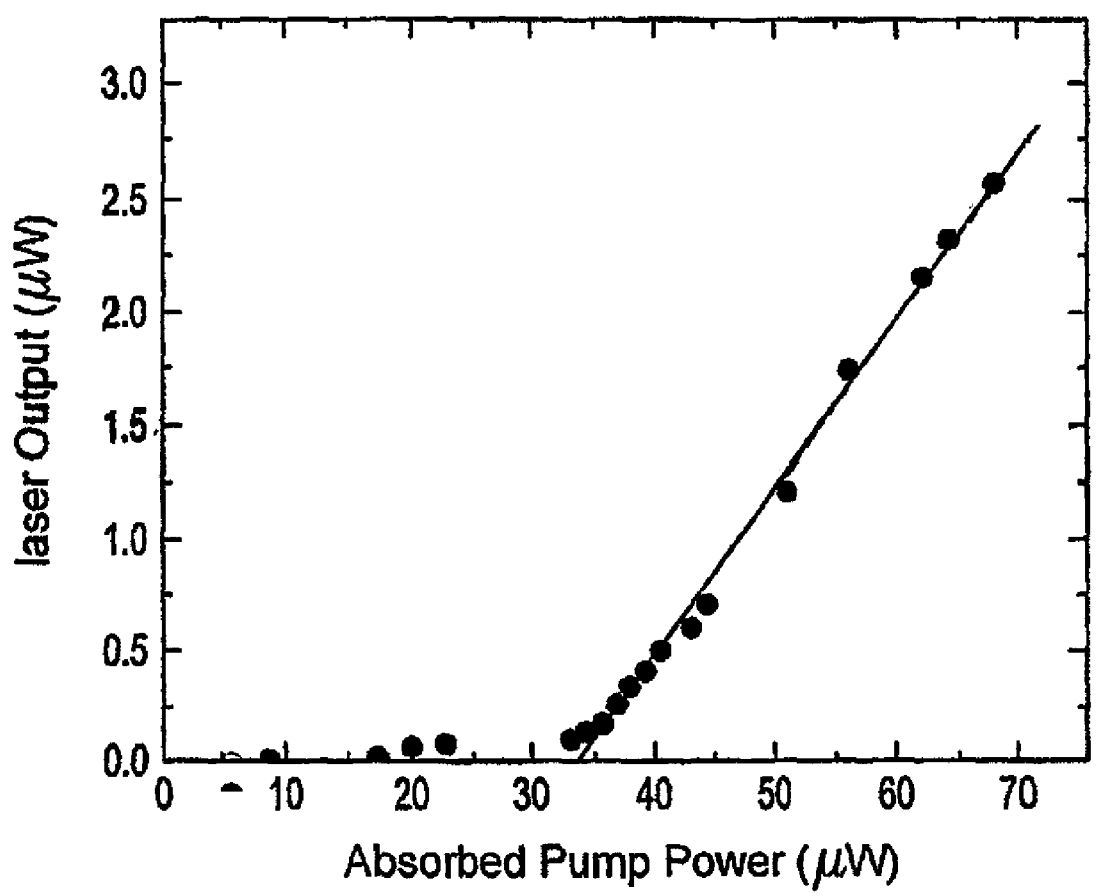
FIG. 8C is a graph illustrating laser output power versus absorbed pump power.

FIGS. 8A-C illustrate the optical characteristics of a toroid micro-resonator 110 that includes an erbium-doped sol gel coating 600 prepared and applied according to the previously described method. Specifically, FIG. 8A is a graph that illustrates the emission spectrum of the sol-gel coated microresonator that is measured utilizing a high finesse scanning Fabry-Perot spectrometer. FIG. 8B shows the spectra of a reference laser emission spectrum from a 1550 nm single mode laser with short term linewidth of 300 kHz and the emission of the erbium-doped sol-gel coated microcavity. FIG. 8C illustrates the measured laser output versus the absorbed pump power for a micro-resonator having a diameter of about 80 micrometers. Other characteristics and technical aspects of an erbium-doped sol-gel coating suitable for use in the present invention are described in "Fiber-coupled Erbium Microlasers on a Chip," Applied Physics Letters, Vol. 83, Number 5, p. 825 (Aug. 4, 2003), the disclosure of which is incorporated herein by reference.

The previously described embodiments of an ultra-high-Q planar micro-resonator 100 can be fabricated on a chip, such as a silicon chip, or other suitable substrates 120. The combination of the planar configuration of the microcavity 110 and ultra-high Q values enables these resonator devices to be efficiently and consistently processed with known wafer processing techniques. Further, the large transparency window of silica enables these devices to be utilized in various photonics applications, as well as in fundamental studies. Doping and coating an ultra-high Q microcavity 110 provides further enhancements. Electrical functionality can also be introduced to integrate control functions with the ultra-high-Q microcavities 110. For example, the ultra-high Q microcavity can serve as atomic traps on a chip for chip-scale integration of cQED experiments and related devices.

The ultra-high Q micro-resonators 100 of embodiments of the present invention are flexible and adaptable for use in various applications. For example, the resonators can be used in telecommunications and environmental/chemical/biological sensing system, particularly sensing applications that require the high degree of sensitivity provided by the ultra-high Q micro-resonators of the present invention. Aspects and applications of micro-cavities, such as ultra-high Q micro-cavities 110, for use as biological, chemical and biochemical resonant sensors or detectors are described with reference to FIGS. 9-31C.

According to one embodiment, a label-free microcavity resonant sensor has enhanced sensitivities to allow detection and discrimination of a small number of specific molecules, even a single, specific molecule. According to one embodiment, a microcavity has a functionalized outer surface that allows binding of specific type or species of molecule and has sufficiently high sensitivity so that individual or single molecules can be detected. Enhanced sensitivities are achieved using external, e.g., evanescent, optical fields having increased intensities as a result of micro-cavities having sufficiently high Q values (e.g., ultra-high Q values greater than $10^7$ and greater than $10^8$) to advantageously expand detection limits into the single molecule regime. Embodiments having a functionalized outer surface allow multiple and continuous interactions between a target molecule bound to the outer surface and the evanescent field having increased intensity. This interaction triggers a thermo-optic effect in which the bound molecule heats the microcavity which, in turn, results in a pronounced shift of the resonant wavelength of the microcavity. In these embodiments, the Q value may or may not change when the resonant wavelength changes, e.g., depending on the size of the molecule or absorption of optical energy by the molecule.

According to another embodiment, a microcavity resonant sensor is used to detect individual molecules or individual molecules of a species in a mixture of molecules based on a change of Q value of the microcavity. In these embodiments, the microcavity does not require a functionalized surface and is not based on a shift of resonant wavelength.

Figure 9:
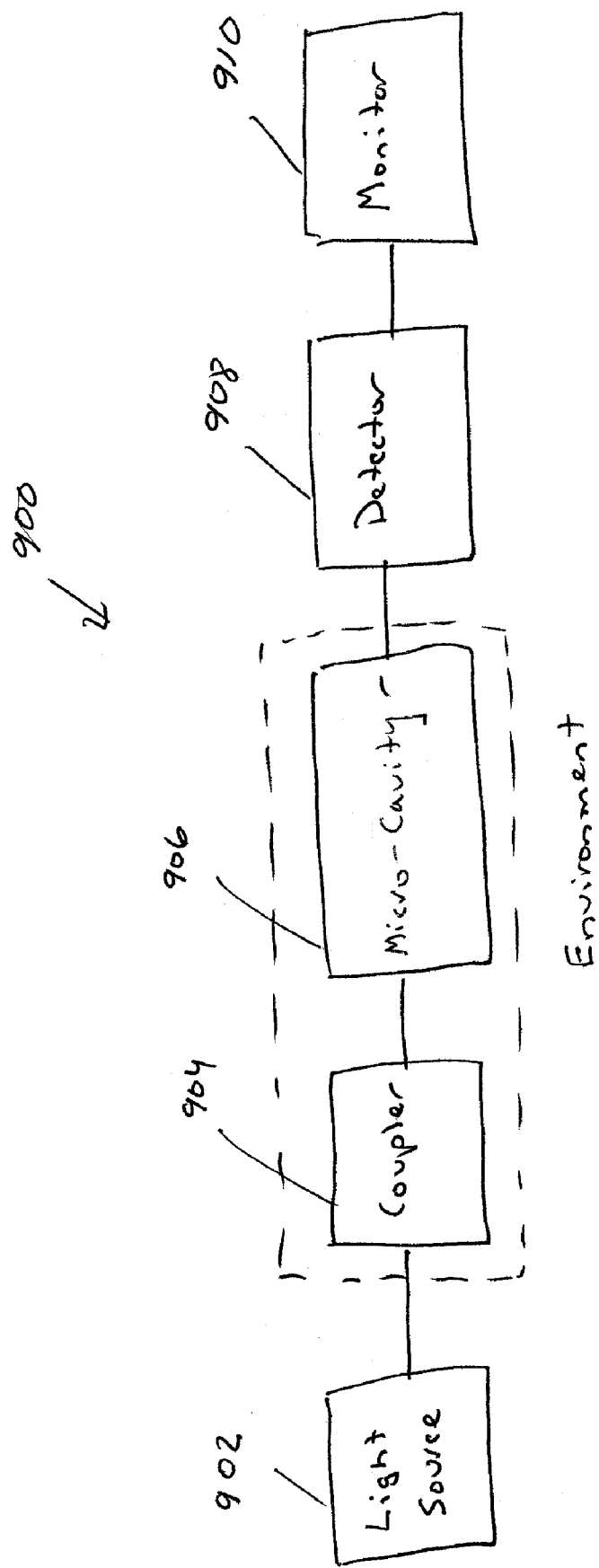
FIG. 9 is a schematic illustration of an embodiment of a resonant sensor according to one embodiment.

FIG. 9 illustrates a resonant sensor or resonant sensor system according to one embodiment that is capable of detecting small numbers of molecules, even a single molecule, without the use of labels. FIGS. 10-26B illustrate label-free micro-cavities having functionalized surfaces for use in detecting molecules based on resonant wavelength shifts and test results demonstrating advantages of embodiments over known optical sensors. FIGS. 27-31C illustrate label-free micro-cavities for use in detecting molecules, e.g., a species within a mixture of molecules (e.g. heavy water within water) based on a change of Q value and test results demonstrating advantages of embodiments over known sensors. The sensor or sensor system 900 configuration illustrated in FIG. 9 can be used with embodiments described with reference to FIGS. 10-26B that detect molecules based on resonant wavelength shifts and with embodiments described with reference to FIGS. 27-31C that detect molecules based on changes of Q value.

Referring to FIG. 9, a resonant sensor or sensor system 900 includes a light source 902, a coupler 904 adapted to receive light from the light source 902, a microcavity or micro-resonator 906 (generally referred to as "microcavity 906") that is optically coupled to the coupler 904, and one or more detectors 906 (one detector is shown) adapted to observe light that exits from the microcavity 906. During use, light is introduced into the coupler 904 from the light source 902, and the resonator 906 is placed in proximate relation to the coupler 904 such that a portion of the light passing through the coupler 904 is coupled (e.g. evanescently coupled) into the resonator 906. Embodiments can be implemented using various couplers 904 and micro-cavities 906. The coupler 904 and microcavity 906 may be individual components that are positioned when the sensor 900 is to be used, or they may be part of a manufactured package of components (represented by dotted line).

Light that is coupled into the microcavity 906 circulates within the microcavity 906 in one or more resonant modes for a period of time determined by the Q-factor of the microcavity 906. A portion of the light exits the microcavity 906 into the environment, and another portion of the light exits the microcavity 906 into the coupler 904. The detector 908 is adapted to observe the light exiting the microcavity 906 and can generate a signal or output that indicates a change of resonant wavelength and/or Q value of the microcavity 906, which can be provided to a suitable monitor 910.

One suitable coupler 904 that can be used with embodiments is illustrated in FIGS. 4A-B. The coupling portion or waist 406 of the optical fiber waveguide 400 can, for example, be about 300-1600 nm. The dimension of the waist 406 may depend on the wavelength of the light emitted by the light source 902. Further details regarding a suitable fiber taper coupler are also provided in U.S. Pat. No. 6,741,628 to Painter et al., the contents of which were previously incorporated herein by reference. Other suitable couplers 904 that can be used include a ridge waveguide, a slab waveguide, a D-fiber waveguide, a cylindrical taper waveguide, or an elliptical taper waveguide.

According to one embodiment, the microcavity 906 is a toroid-shaped micro-resonator 100 having a reflowed outer surface (e.g., as shown in FIGS. 1A-D). Embodiments can be implemented using other micro-cavities, but for purposes of explanation and illustration, this specification refers to a biological or chemical resonant sensor including a toroid-shaped microcavity 100. However, it should be understood that microcavity sensor 900 embodiments are not limited to toroid-shaped micro-cavities 100 or silica micro-cavities, and other micro-cavities and micro-cavities made of other materials having sufficiently high Q values can also be utilized.

Figure 10:
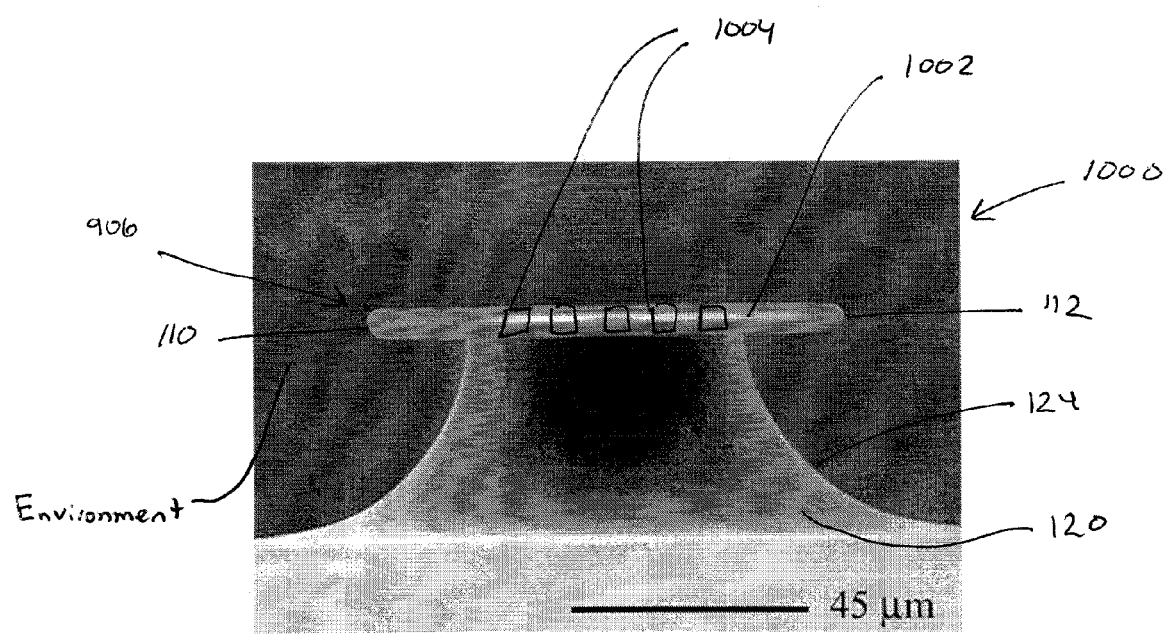
FIG. 10 illustrates the microcavity shown in FIG. 1D including a functionalized outer surface according to one embodiment.

Referring to FIG. 10, according to one embodiment, a label-free microcavity resonant sensor 1000 includes one or more functionalization elements 1004 that are applied or bound to an outer surface 1002 of a microcavity 906. Functionalization elements 1004, such as one or more chemically or biologically active substances, can be applied to the outer surface 1002 as discrete elements so that they partially or fully cover or coat the outer surface 1002. Alternatively, a sufficient number of discrete functionalization elements 1004 can be applied to the outer surface 1002 to form a functionalization coating. The functionalization elements 1004 can be applied or bound to the outer surface 1002 of the resonator 906 in different ways, e.g., electrostatically or covalently. Further, the functionalization element can be applied or bound through different mediums (e.g., liquid or gas). The functionalized outer surface 1002 is used to selectively detect specific target molecules based on a change of resonant wavelength of the microcavity 906 when the target molecules bind to the functionalization element 1004. Embodiments have increased sensitivities to allow detection of a very small number of target molecules, even a single target molecule, without the need for fluorescent or metal labels.

Figure 11:
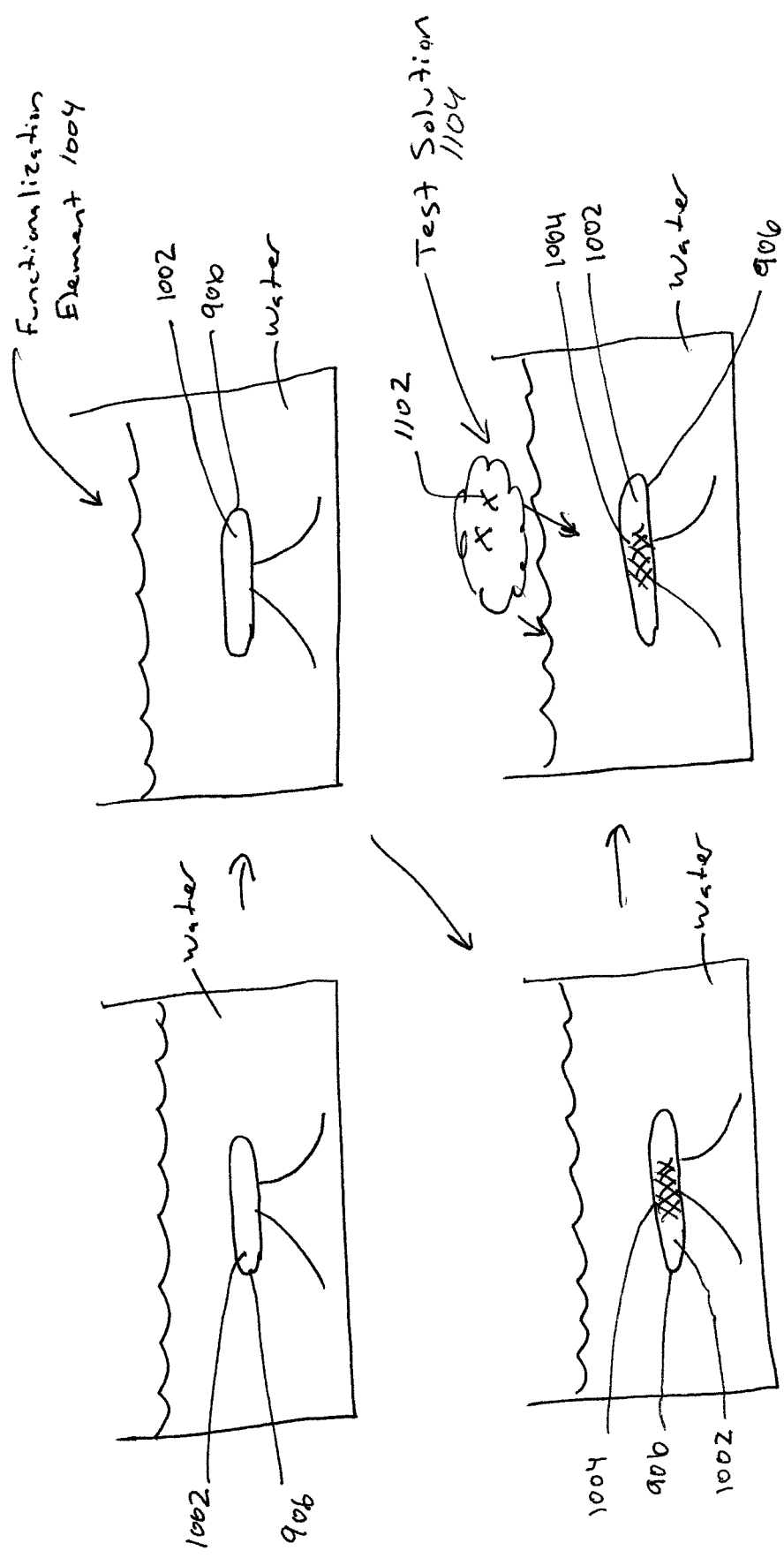
FIG. 11 is a system flow diagram illustrating a method of functionalizing an outer surface of a microcavity according to one embodiment.
Figure 12:
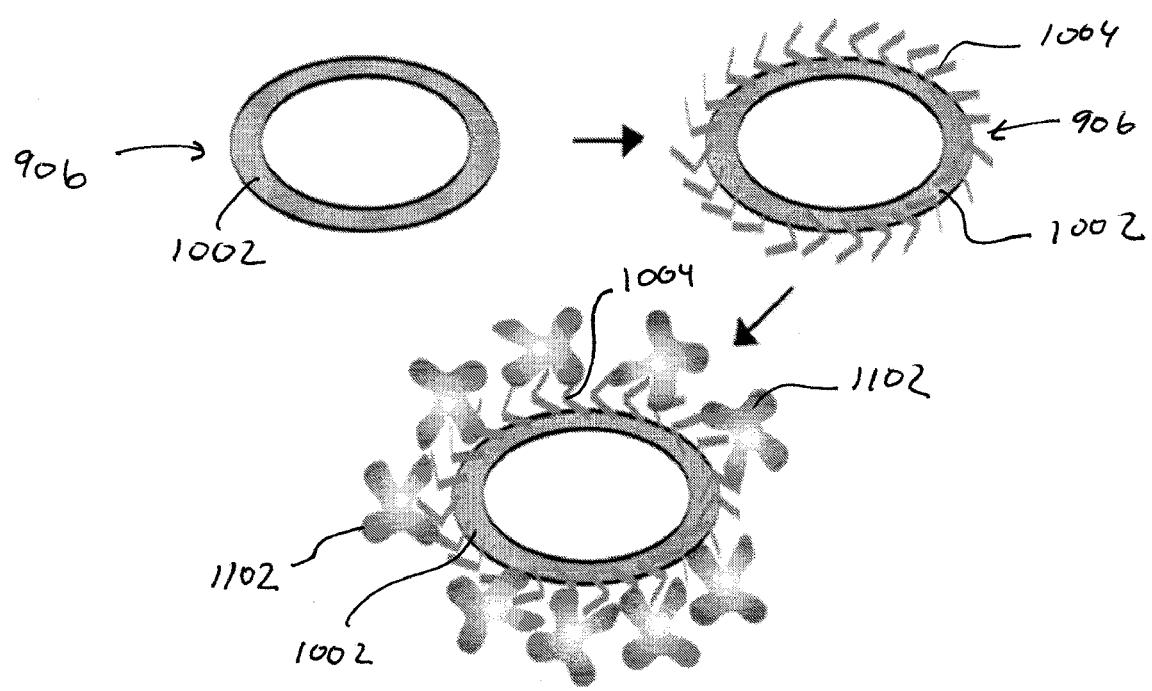
FIG. 12 further illustrates a method of functionalizing an outer surface of a microcavity according to one embodiment as shown in FIG. 11.

Referring to FIGS. 11 and 12, according to one embodiment, the functionalization element 1004 is a single element or specific type of functionalization molecule that is applied to the outer surface 1002 of the microcavity 906. In the illustrated example, a microcavity 906 is placed in a solution or liquid, e.g., water, and the functionalization element 1004 is introduced into the water (e.g. as part of a solution) and is applied or bound to the outer surface 1002. Specific target molecules 1102 in a test solution or other medium can then be detected based on the target molecules 1102 binding to the functionalization element 1004 and causing a shift of the resonant wavelength of the microcavity 906. With embodiments that utilize high-Q or ultra high-Q micro-cavities 906, embodiments can detect a very small number of target molecules 1102, e.g. a single target molecule 1102.

According to one embodiment, the functionalization element 1004 illustrated in FIGS. 11 and 12 is biotin, and a target molecule 1102 to be detected is avidin. Target avidin molecules 1102, e.g., in a test solution or liquid 1104 or other medium, bind to the biotin functionalization elements 1004, which results in a change of resonant wavelength of the microcavity 906. This resonant wavelength change is detected by the detector 908 and indicates that at least one avidin molecule 1102 is bound to the functionalized outer surface 1002.

Figure 13:
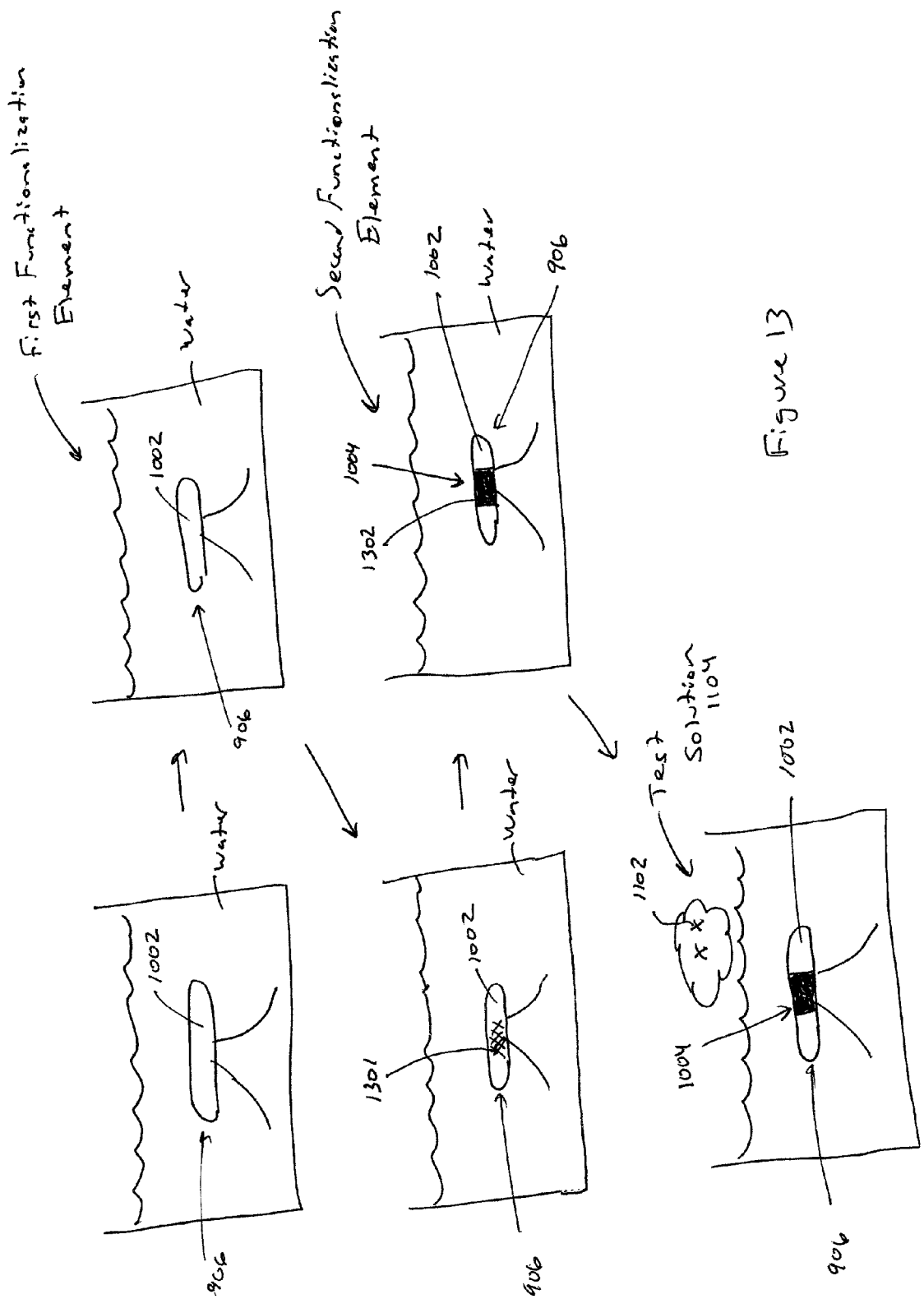
FIG. 13 is a system flow diagram illustrating a method of functionalizing an outer surface of a microcavity using multiple functionalization components according to one embodiment.
Figure 14:
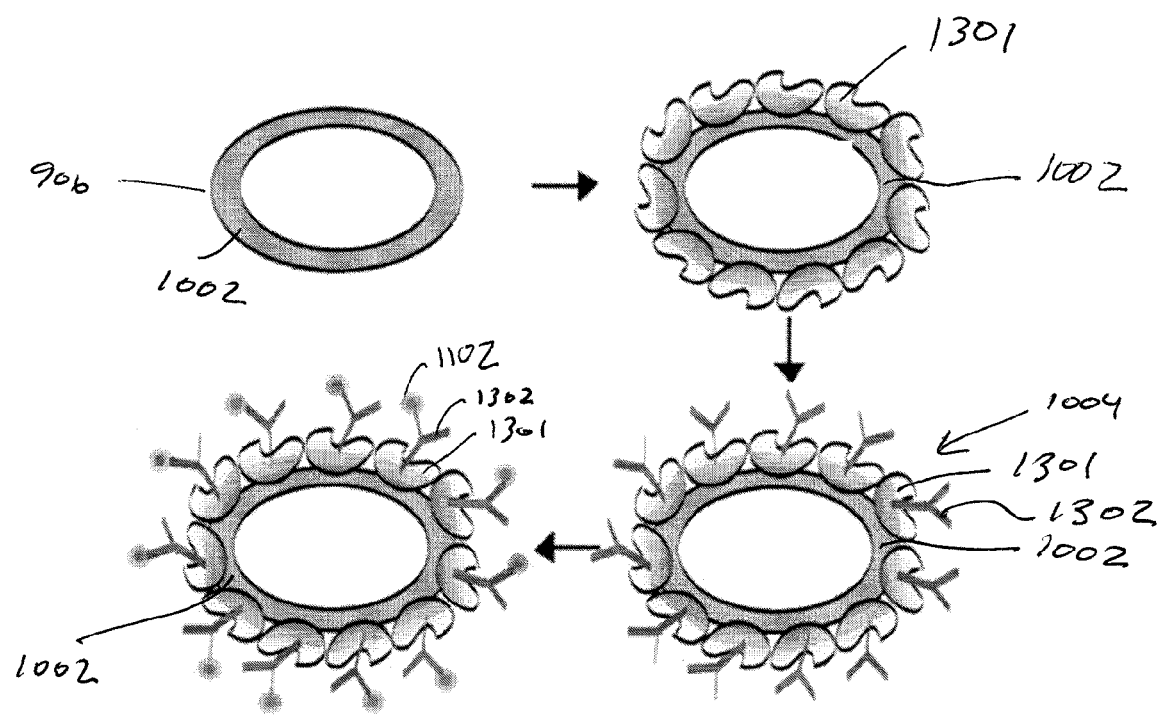
FIG. 14 further illustrates a method of functionalizing an outer surface of a microcavity according to one embodiment as shown in FIG. 13.

Referring to FIGS. 13 and 14, according to another embodiment, the functionalization element 1004 includes multiple elements or components. In the illustrated embodiment, a functionalization element 1004 includes two components—a first functionalization component 1301 that is applied to the outer surface 1002 of the microcavity 906, and a second functionalization component 1302 that is also applied to the outer surface 1002, i.e. by binding or affinity to the first functionalization component 1301. In the illustrated example, a microcavity 906 is placed in a solution or liquid, e.g., water, and the first functionalization component 1301 is introduced into the water (e.g. as part of a solution) and is applied or bound to the outer surface 1002. Thereafter, the second functionalization component 1302 is introduced into the water (e.g. as part of a different solution) and is applied or bound to the outer surface 1002, i.e. by binding or affinity to the first functionalization component 1301. Specific target molecules 1102 in a test solution or other medium can then be detected based on the target molecules 1102 binding to the second functionalization component 1302, which results in a detectable change of the resonant wavelength of the microcavity 906.

In one embodiment, as shown in FIGS. 13 and 14, the first functionalization component 1301 is a protein, which binds to the outer surface 1002 of the microcavity 906, and the second functionalization component 1302 is an antibody, which binds to the protein 1301. Binding of a target antigen 1102 to the antibody 1302 component of the functionalization element 1004 causes a detectable change of resonant wavelength of the microcavity 906.

Alternative embodiments can involve different protein, antibody and antigen configurations depending on whether an antigen or an antibody is to be detected. For example, a first functionalization component can be a protein, which binds to the outer surface 1002 of the microcavity 906 (e.g., via a carboxyl or amine group), a second functionalization component can be an antibody, which binds to the protein, a third functionalization component can be an antigen, which binds to the antibody. Binding of a target antibody to the third or antigen component of the functionalization element 1004 causes a detectable change of resonant wavelength of the microcavity 906. In a further alternative, in order to detect an antibody, an antigen functionalization component can be chemically linked to the outer surface 1002 of the microcavity 906 (e.g., via a carboxyl or an amine group).

In certain embodiments, the resonant wavelength change is a red-shift or increase of the resonant wavelength as a result of a positive change of the refractive index of the microcavity with increasing temperature (in the case of a silica microcavity). However, in other embodiments, the wavelength shift can be a blue shift. For example, it is possible to manufacture a microcavity using a material in which refractive index has the opposite dependence on temperature, resulting a blue shift. Thus, embodiments involving red shifts are provided as examples of how sensor embodiments can function.

Figure 15:
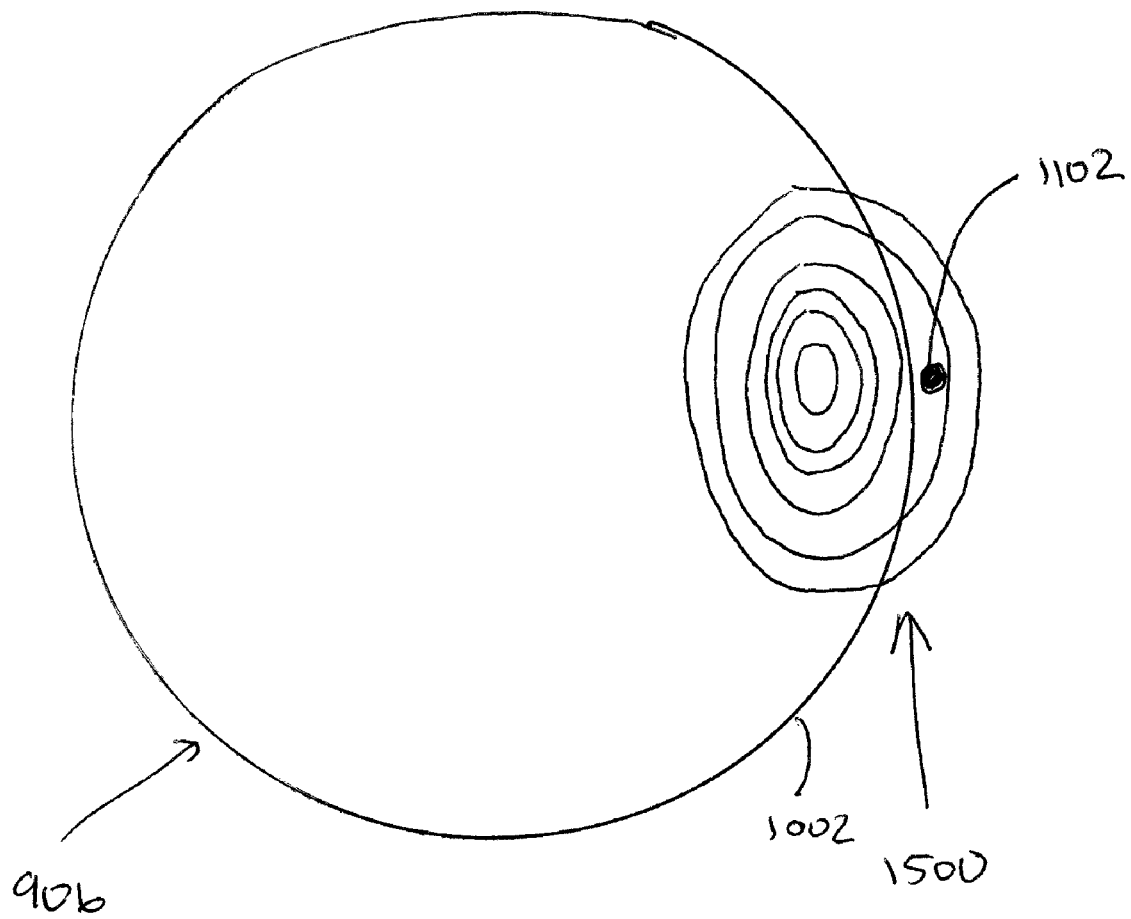
FIG. 15 illustrates an evanescent field extending beyond an outer edge of a microcavity resonator and into an environment.

Referring to FIG. 15, resonant microcavity sensor 900 embodiments are capable of enhanced sensitivities so that a very small number of target molecules 1102 or a single target molecule 1102 can be detected by taking advantage of the interaction of a target molecule 1102 bound to the functionalized outer surface 1002 and optical energy outside of the microcavity 906. A majority of the optical field resides and circulates inside the microcavity 906, but a portion of the optical field evanesces 1500 into the environment (indicated by arrow in FIG. 15). In one embodiment, the resonator can be a whispering gallery mode resonator, and the evanescent field 1500 can be a whispering gallery mode 1500.

Micro-cavities 906 used with embodiments of the invention are capable of high and ultra-high Q values, which produce evanescent fields 1500 having increased intensities. Target molecules 1102 bound to the functionalized outer surface 1002 interact with the high intensity evanescent field 1500, and the resulting thermo-optic effect that is achieved with use of high-Q and ultra-high Q microcavity sensor embodiments enables ultra-sensitive detection based on the resulting pronounced resonant wavelengths shifts. For example intensities of evanescent fields can exceed a GWatt/cm$^2$, and resonant wavelength shifts typically range from femtometer (fm) to picometer (pm) values depending upon the absorption cross section of the molecule.

More specifically, embodiments leverage high Q and ultra-high Q values of micro-cavities 906, e.g., the toroid-shaped silica microcavity 100 shown in FIGS. 1A-D, in two different ways: first, from the narrow linewidth (i.e., improved resolution in measuring shifts), and second, from an increase in the intrinsic shift of the resonance wavelength. As high intensity optical energy circulates within the microcavity 906, the a target molecule 1102 bound to the outer surface 1002 interacts with the resulting high intensity evanescent field 1500 (primarily at the whispering gallery mode). This interaction generates heat which, in turn, increases the temperature of the microcavity 906 and alters the index of refraction of the microcavity 906. This causes the resonant wavelength of the microcavity 906 to red shift. The structural configuration utilized by embodiments, therefore, results in an indirect change of the resonant wavelength, and the resulting resonant wavelength change is proportional to the intensity-induced heating caused by a bound target molecule 1102 interacting with the evanescent field 1500.

The expected resonant wavelength shift resulting from use of micro-cavities 906 can be modeled based on a wave equation that incorporates a perturbing thermal contribution generated by the target molecule/heat source 1102, which causes a change of an optical property (e.g., resonant wavelength) of the microcavity 906. Q value values that enable detection of a very small number of molecules and a single molecule can vary based on different aspects of the microcavity 906. For example, the Q value that is necessary for single molecule detection can depend on the toroid diameter, input power, thermo-optic coefficient of the material, and molecule cross section. In one embodiment, a toroid-shaped microcavity 906 having a Q value of about $10^7$ can be used to detect a single antigen, and a Q value of about $10^6$ can be used to detect a single antibody when the input power to the microcavity 906 is about 1 microwatt. Other Q values may be suitable and may change depending on the type and dimensions of the microcavity. This relationship between the absorption cross section of the target molecule, the optical Q value and the detection sensitivity is reflected in the models provided below.

The theoretical wavelength shift produced by a single molecule 1102 (at the intensity maximum) bound to a functionalized surface 1002 of a high Q or ultra-high Q microcavity 906 can be expressed as the following model:

$$\left[\frac{\delta\lambda}{\lambda}\right]_{SM} = \frac{\sigma\lambda dn/dT}{8\pi^2 n^2 \kappa V} QP \int \frac{|u(\vec{r})|^2}{|\vec{r}|+\varepsilon} d\vec{r} \quad \text{Model (a)}$$

where $\lambda$ is the wavelength, $\sigma$ is the absorption cross section of the target molecule, dn/dT is the opto-thermal constant of silica ($1.3\times10^{-5}$ K$^{-1}$), $\kappa$ is thermal conductivity, n is the effective refractive index of the microcavity 906 (e.g., a silica toroid), V is the optical mode volume, Q is cavity Q-factor, and P is the coupled optical power. As seen in the above Model (a), embodiments leverage high Q values and ultra-high Q values that are possible with micro-cavities 906, e.g., the microcavity 100 shown in FIGS. 1A-D, two separate times resulting in a quadratic dependence of sensitivity with the Q value. The integral in this expression accounts for the spatial overlap of the whispering gallery mode field (u(r)) with the temperature profile created by the nearly point-like heat source of the target molecule 1102 bound to the functionalized outer surface 1002. The parameter "$\varepsilon$" is of order of the physical radius of the target molecule 1102 and, as shown below, has a negligible role in determining the magnitude of predicted resonance wavelength shifts. The strength of the thermo-optic effect resulting from the molecule 1102 heat source depends on the circulating intensity within the whispering gallery mode, as shown by the dependence of the resonance shift on the coupled optical power, microcavity cavity Q value and modal volume.

Using this expression, it is possible to establish a minimum absorption-cross-section sensitivity of the bound target molecule 1102 by setting the observed resonance wavelength shift equal to the microcavity linewidth, $$\sigma_{min} = \frac{V}{Q^2}\frac{1}{P}\frac{8\pi^2 n^2 \kappa}{\lambda dn/dT}\left[\int \frac{|u(\vec{r})|^2}{|\vec{r}|+\varepsilon}d\vec{r}\right]^{-1} \quad \text{Model (b)}$$

Model (b) shows that sensitivity of the microcavity 906 benefits increases quadratically as a result of an increasing Q value. For example, in a toroid-shaped silica microcavity 100 having a Q value of 250 million, a coupled power of 1 mW, a target molecule 1102 radius in the range of 3-50 nm, a light source 902 wavelength of 680 nm, a major toroid diameter of 80 microns, and using optical and thermal constants of silica, an absorption-cross-section limit can be determined to be between $1.1\times10^{-17}$ cm$^2$ and $1.5\times10^{-17}$ cm$^2$. This value is well below the values for many biomolecules, and furthermore represents the limit if detection methods were sensitive only to shifts of order of the microcavity linewidth. If a cross section of $2\times10^{-16}$ cm$^2$ is assumed, which is typical of various molecules, then a single molecule wavelength shift of between 50 fm and 33 fm can be determined, which is easily detected using an ultra-high Q microcavity (e.g., having a Q value greater than $10^8$).

Although embodiments are described with reference to an ultra-high Q toroid-shaped micro-resonator 100, embodiments can be implemented with other micro-cavities 906 having different shapes and Q values so long as the Q value of microcavity is sufficiently high to provide desired evanescent intensity to provide sufficient sensitivity. Micro-cavities 906 having lower Q values can be utilized, e.g., if higher power levels are utilized to compensate for the lower Q values. FIGS. 16-26B illustrate results of tests that were performed to demonstrate microcavity resonant sensor embodiments involving different functionalization elements 1004 and target molecules 1102 and how embodiments provide significant improvements over known sensors.

Figure 16:
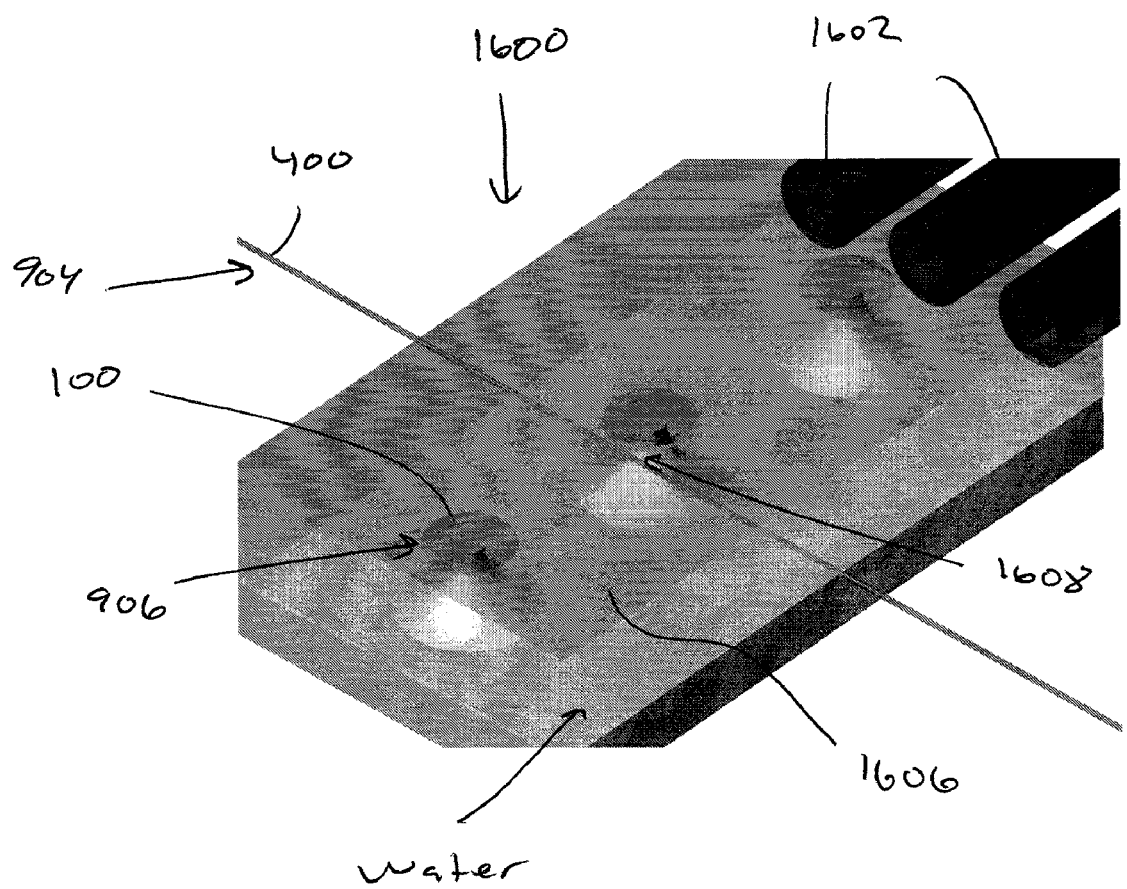
FIG. 16 a system for exposing microcavity resonators immersed in a micro-aquarium for detection of molecules in an aqueous environment according to one embodiment.

Referring again to FIGS. 13 and 14, and with further reference to FIG. 16, tests involved planar arrays of silica micro-toroid whispering gallery resonators 100 (FIG. 1D). Micro-toroids 100 having Q values greater than 100 million were selected and coupled to tunable laser light source 902 and detector 908 using a tapered optical fiber waveguide 904, e.g., a tapered fiber tapered waveguide 400. For this test, the light source 902 was a single-mode, tunable external cavity laser centered at 681.5 nm. The light source 902 was coupled to a single-mode tapered optical fiber waveguide 904, which was fabricated by heating F-SV optical fiber using an oxyhydric torch while stretching the fiber to an average waist diameter of 500 nm.

As shown in FIG. 16, the micro-toroids 100 were immersed in water within a micro-aquarium 1600 having syringes 1602 for injecting and removing solutions. To create the testing chamber or aquarium 1600, the micro-toroids 100 were placed on a high-resolution translation stage (not shown) and simultaneously monitored by two cameras (top and side view) (not shown). With the taper waveguide 904 in close proximity to the micro-toroid 100, pure water was added and a cover slip 1606 (used for imaging/viewing purposes) was placed on top of the immersed micro-toroids 100, thereby forming a water-filled micro-aquarium 1600. The gap 1608 between the micro-toroid 100 and the tapered optical fiber waveguide 904 determines the amount of power coupled into the micro-toroid 100 and can be monitored using the top view camera or by monitoring the input power into the micro-toroid 100.

Solutions were injected into the aquarium 1600 and removed from the aquarium 1600 using the syringes 1602. More specifically, the micro-toroid 100 was first immersed in water, and a first solution (0.1 μM Protein G) was added to the water. Protein G formed a first functionalization component 1301 in the form of a monolayer that was applied to the outer surface 1002 of the micro-toroid 100. The Protein G functionalization component 1301 triggered a red-shift of the resonant wavelength of the micro-toroid 100. The solution around the micro-toroids 100 was cleansed and refilled with fresh water.

A second solution (0.1 μM IL-2 antibody) was then added to the water. The antibody formed a second functionalization component 1302 in the form of a monolayer on the surface of the micro-toroid 100 (based on the affinity of the antibody 1302 to the protein 1301). The antibody functionalization component 1302 triggered a second red-shift of the resonant wavelength of the micro-toroid 100. The solution around the micro-toroids 100 was cleansed and refilled with fresh water.

During this test, the target molecule 1102 was an antigen, unlabeled Interleukin-2 (IL-2), which is a cytokine that is released in response to immune system activation to extrinsic and intrinsic stimuli. A series of solutions having different concentrations of IL-2 ranging from $1 \times 10^{-19}$M (100 zeptomolar) to $1 \times 10^{-6}$M were prepared. Each solution was flowed past the micro-toroid 100 using the syringes 1602, and the volume around the micro-toroids 100 was cleansed between injections.

Both of the intrinsic Q value and the resonant wavelength of the micro-toroid 100 were determined by monitoring the power transmission spectra in real time using an oscilloscope detector 908. The intrinsic Q value was determined by scanning the wavelength of the single-mode laser and measuring both the resonant power transmission and the loaded linewidth (full-width-half-maximum) in the under-coupled regime. The intrinsic modal linewidth (and hence intrinsic Q) was then computed using a resonator-waveguide coupling model. The position of the resonant wavelength was determined by scanning the laser over a 0.03 nm range and recording the resonance position from an oscilloscope detector 908. As the solutions were injected and flowed past the micro-toroids 100, the resonant wavelength of the micro-toroids 100 increased or red-shifted. For IL-2, the highest sensitivity occurs in the lower concentration range. FIGS. 17-26B present the data acquired during these tests and demonstrate effectiveness and advantages of embodiments of the invention.

Figure 17:
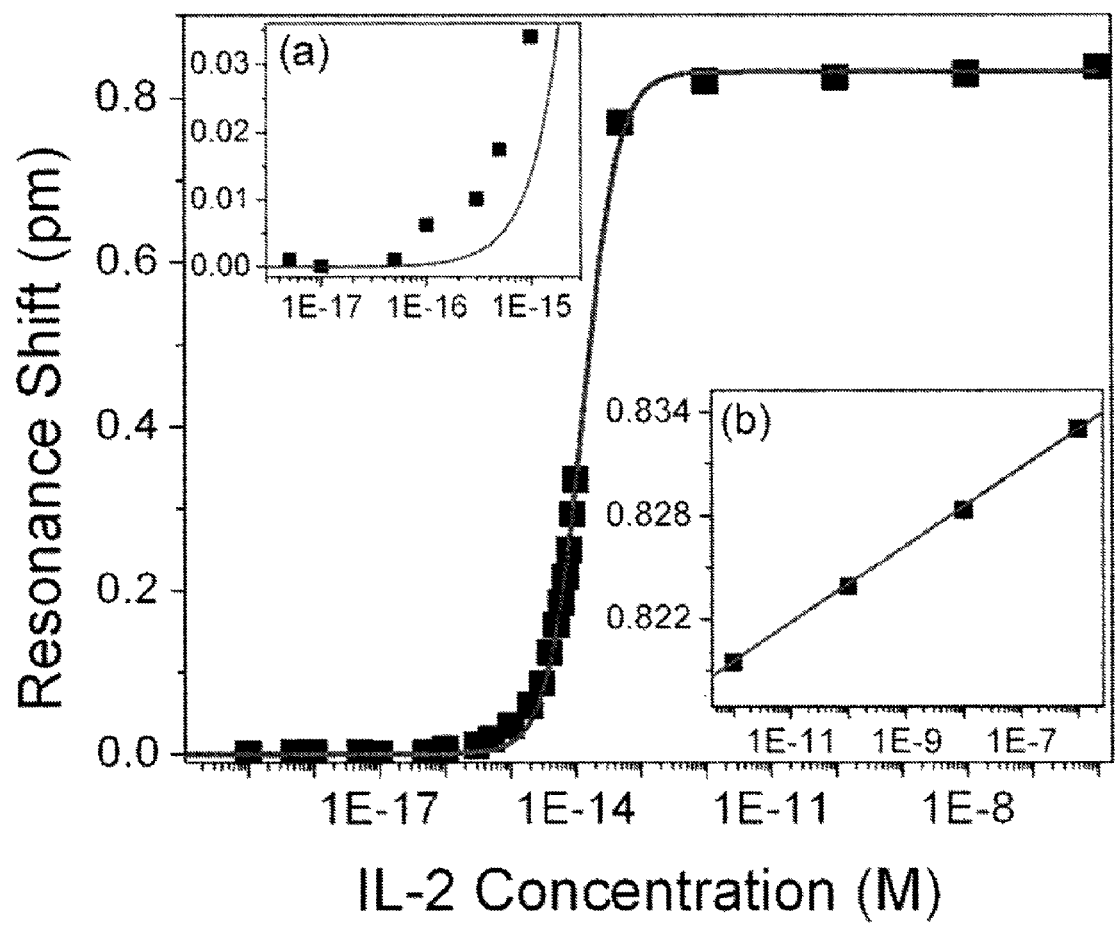
FIG. 17 is a graph illustrating resonant wavelength shifts resulting from IL-2 solutions having concentrations ranging from $10^{-19}$M to $10^{-6}$M.

Referring to FIG. 17, the dose-response curve acquired during this test is sigmoidal or "S-shaped." A detectable response was obtained at an IL-2 concentration of about $3 \times 10^{-16}$M with greater than 10:1 signal-to-noise ratio, as shown in inset (a) of FIG. 17. With increasing IL-2 concentrations, the resonant wavelength shifts were detectable even for concentrations as large as $10^{-6}$M, as shown in inset (b) of FIG. 17. This working range represents a significant improvement over known sensor devices. In particular, this working range represents a ten decade concentration range ($10^{10}$), which is a $10^7$ improvement over other room temperature detection techniques, such as microfluidic fluorescence assays, nanowire sensors and micro-cantilevers, which have working ranges of only about $10^3$.

Figure 18:
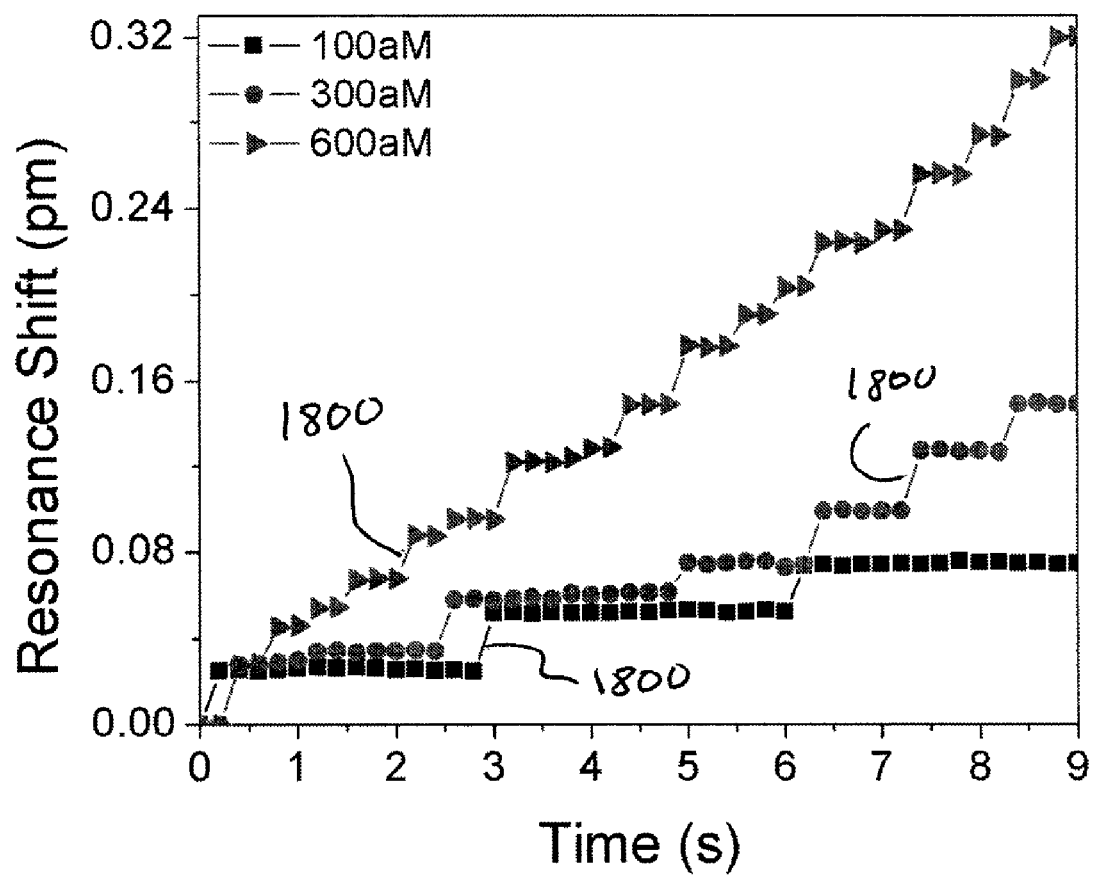
FIG. 18 is a graph illustrating the position of the resonance wavelength as a function of time at three different Interleukin 2 concentrations, and binding rates increases with increasing concentrations.
Figure 19:
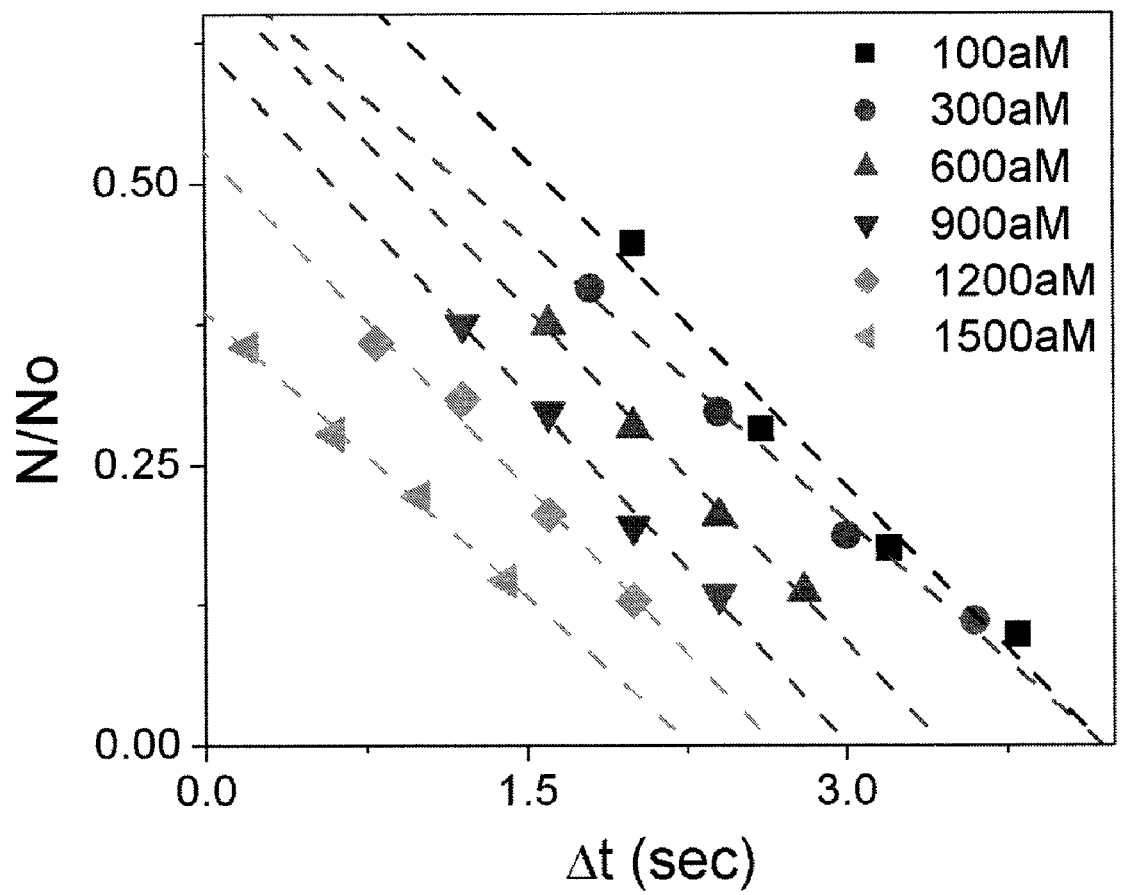
FIG. 19 is a graph illustrating the fraction of non-binding events over time for a series of IL-2 concentrations ranging from 100 aM to 1500 aM and that the time between molecule binding events decreases as the concentration increases.
Figure 20A:
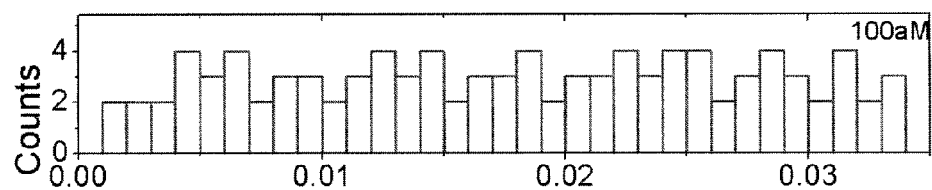
FIG. 20A is a histogram showing the relationship between total resonant wavelength shift and number of molecules bound to the outer surface of a resonator when using a test solution having an IL-2 concentration of 100 aM.
Figure 20B:
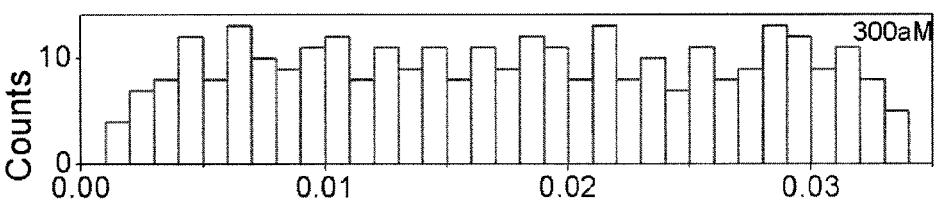
FIG. 20B is a histogram showing the relationship between total resonant wavelength shift and number of molecules bound to the outer surface of a resonator when using a test solution having an IL-2 concentration of 300 aM.
Figure 20C:
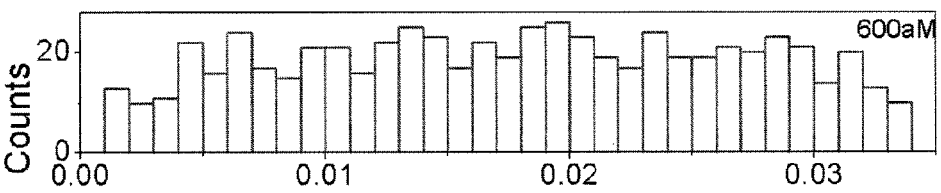
FIG. 20C is a histogram showing the relationship between total resonant wavelength shift and number of molecules bound to the outer surface of a resonator when using a test solution having an IL-2 concentration of 600 aM.
Figure 20D:
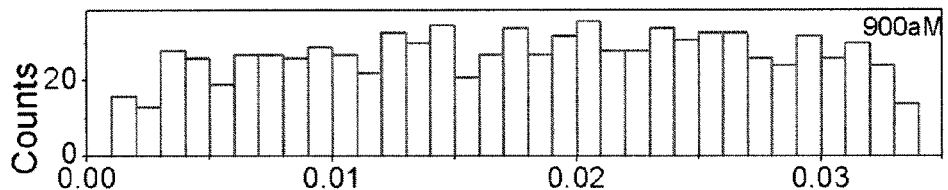
FIG. 20D is a histogram showing the relationship between total resonant wavelength shift and number of molecules bound to the outer surface of a resonator when using a test solution having an IL-2 concentration of 900 aM.
Figure 20E:
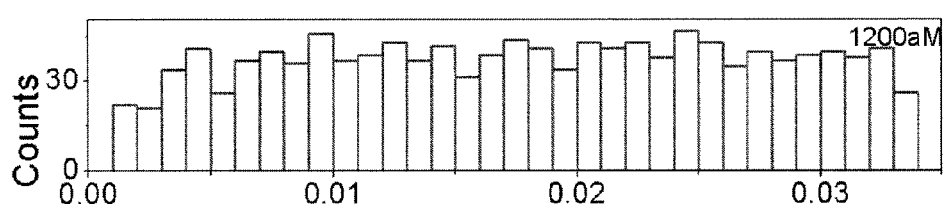
FIG. 20E is a histogram showing the relationship between total resonant wavelength shift and number of molecules bound to the outer surface of a resonator when using a test solution having an IL-2 concentration of 1200 aM.
Figure 20F:
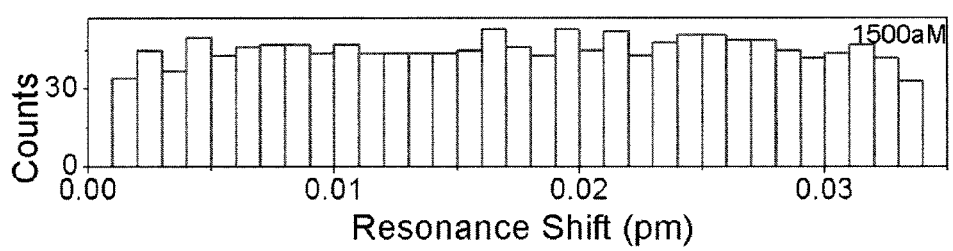
FIG. 20F is a histogram showing the relationship between total resonant wavelength shift and number of molecules bound to the outer surface of a resonator when using a test solution having an IL-2 concentration of 1500 aM.
Figure 21A:
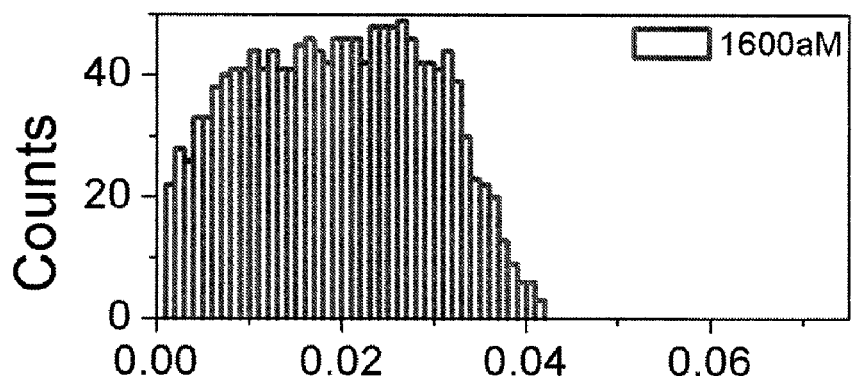
FIG. 21A is a graph illustrating molecule binding events occurring in a single bin time period using a test solution having an IL-2 concentration of 1600 aM.
Figure 21B:
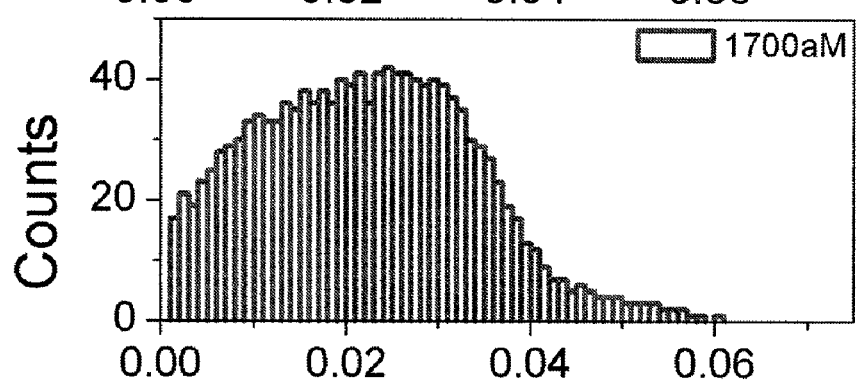
FIG. 21B is a graph illustrating molecule binding events occurring in a single bin time period using a test solution having an IL-2 concentration of 1700 aM.
Figure 21C:
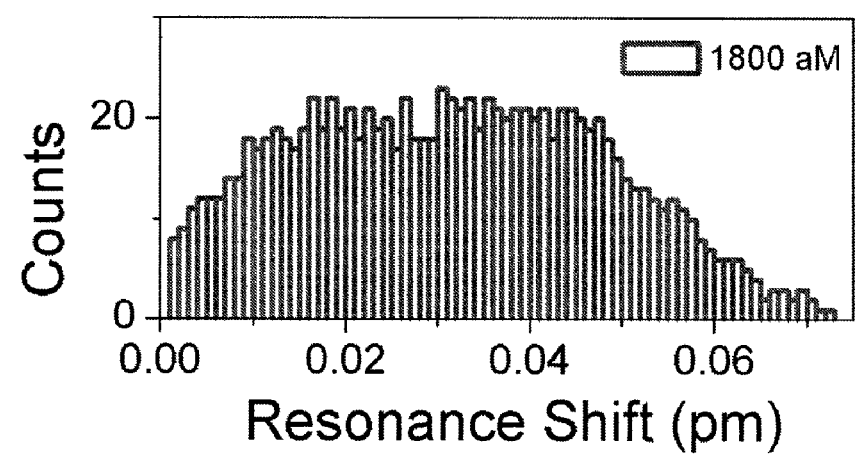
FIG. 21C is a graph illustrating molecule binding events occurring in a single bin time period using a test solution having a concentration of 1800 aM.
Figure 22A:
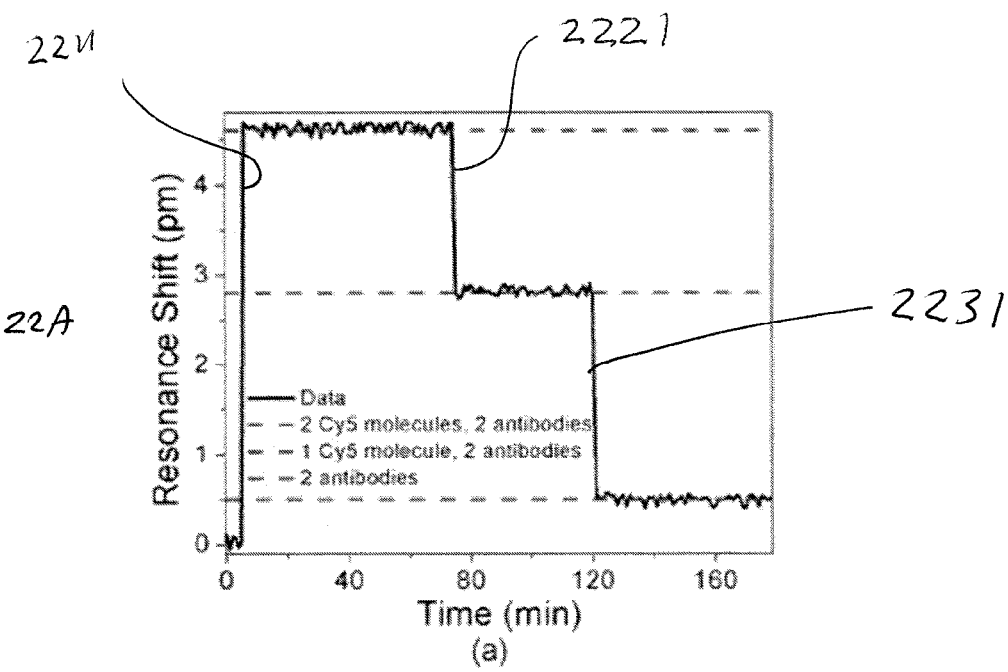
FIG. 22A is a graph illustrating an initial red shift followed by two blue shifts as two Cy5 molecules are photobleached, confirming single molecule detection capabilities of embodiments.
Figure 22B:
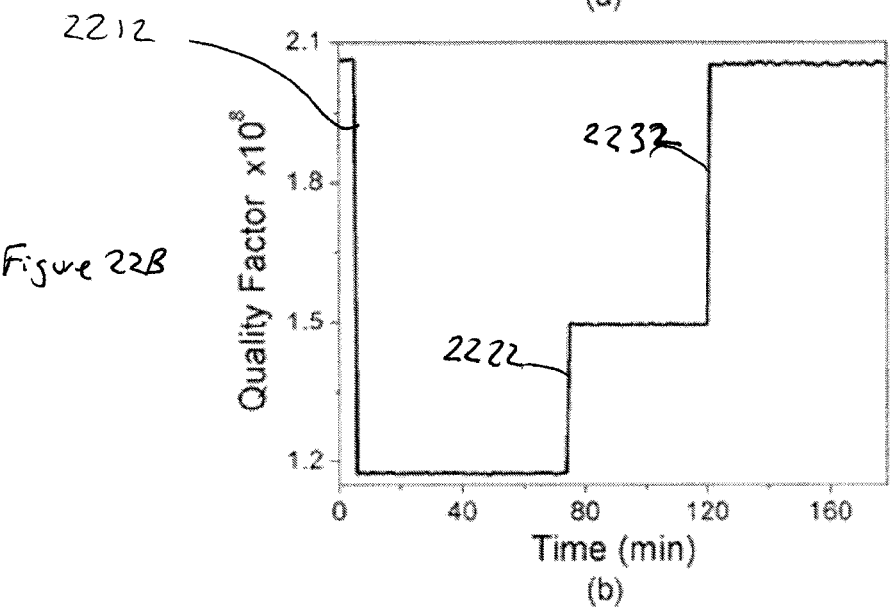
FIG. 22B is a graph illustrating a red shift followed by a sequential recovery of the Q value as two Cy5 molecules are photobleached, confirming single molecule detection capabilities of embodiments.

FIG. 18 illustrates the position of the resonance wavelength as a function of time at three different IL-2 concentrations. The transition or steps 1800 represent binding of individual or discrete IL-2 antigen molecules 1102 to the functionalized outer surface 1002 of a micro-toroid 100. At higher IL-2 concentrations, the general slope of the data indicated that the rate at which IL-2 molecules 1102 bind to the outer surface 1002 increases. Thus, the frequency of binding of individual molecules 1102 to the outer surface 1002 increases as the concentration of the solution increases, as further illustrated in FIGS. 19-21F. FIG. 19 illustrates a fraction of non-events (non-binding of IL-2 molecules) relative to time for a series of solutions having different IL-2 concentrations ranging from 100 aM to 1500 aM. As the IL-2 concentration increases, the time between binding events decreases. FIGS. 20A-F are histograms representing different IL-2 concentrations ranging from 100 aM to 1500 aM and corresponding to the data shown in FIG. 19. FIGS. 20A-F show the relationship between total resonant wavelength shift and number of molecules 1102 bound to the functionalized outer surface 1002 of the micro-toroid 100. FIGS. 20A-F also illustrate that each histogram has a maximum shift value that is independent of the concentration. FIGS. 21A-C illustrate multiple binding events occurring in a single bin time period (0.001 pm bin size) as the IL-2 concentration increases above 1500 aM to concentrations between 1600 aM and 1800 aM. Thus, the data reflected in FIGS. 17-21C are consistent with and demonstrate binding of single or individual IL-2 antigens 1102 to the functionalized outer surface 1002 of the micro-toroid 100 without the need for a fluorescent or metal label.

To further confirm that the binding that was observed is binding of single molecules 1102, a single molecule photobleaching experiment was performed using a Cy5 labeled antibody. While this fluorescent probe's absorption maximum is 645 nm, the tail of the absorption overlaps with the 680 nm resonance. Therefore, it is possible to photobleach this dye using a 680 nm excitation source or the evanescent field 1500 of the micro-toroid 100. The resonant wavelength location in $H_2O$ was acquired for five minutes after the outer surface 1002 was functionalized with a Protein G functionalization element 1004. Then the Cy5 labeled antibody 1002 was injected into the bath surrounding the micro-toroid 100.

Both the resonant wavelength shift and the optical Q value of the micro-toroids 100 were monitored. A low concentration Cy5 solution was injected until a response was observed. This concentration was selected to ensure that only a few molecules would bind to the whispering gallery portion of the micro-toroids 100. Initially, binding of two Cy5 fluorescent labeled antibodies to the functionalized outer surface initially produced a resonant wavelength red shift 2211 of about 4.5 pm, and Q value decrease 2212 of about $0.9 \times 10^8$. These events were followed by two, sequential, blue-shifts and Q value increases. Specifically, at about 80 minutes, a first blue shift 2221 and a first Q value increase 2222 were observed, and at about 120 minutes, a second blue shift 2231 and a second Q value increase 2232 were observed as the two Cy5 fluorescent labeled molecules are photobleached, thus suggesting that two Cy5 molecules are observed. Estimates of Q value shifts resulting from binding of two Cy-5 molecules are in the range of the observed initial Q shift, furthering suggesting that the bleaching data represent individual Cy5 molecules. It should be noted that the resonant shift does not return to zero or initial position because there are still two antibodies bound to the surface of the micro-toroid. The existence of this residual shift is further evidence that both Cy5 molecules were photo-bleached and did not detach from the outer surface 1002 of the micro-toroid 100.

Figure 23:
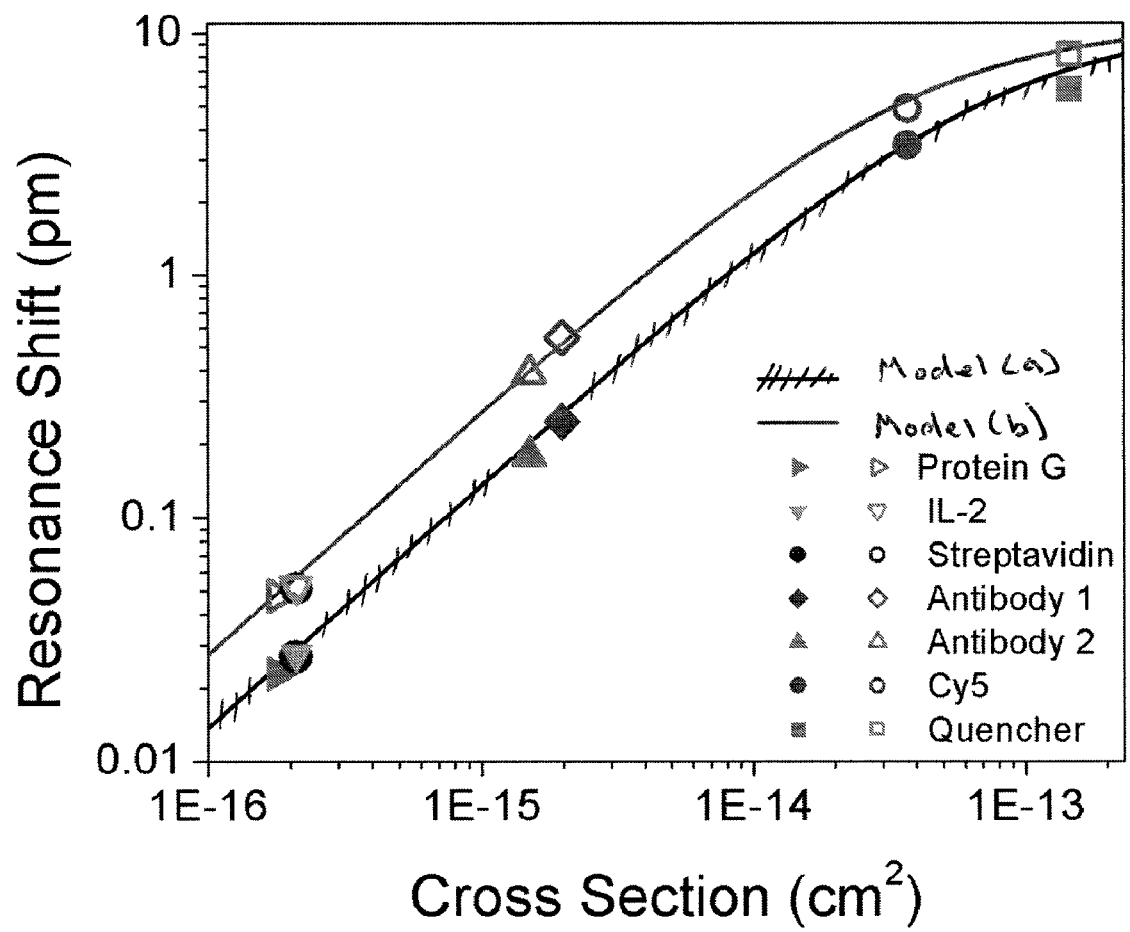
FIG. 23 is a graph illustrating confirmation of an expected theoretical relationship between absorption cross section and maximum resonance shift by experiments using Interleukin-2, Streptavidin, Protein G, two different IL-2 antibodies, Cy5 and QSY-21.

FIG. 23 summarizes theoretical predictions of the thermo-optic effect resulting from interaction of a target molecule 1102 and an evanescent field 1500 (based on models (a) and (b) provided above) and experimental test results by plotting the largest measured single-molecule resonance shift versus absorption cross section. For small cross sections (that do not lower Q value of the microcavity), a linear dependence is expected based on the thermo-optic model assuming a negligible impact of the size parameter $\epsilon$ (physical radius of the target molecule 1102). The coupled input power and toroid 100 diameter were constant throughout the measurements.

FIG. 23 also shows that there is excellent alignment of the data across all of the distinct molecules and for both Q values ($1 \times 10^8$ and $2 \times 10^8$). Furthermore, higher Q values provide proportionally larger resonant wavelength shifts, consistent with the thermo-optic model representing the interaction of a bound target molecule 1102 and an evanescent field 1500. As shown in FIG. 23, detection is not purely linear in cross section due to the ability of a single molecule 1102 which is highly absorbing to decrease the Q value of the micro-toroid 100. This phenomenon is realized when testing both Cy5 and QSY-21, both of which can impact Q value even at the single molecule level. A primary reason for the non-linearity at large cross sections is that large molecules are able to significantly change Q value when bound. Because the Q value is decreased, the circulating intensity is reduced, and the thermo-optic interaction and heating is also reduced. Thus, there may be cases when a resonant wavelength is red-shifted and the Q value of the microcavity 906 remains substantially constant (e.g., with small molecules), and other cases when a resonant wavelength is red-shifted and the Q value is reduced (e.g., with large molecules).

Figures 24A, 24B:
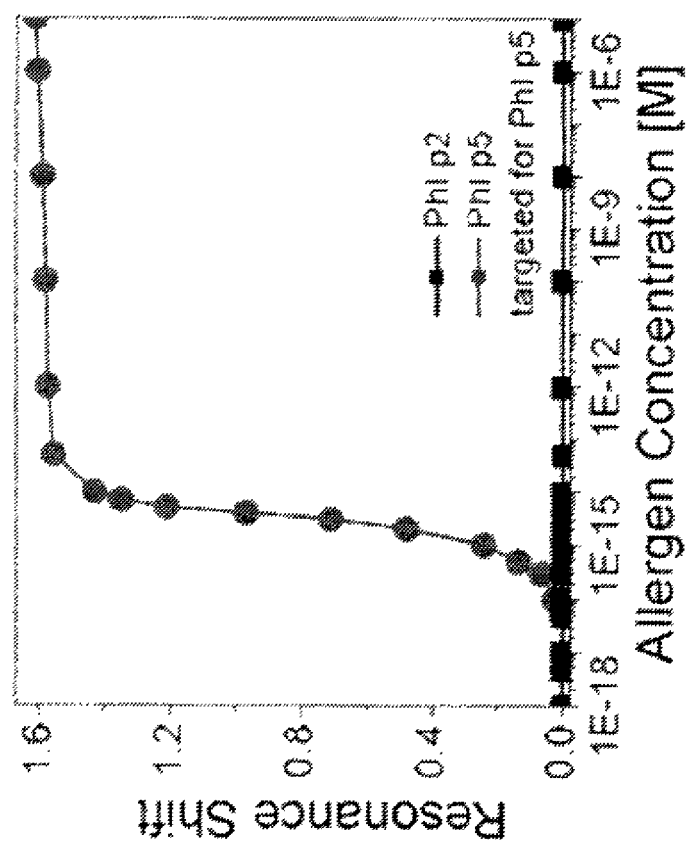
FIG. 24A is a graph illustrating resonant wavelength shifts at different allergen concentrations when an outer surface of a micro-resonator is functionalized with Phl p2 monoclonial antibodies.
FIG. 24B is a graph illustrating resonant wavelength shift at different allergen concentrations when an outer surface of a micro-resonator is functionalized with Phl p5 monoclonial antibodies.

As a further example of how embodiments can be implemented, referring to FIGS. 24A-B, embodiments can be used to detect allergens, e.g., using Phl p 2 or Phl p 5 antibodies, based on a resulting resonant wavelength shift. FIG. 24A illustrates test results using a toroid-shaped micro-resonator 100 having an outer surface 1002 that is functionalized with Phl p 2 monoclonal antibodies 1004. As discussed above, the micro-resonators 100 were immersed in water in a micro-aquarium 1600. When Phl p 2 allergens 1102 are injected into the water, the Phl p 2 allergens 1102 bind to the Phl p 2 antibodies 1004. FIG. 24B illustrates that toroid-shaped microcavity 100 can also be functionalized with Phl p 5 monoclonal antibodies 1004. In this case, when Phl p 5 allergens are injected, the Phl p 5 allergens 1102 bind to the Phl p 5 antibodies 1004.

Embodiments can also be configured so that thermo-optic effects in water (or another environment) and in silica (or other material of a microcavity 906) caused by heat generated by the interaction of a bound target molecule 1102 and an evanescent field 1500 are controlled or balanced by tuning the dimensions of a microcavity 906. For example, the major diameter $D_M$ and/or the minor diameter d (FIG. 1D) of a toroid microcavity 100 can be controlled to balance heating contributions. More particularly, optical micro-cavities demonstrate resonant wavelength red-shifts in air because both silica and air have positive thermo-optic coefficients (dn/dT). In contrast, the thermo-optic coefficient of water is negative. It is possible to manipulate these characteristics to balance heating contributions of the water environment and the silica material of a microcavity 906 resulting from heat generated by interaction of a bound molecule 1102 and an evanescent field 1500.

Balanced or neutral heating occurs for a specific spatial overlap of the whispering gallery mode with the water and can be computed, e.g., using a COMSOL Multiphysics 3.2 finite element code with the Chemical Engineering Module. This overlap, in turn, corresponds to a specific whispering-gallery diameter. Micro-cavities 906 configurations can cause deviations from balanced heating if the major and/or minor diameters of a toroid microcavity 100 are too large or too small). For example, the resonant wavelength red-shifts when a diameter is too large and the silica component of the shift is dominant, or blue shifts when the diameter is too small and the water component of the shift is dominant. To demonstrate that embodiments can be so balanced, a series of ultra-high-Q micro-toroids 100 with a range of major and minor diameters (FIG. 1D) were fabricated and tested, the results of which are provided in FIGS. 25 and 26.

Figure 25:
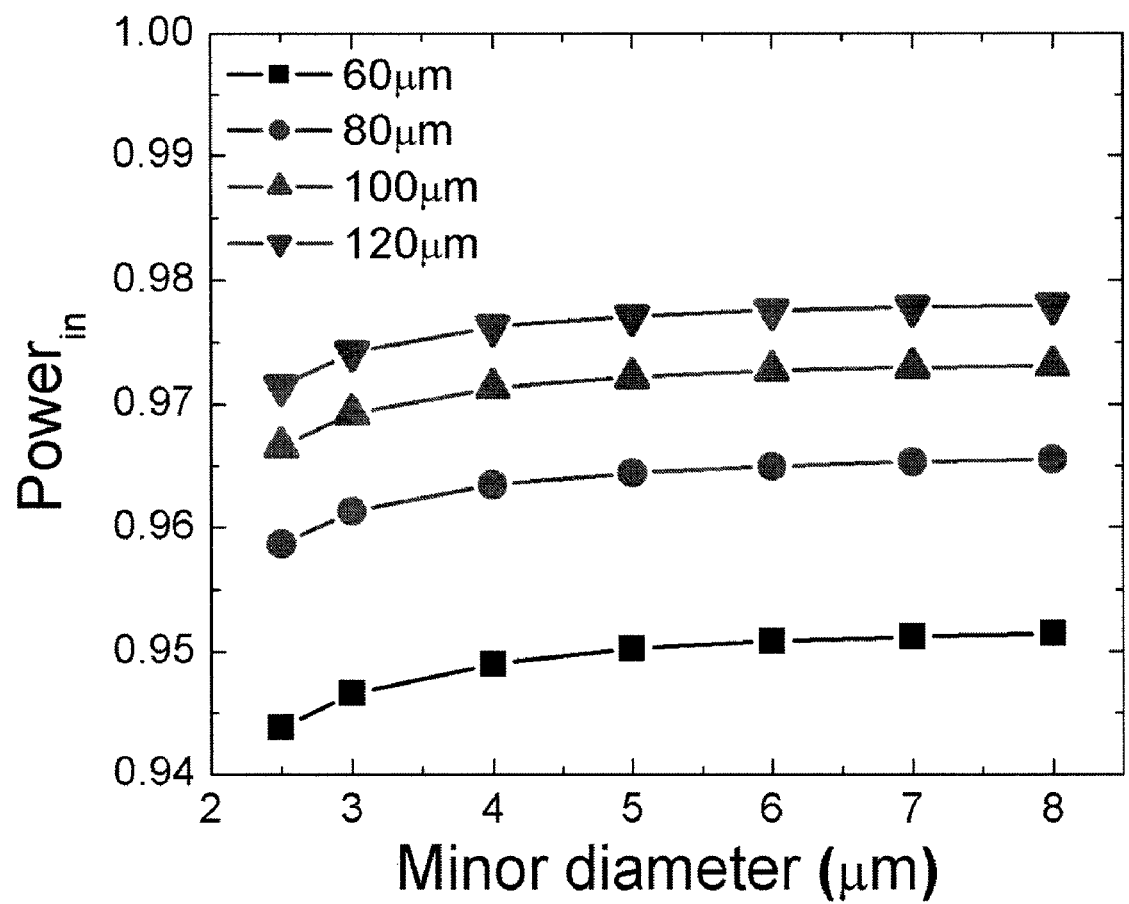
FIG. 25 illustrates a model of optical modes of toroid resonators having different major and minor diameters.
Figure 26:
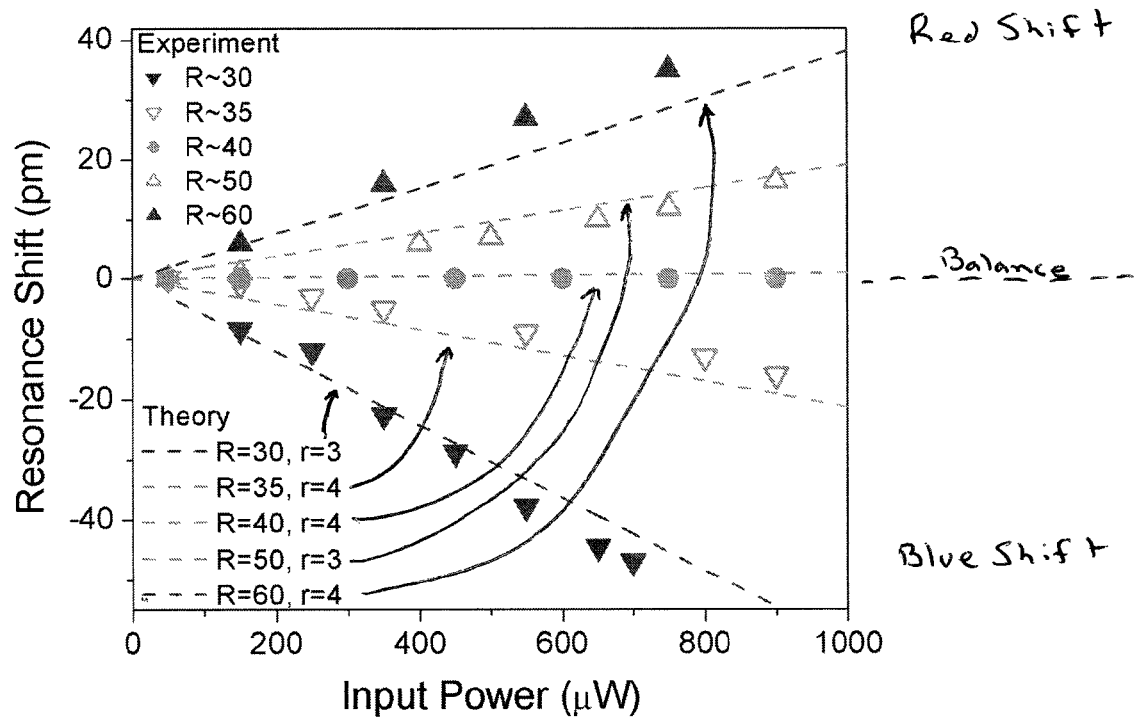
FIG. 26 is a graph illustrating measured tuning of the whispering gallery mode relative to optical power for toroid micro-resonators having different major and minor radii.

FIG. 25 illustrates FEMLAB modeling of the optical mode in a toroid microcavity 100 having different major and minor diameters, and FIG. 26 illustrates measured tuning of the whispering gallery mode relative to coupled optical power. Each data set corresponds to major and minor radii. As shown in FIG. 26, micro-toroids 100 having larger radii experience a red shift while micro-toroids 100 having smaller radii experience a blue shift with increasing coupled power. At a major diameter of about 80 microns, a balanced or neutral condition was observed.

It will be understood from the above description with reference to FIGS. 10-26, embodiments using a functionalized outer surface 1002 advantageously provide the ability to detect various numbers of and different types specific molecules 1102, including the ability to detect a very small number of specific molecules 1102 and a single molecule 1102 as needed. Embodiments realize these advantages without the need for conventional fluorescent or metal labels and instead utilize high Q and ultra-high Q micro-cavities that generate evanescent fields 1500 with increased intensities to expand sensitivity into the single molecule regime. Moreover, embodiments provide such capabilities while providing a structure that can be used with various substrates 120, including a silicon chip.

Label-free sensor embodiments enable and/or improve new biological research, including monitoring growth factors being emitted from living cells in vivo by functioning at room temperature conditions and performing both label-free single molecule measurements and higher concentration measurements on a single platform. Further, embodiments are biocompatible and can operate in various environments, including aqueous or water environments and other environments such as HCl environments. As such, embodiments can be utilized for direct detection of proteins within biological samples without labeling or separation, such as detecting tumor markers present at low concentration in a serum sample or analyzing rare factors secreted from cells in culture.

Embodiments discussed with reference to examples involving biotin and avidin (FIGS. 11 and 12), a protein, an antibody and an antigen (FIGS. 13 and 14) and allergens (FIGS. 24A-B) are provided as examples of how embodiments can be implemented. Embodiments can be used with various other functionalization elements 1004 and components and be used to detect various molecules 1102 as needed. For example, a functionalization element 1004 can also be a DNA strand that is used to bind and detect a complimentary DNA strand. Further, the functionalization element 1004 can be, for example, silane, bovine serum albumin, an electro-optic material, for example, antibodies to monitor for viruses or molecular machines, such as ribosome which takes in an RNA building block and builds DNA, to monitor for the presence of the RNA building block.

Referring again to FIG. 9, according to another embodiment, a label-free microcavity resonant sensor 900 has enhanced sensitivities to allow detection and discrimination of a small number of specific molecules, even a single, specific molecule, based on changes of Q value of a microcavity 906. Thus, with these embodiments, detection does not rely on changing resonant wavelengths (as discussed with reference to FIGS. 10-26). Further, embodiments that detect molecules or species of molecules based on Q value changes do not require a functionalized outer surface.

Embodiments can be used for various monitoring applications to detect specific molecules or a particular species. For example, embodiments can use high-Q and ultra-high Q micro-cavities 906 to detect a specific species within a mixture of molecules. One example of how embodiments can be applied is detecting "heavy" water ($D_2O$) (hereafter referred to as "heavy water") within ordinary or "light" water ($H_2O$) (hereafter referred to as "ordinary water"). Heavy water is water in which the hydrogen is composed of over 99% deuterium atoms. One use of heavy water is to moderate neutrons that are emitted by fissioning uranium. Thus, the ability to detect very small quantities of heavy water may be important in identifying potential nuclear-related activities. Further, embodiments can be used to monitor water supplies. Normal water includes about 5000:1 parts ordinary water to heavy water. Embodiments of the invention can be used to monitor water supplies to detect changes in heavy water levels, which may indicate processing of natural water to remove and accumulate heavy water.

Figure 27:
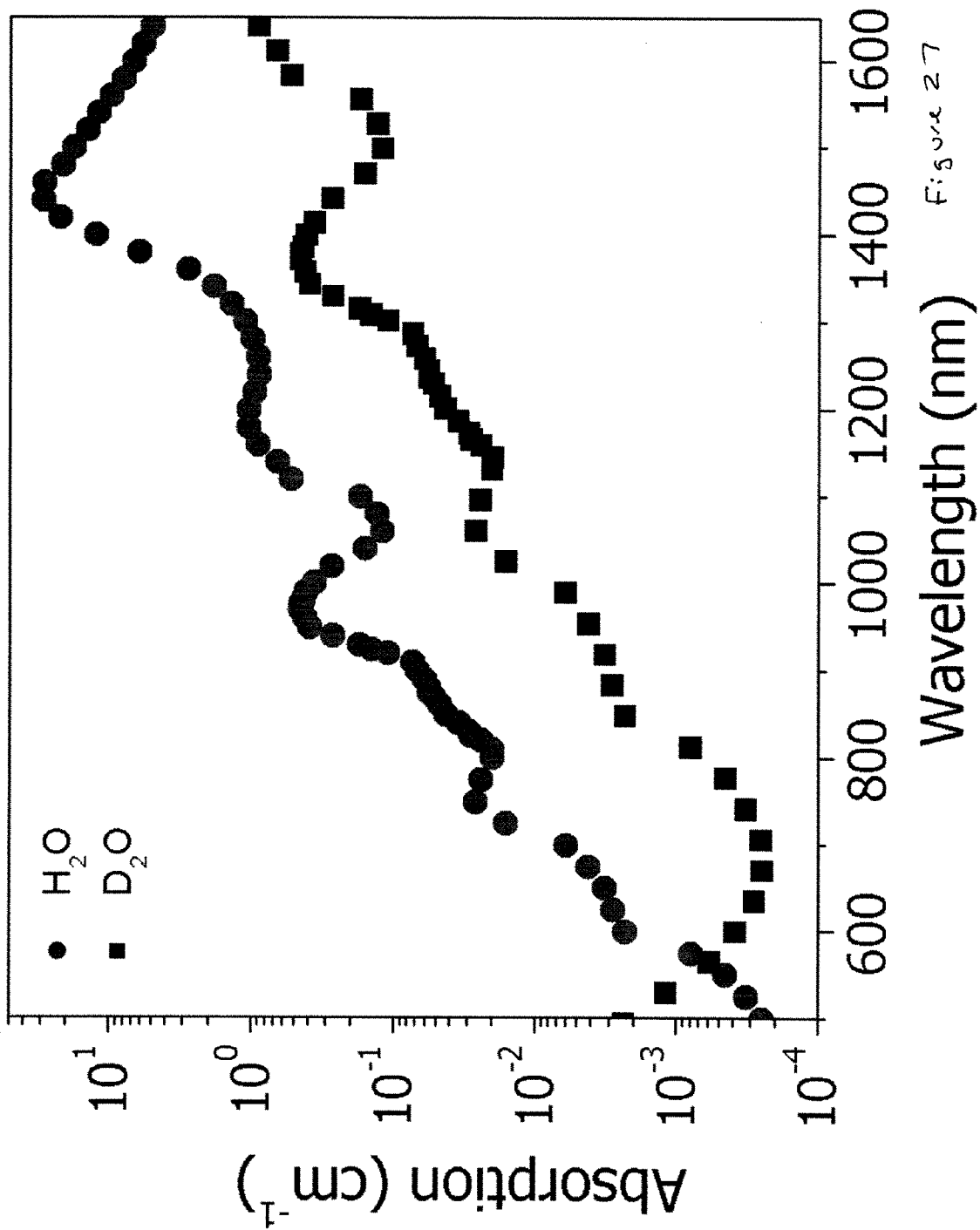
FIG. 27 is a graph illustrating different absorption of optical energy by water ($H_2O$) and heavy water ($D_2O$)

Heavy water has the same index of refraction and radiation loss as ordinary water. However, as shown in FIG. 27, heavy water and ordinary water have different absorption characteristics. These absorption differences exist across a range of wavelengths, including about 600 nm to about 1600 nm. Embodiments of highly sensitive resonant sensors can detect very small quantities of heavy water based on changes of Q value of a microcavity 906, which result from heavy water absorbing different quantities of optical energy. More particularly, microcavity resonator sensors 900 that are immersed in ordinary water have lower quality factors compared to sensors 900 that are immersed in heavy water since ordinary water absorbs more optical energy, thereby reducing the Q value. Embodiments provide enhanced sensitivities to detect small quantities of heavy water based on these Q value shifts.

For example, at a wavelength of about 1300 nm, the Q value of a micro-cavity 906, e.g., a micro-toroid 100 (FIG. 1D), in ordinary water is about $10^6$ whereas the Q value of the same micro-toroid 100 in heavy water is about $10^7$. Embodiments are advantageously able to detect concentrations of 0.0001% (1 ppmv) of heavy water in ordinary water based on changes of Q values of this magnitude, in contrast to various other known resonator devices that are not even able to achieve these Q values. This enhanced sensitivity represents an order of magnitude improvement over known heavy water detection systems.

With further reference to FIGS. 4 and 9, heavy water detection tests were performed using a planar array of ultra-high-Q micro-toroids 100 (FIG. 1D) and a single-mode, tunable external cavity laser light source 902 centered at 1320 nm. The laser light source 902 was coupled to a single-mode optical fiber 904 containing a short, tapered section or waist 406 that acts as a waveguide. The tapered section 406 was used to couple power into and out of the whispering gallery modes of the micro-toroid 100. Tapered fibers for testing at 1300 nm were pulled from SMF-28 optical fiber to an average waist diameter of one micron. The heavy water used during these tests was purchased from Sigma-Aldrich Corporation, 3050 Spruce Street, St. Louis, Mo.

The micro-toroids 100 were immersed in a micro-aquarium (FIG. 16) and exposed to solutions having different heavy water concentrations. The micro-toroids 100 were placed on a high-resolution translation stage (not shown) and were simultaneously monitored by two cameras (top and side view) (not shown). With the taper waveguide 400 in close proximity to the micro-toroid 100, water having different concentrations of heavy water added and a cover slip was placed on top of the micro-toroids 100, forming a water-filled aquarium. Solutions having different heavy water concentrations were added, and after each solution was tested, the resonance spectra were recorded and then the solution around the toroid was removed and replaced with the next solution in the series.

In a first series of measurements, the micro-toroid 100 was initially immersed in 100% heavy water. The Q value was measured, an then all of the solution was removed until the toroid 100 was in air and the aquarium chamber was flushed. The micro-toroid 100 was then immersed in solutions having different heavy water concentrations based on 10% increments (10% ordinary water in heavy water; 20% ordinary water in heavy water; 30% ordinary water in heavy water, and so on).

For each solution, the intrinsic Q value and the resonance position were determined from the transmission spectra. The intrinsic Q value was determined by scanning the single-mode laser and measuring both the transmission and the loaded linewidth (full-width-half-maximum) in the under-coupled regime over a range of coupling conditions. The intrinsic modal linewidth (and hence intrinsic Q) was then computed using a suitable coupling model, and the resonance position provided by the oscilloscope monitor was recorded. After each series of measurements for a given solution, the aquarium chamber was flushed and re-filled with a new solution, and new Q value and resonance position measurements were conducted.

Figure 29:
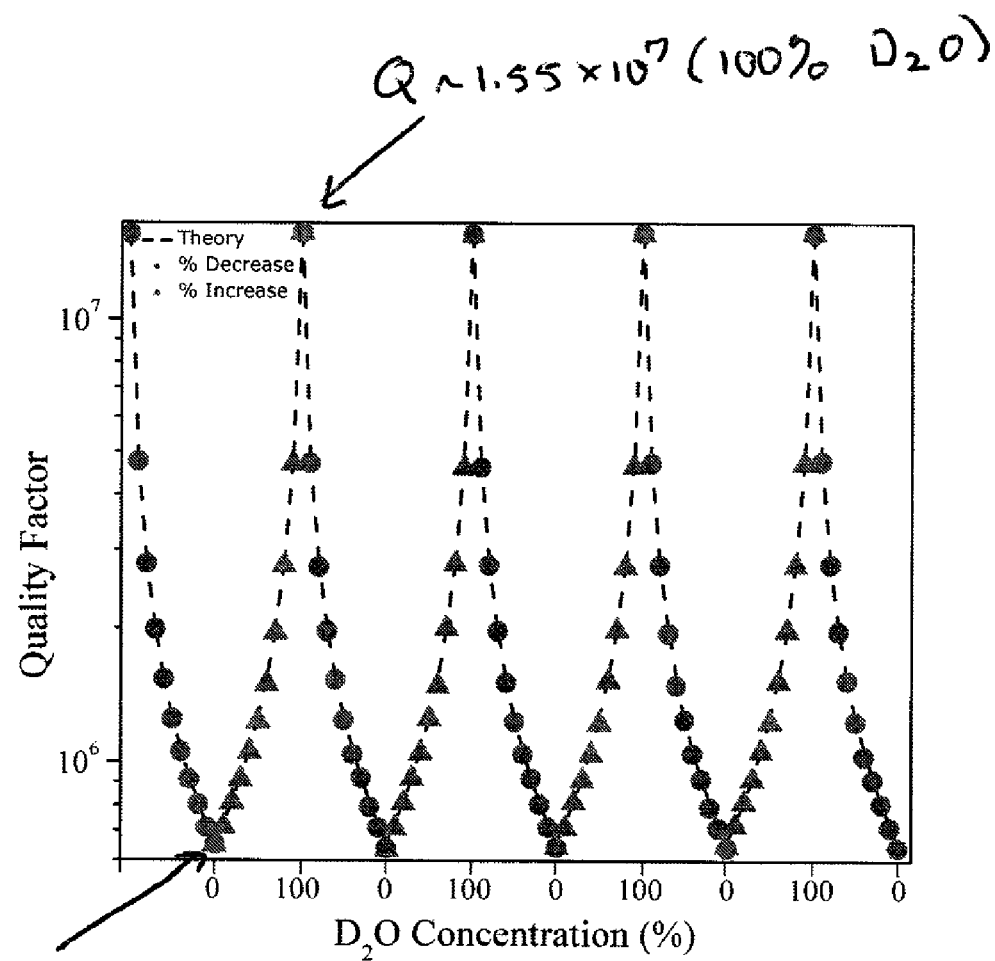
FIG. 29 is a graph illustrating variations of Q value of a micro-toroid resonator relative to different heavy water concentrations.

FIG. 28 is a chart illustrating showing the solutions having different heavy water concentrations (column 2801), the measured Q values (column 2802) and, for comparison, theoretical Q values (column 2803) based on known theoretical values. Initially, with the toroid immersed in 100% heavy water, the measured Q value was about $1.55 \times 10^7$. With further reference to FIG. 29, this represents a maximum Q value of the micro-toroid 100. As the concentration of heavy water was reduced, the Q value of the micro-toroid 100 decreased. The Q value of the micro-toroid 100 in 100% $H_2O$ was about $6.4 \times 10^5$. As shown in FIG. 29, this is a minimum Q value of the micro-toroid 100. FIG. 29 also illustrates that decreasing Q values resulting from decreasing heavy water concentrations were reversible so that Q values increased with increasing heavy water concentrations.

Figure 30:
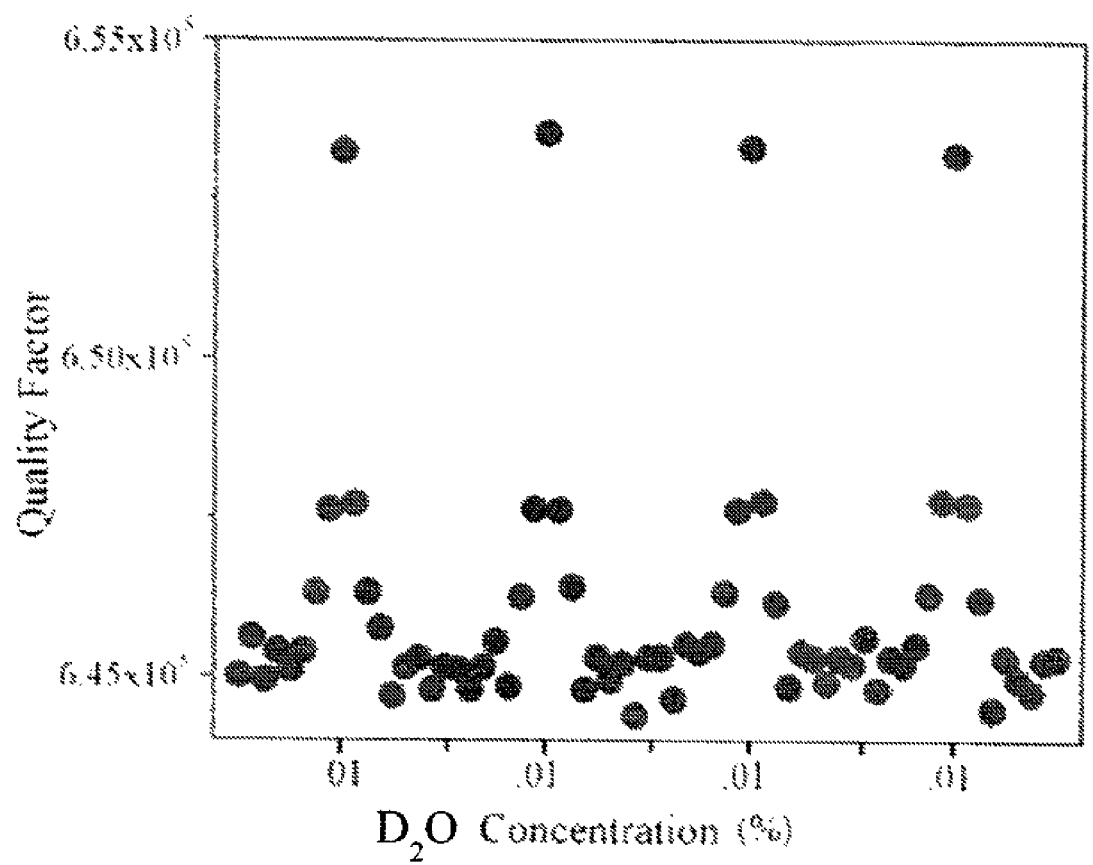
FIG. 30 is a graph further illustrating variations of Q value of a micro-toroid resonator at different heavy water concentrations and detectable Q value changes at a concentration of 1 ppmv.

Referring to FIG. 30, in order to determine higher sensitivity ranges and to what extend smaller quantities of heavy water could be detected with embodiments, solutions were prepared with even smaller concentrations of heavy water. These solutions had heavy water concentrations ranging from 0.01% to $1 \times 10^{-9}$%. During this test, Q values were measured when the micro-toroids 100 were immersed in 100% $H_2O$, and then measured as the heavy water concentrates were slightly increased. As shown in FIGS. 28 and 30, there is a strong signal (notable Q value change) at a concentration of 0.001% heavy water in ordinary water. A smaller and detectable shift occurs with at a concentration of 0.0001% heavy water in heavy water. This sensitivity represents the ability to detect 1 part per million per volume (1 ppmv) heavy water in ordinary water. Such capabilities provide a substantial improvement compared to known heavy water detectors, which are only capable of detecting about 30 ppmv of heavy water in ordinary water.

Figure 31A:
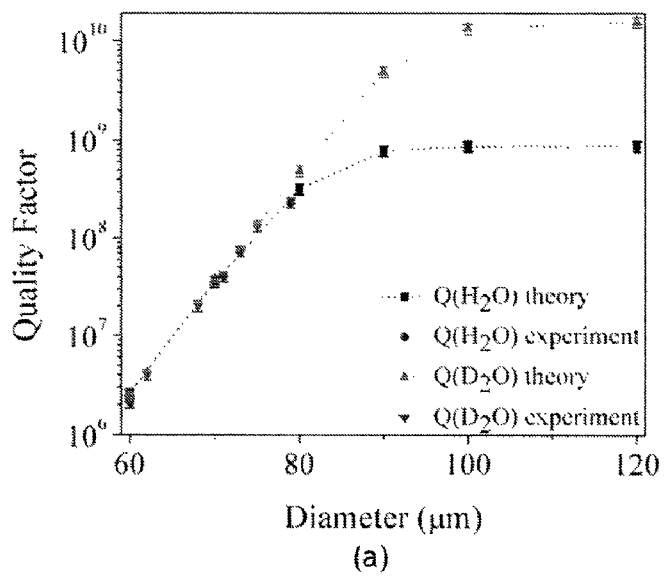
FIG. 31A is a graph illustrating measured and predicted Q values of micro-toroid resonators immersed in an aqueous environment in a 680 nm wavelength band.
Figure 31B:
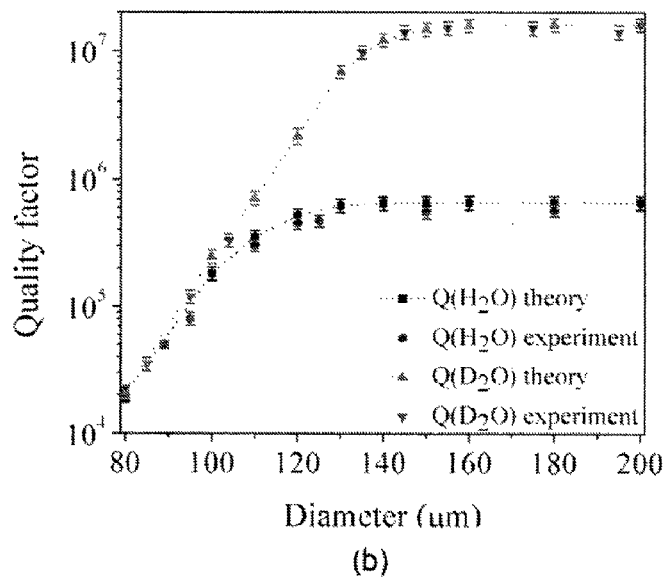
FIG. 31B is a graph illustrating measured and predicted Q values of a micro-toroid resonator immersed in an aqueous environment in a 1300 nm wavelength band.
Figure 31C:
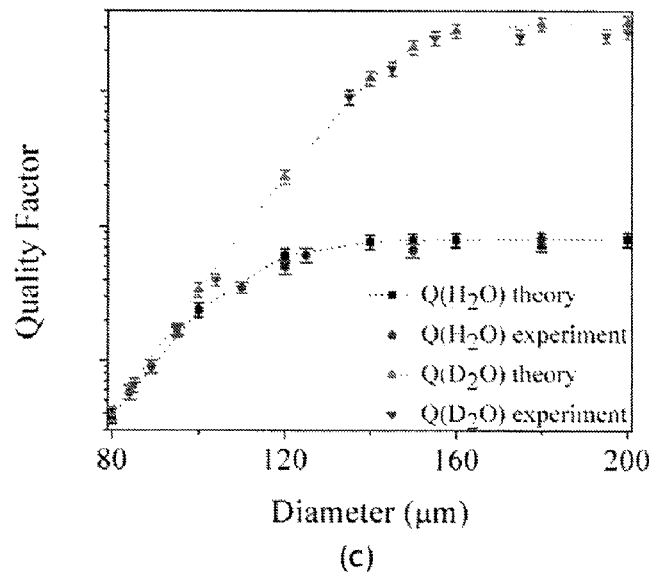
FIG. 31C is a graph illustrating measured and predicted Q values of a micro-toroid resonator immersed in an aqueous environment in a 1550 nm wavelength band.

FIGS. 31A-C illustrate further data of Q value measurements of micro-toroids 100 of different diameters in a water environment having heavy water to illustrate how the size of a micro-toroid 100 can affect heavy water detection capabilities and how test results compared to a theoretical model. The theoretical model that was used for this test utilized finite-element-analysis to predict the Q value of the resonators immersed in water and accounted for two loss mechanisms: radiation-loss and absorption-loss. Absorption loss was numerically calculated at the three different wavelengths using published absorption loss values. Modeling radiation-loss was based on a fully-vectoral 2D eigenmode/eigenvalue solver for the Helmholtz equation. Tests were conducted at three different wavelengths (680 nm 1300 nm and 1570 nm) using published absorption loss values. The heavy water purchased from Sigma-Aldrich Corporation, 3050 Spruce Street, St. Louis, Mo.

Referring to FIG. 31A, intrinsic Q values were measured in the 680 nm band and plotted relative to the different micro-toroid 100 major diameters of a micro-toroid 100 (FIG. 1D). The test indicated that Q values trend to larger values with increasing toroid 100 size, which is consistent with the corresponding theoretical model. The maximum quality factor that was achieved in ordinary water was $2.3 \times 10^8$. The maximum Q value that was achieved in heavy water was $1.3 \times 10^8$. It is believed that resonant sensor embodiments were utilized to achieve the highest Q values in an aqueous environment that have been reported to date. The highest previously recorded Q value was $10^6$ in a large diameter silica microsphere, which is at least two orders of magnitude less than Q values achieved with embodiments of the invention. In principle, larger toroid 100 diameters should exhibit quality factors as high as $1 \times 10^9$ in ordinary water and $1 \times 10^{10}$ in heavy water.

FIG. 31B includes data of measured intrinsic Q values for micro-toroids 100 in ordinary water and heavy water relative to different toroid major diameters in the 1300 nm band. Both the radiation-loss-limited regimes and the absorption-loss-limited regimes are clearly visible in FIG. 30B. Also plotted are predictions based on the theoretical model. Within this wavelength band, heavy water has a lower optical absorption and, therefore, exhibits an absorption-limited Q value plateau that is significantly higher compared to ordinary water (approximately $10^5$ for ordinary water compared to greater than $10^7$ for heavy water). The origin of this absorption limit is the O—H (oxygen-hydrogen) vibration overtone of water. In heavy water, this overtone is wavelength-shifted proportionally, thereby increasing the observable Q value plateau.

FIG. 31C illustrates measured intrinsic Q values relative to toroid major diameter in the 1550 nm band compared to the theoretical model. The measurements are consistent with the model, showing the transition between the radiation-loss-limited and absorptive-loss-limited regimes. Strong OH overtone absorption in ordinary water lowers the Q value plateau to $8 \times 10^4$, while for heavy water, the Q value is higher, increasing to above $3 \times 10^6$.

Thus, embodiments are advantageously able to detect the difference between two chemically similar species, one example of which is detection of heavy water in ordinary water. In this particular embodiment, detection is based on the subtle and detectable difference in optical absorptions between heavy water and ordinary water, which is magnified by high and ultra-high Q values of a microcavity 906 to achieve detection sensitivities as low as 1 part per million per volume (1 ppmv) or 0.0001% heavy water in ordinary water, which is significantly better than prior detection systems that can only detect 30 ppmv of heavy water in ordinary water.

Resonant sensor embodiments can have various Q values while still being able to detect heavy water with enhanced sensitivities compared to known heavy water detectors. In the illustrated embodiment, the resonant sensor was an ultra-high Q toroid-shaped silica micro-resonator (Q>$10^8$). However, embodiments can be implemented using micro-resonators having lower Q values (e.g., Q>$10^7$).

It should also be understood that although this specification describes an example involving heavy water detection, embodiments can be applied to various other monitoring and detection applications and detection of other molecules and species, which may be in solutions or liquids having a mixture of different molecules. Accordingly, the description and figures demonstrating detection of very small quantities of heavy water are provided as an example to demonstrate the power of highly sensitive resonant sensor embodiments and how embodiments can be applied to detect other molecules and species in aqueous environments.

Although references have been made in the foregoing description to various embodiments, persons of ordinary skill in the art will recognize that insubstantial modifications, alterations, and substitutions can be made to the described embodiments without departing from the invention as recited in the accompanying claims. For example, embodiments of resonant sensors can be made of materials other than silica. Further, other substrates besides silicon may be suitable depending on the particular application of the device and integration and coupling considerations. Moreover, various micro-cavities other than micro-toroids can be utilized to implement embodiments. Further, embodiments can be implemented using microcavity resonant sensors individually. Alternatively, multiple microcavity resonant sensors can be utilized, e.g., as an array of sensors. Further, microcavity resonator sensor embodiments can be integrated with other devices (e.g., microfluidic devices) for automation. Additionally, although embodiments that utilize a thermo-optic are described with reference to whispering gallery mode resonators, embodiments, embodiments using thermo-optic interactions can also be implemented with other resonators that are not WGM resonators, such as photonic crystals and vertical cavity surface emitting lasers.

What is claimed is:

1. A method of detecting at least one molecule in an environment, comprising: introducing optical energy into a planar, non-spherical microcavity having a functionalized outer surface and being supported by a substrate, the substrate comprising a bottom portion, a top portion and a middle portion extending between the bottom portion and the top portion, the middle portion comprising a tapered or angled surface such that the bottom portion is wider than the top portion, an inner edge of the planar, non-spherical microcavity extending around an outer edge of the top portion of the substrate such that the substrate supports and elevates the planar, non-spherical microcavity, and an outer edge of the planar, non-spherical microcavity extending outwardly beyond a top outer edge of the substrate; and detecting at least one unlabeled molecule bound to the functionalized outer surface based on a thermo-optic interaction between the at least one molecule and an evanescent field extending beyond an outer edge of the planar, non-spherical microcavity and into the environment.

2. The method of claim 1, introducing optical energy further comprising coupling optical energy into a toroid-shaped microcavity from a waveguide.

3. The method of claim 1, introducing optical energy further comprising coupling energy into a planar, non-spherical microcavity having a Q value greater than $10^6$.

4. The method of claim 1, detecting the at least one unlabeled molecule bound to the functionalized outer surface based on the thermo-optic interaction resulting from the at least one unlabeled molecule binding to the functionalized outer surface, interacting with the evanescent field generated by optical energy circulating inside the planar, non-spherical microcavity and heating the planar, non-spherical microcavity, thereby causing a detectable shift of the wavelength of the optical energy resonating in the planar, non-spherical microcavity.

5. The method of claim 1, detecting the at least one unlabeled molecule comprising detecting a single unlabeled molecule bound to the functionalized outer surface.

6. The method of claim 1, wherein the environment is an aqueous environment.

7. A method of detecting at least one molecule in an environment, comprising: introducing optical energy into a planar, non-spherical silica microcavity having a functionalized outer surface and being supported by a substrate, the substrate comprising a bottom portion, a top portion and a middle portion extending between the bottom portion and the top portion, the middle portion comprising a tapered or angled surface such that the bottom portion is wider than the top portion, an inner edge of the planar, non-spherical silica microcavity extending around an outer edge of the top portion of the substrate such that the substrate supports and elevates the planar, non-spherical silica microcavity, and an outer edge of the planar, non-spherical silica microcavity extending outwardly beyond a top outer edge of the substrate; and detecting at least one molecule bound to the functionalized outer surface based on a wavelength shift of the optical energy resonating in the planar, non-spherical silica microcavity.

8. The method of claim 7, detecting at least one molecule further comprising detecting a single unlabeled molecule bound to the functionalized outer surface.

9. The method of claim 7, introducing optical energy further comprising introducing optical energy into a toroid-shaped planar, non-spherical silica microcavity.

10. The method of claim 7, detecting at least one molecule being based on a thermo-optic interaction resulting from the at least one molecule binding to the functionalized outer surface, interacting with the evanescent field generated by optical energy circulating inside the planar, non-spherical silica microcavity and heating the planar, non-spherical silica microcavity, thereby causing a detectable shift of the wavelength of the optical energy resonating in the planar, non-spherical silica microcavity.

11. The method of claim 7, wherein the environment is an aqueous environment.

12. A method of detecting at least one molecule in an environment, comprising: introducing optical energy into an ultra-high Q planar, non-spherical microcavity having a Q value of at least $1 \times 10^8$ and a functionalized outer surface and being supported by a substrate, the substrate comprising a bottom portion, a top portion and a middle portion extending between the bottom portion and the top portion, the middle portion comprising a tapered or angled surface such that the bottom portion is wider than the top portion, an inner edge of the ultra-high Q planar, non-spherical microcavity extending around an outer edge of the top portion of the substrate such that the substrate supports and elevates the ultra-high Q planar, non-spherical microcavity, and an outer edge of the ultra-high Q planar, non-spherical microcavity extending outwardly beyond a top, outer edge of the substrate; and detecting at least one molecule bound to the functionalized outer surface based on a wavelength shift of the optical energy resonating in the ultra-high Q planar, non-spherical microcavity.

13. The method of claim 12, detecting at least one molecule comprising detecting a single unlabeled molecule bound to the functionalized outer surface.

14. The method of claim 12, introducing optical energy further comprising introducing optical energy into a toroid-shaped ultra-high Q planar, non-spherical microcavity.

15. The method of claim 12, detecting the at least one molecule being based on a thermo-optic interaction resulting from the at least one molecule binding to the functionalized outer surface, interacting with the evanescent field generated by optical energy circulating inside the ultra-high Q planar, non-spherical microcavity and heating the ultra-high Q planar, non-spherical microcavity, thereby causing a detectable shift of the wavelength of the optical energy resonating in the ultra-high Q planar, non-spherical microcavity.

16. The method of claim 12, wherein the environment is an aqueous environment.

17. A resonant sensor for detecting at least one molecule in an environment, comprising: a planar, non-spherical silica microcavity having a functionalized outer surface and being supported by a substrate, the substrate comprising a bottom portion, a top portion and a middle portion extending between the bottom portion and the top portion, the middle portion comprising a tapered or angled surface such that the bottom portion is wider than the top portion, an inner edge of the planar, non-spherical silica microcavity extending around an outer edge of the top portion of the substrate such that the substrate supports and elevates the planar, non-spherical silica microcavity; and a waveguide positioned to couple optical energy into the planar, non-spherical silica microcavity, the planar, non-spherical silica microcavity having a sufficiently high Q value to allow detection of individual molecules bound to the functionalized outer surface based on a wavelength shift of the optical energy resonating in the planar, non-spherical silica microcavity.

18. The resonant sensor of claim 17, wherein an outer edge of the planar, non-spherical silica microcavity extends outwardly beyond an outer top edge of the substrate.

19. The resonant sensor of claim 17, wherein the planar, non-spherical silica microcavity has a toroid shape.

20. The resonant sensor of claim 17, wherein the functionalized outer surface includes a chemically active substance or a biologically active substance.

21. The resonant sensor of claim 20, wherein the functionalized outer surface includes an antibody or an antigen.

22. The resonant sensor of claim 20, wherein the functionalized outer surface includes a protein.

23. The resonant sensor of claim 17 being adapted to detect a single unlabeled molecule.

24. The resonant sensor of claim 17 being adapted to detect individual molecules based on a thermo-optic interaction resulting from a molecule binding to the functionalized outer surface, interacting with the evanescent field generated by optical energy circulating inside the planar, non-spherical silica microcavity and heating the planar, non-spherical silica microcavity, thereby causing a detectable shift of the wavelength of the optical energy resonating in the planar, non-spherical silica microcavity.

25. The resonator sensor of claim 17 being adapted to operate in an aqueous environment.

26. The resonant sensor of claim 17, wherein a plane defined by the planar, non-spherical silica microcavity and a plane defined by a top surface of the top portion of the substrate are substantially parallel.

27. The resonant sensor of claim 17, wherein the substrate is silicon.

28. A resonant sensor for detecting at least one molecule in an environment, comprising: an ultra-high Q planar, non-spherical microcavity having a functionalized outer surface and a Q value greater than $1 \times 10^8$; a substrate supporting the ultra-high Q planar, non-spherical microcavity, the substrate comprising a bottom portion, a top portion and a middle portion extending between the bottom portion and the top portion, the middle portion comprising a tapered or angled surface such that the bottom portion is wider than the top portion, an inner edge of the ultra-high Q planar, non-spherical microcavity extending around an outer edge of the top portion of the substrate such that the substrate supports and elevates the ultra-high Q planar, non-spherical microcavity; and a waveguide positioned to couple optical energy into the ultra-high Q planar, non-spherical microcavity, the ultra-high Q planar, non-spherical microcavity having a sufficiently high Q value to allow detection of individual molecules bound to the functionalized outer surface based on a shift of a wavelength of the optical energy resonating in the ultra-high Q planar, non-spherical microcavity.

29. The resonant sensor of claim 28, wherein an outer edge of the ultra-high Q planar, non-spherical microcavity extends outwardly beyond an outer top edge of the substrate.

30. The resonant sensor of claim 28, wherein the ultra-high Q planar, non-spherical microcavity has a toroid shape.

31. The resonant sensor of claim 28 being adapted to detect individual molecules based on a thermo-optic interaction resulting from a molecule binding to the functionalized outer surface, interacting with the evanescent field generated by optical energy circulating inside the ultra-high Q planar, non-spherical microcavity and heating the ultra-high Q planar, non-spherical microcavity, thereby causing a detectable shift of the wavelength of optical energy resonating in the ultra-high Q planar, non-spherical microcavity.

32. The resonator sensor of claim 28 being adapted to operate in an aqueous environment.

33. The resonant sensor of claim 29, wherein a plane defined by the ultra-high Q planar, non-spherical microcavity and a plane defined by a top surface of the top portion of the substrate are substantially parallel.

34. The resonant sensor of claim 29, wherein the ultra-high Q planar, non-spherical microcavity is silica and the substrate is silicon.

35. A resonant sensor for detecting at least one molecule in an environment, comprising: an ultra-high Q planar, non-spherical microcavity made of silica and having a functionalized outer surface, the microcavity having a Q value of at least $10^8$; a substrate that supports the ultra-high Q planar, non-spherical microcavity made of silica, wherein the substrate is made a material other than silica and comprises a bottom portion, a top portion and a middle portion extending between the bottom portion and the top portion, the middle portion comprising a tapered or angled surface such that the bottom portion is wider than the top portion, an inner edge of ultra-high Q planar, non-spherical microcavity extending around an outer edge of the top portion of the substrate such that the substrate supports and elevates the ultra-high Q planar, non-spherical microcavity; and a waveguide positioned to couple optical energy into the ultra-high Q planar, non-spherical microcavity, the Q value of the ultra-high Q planar, non-spherical microcavity allowing detection of individual molecules bound to the functionalized outer surface based on a shift of a wavelength of the optical energy resonating in the ultra-high Q planar, non-spherical micro-cavity.

36. The resonant sensor of claim 35, wherein an outer edge of the ultra-high Q planar non-spherical microcavity extends outwardly beyond an outer top edge of the substrate.

37. The resonant sensor of claim 35, wherein a plane defined by the ultra-high Q planar, non-spherical microcavity and a plane defined by a top surface of the top portion of the substrate are substantially parallel.

38. The resonant sensor of claim 35, wherein the substrate is silicon.

* * * * *